US010793553B2

(12) United States Patent
Sherer et al.

(10) Patent No.: US 10,793,553 B2
(45) Date of Patent: Oct. 6, 2020

(54) TLR7/8 ANTAGONISTS AND USES THEREOF

(71) Applicant: Merck Patent GmbH, Darmstadt (DE)

(72) Inventors: Brian A. Sherer, Nashua, NH (US);
Nadia Brugger, Cambridge, MA (US);
Ruoxi Lan, Waltham, MA (US);
Xiaoling Chen, Chestnut Hill, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/037,368

(22) Filed: Jul. 17, 2018

(65) Prior Publication Data

US 2019/0023687 A1    Jan. 24, 2019

Related U.S. Application Data

(60) Provisional application No. 62/533,820, filed on Jul. 18, 2017.

(51) Int. Cl.
| | | |
|---|---|---|
| *C07D 403/10* | (2006.01) | |
| *A61P 9/10* | (2006.01) | |
| *A61P 29/00* | (2006.01) | |
| *A61P 19/02* | (2006.01) | |
| *A61P 35/00* | (2006.01) | |
| *A61P 3/10* | (2006.01) | |
| *C07D 401/14* | (2006.01) | |
| *C07D 401/10* | (2006.01) | |
| *A61P 25/16* | (2006.01) | |
| *A61P 17/06* | (2006.01) | |
| *C07D 471/04* | (2006.01) | |
| *A61P 25/28* | (2006.01) | |

(52) U.S. Cl.
CPC .............. *C07D 403/10* (2013.01); *A61P 3/10* (2018.01); *A61P 9/10* (2018.01); *A61P 17/06* (2018.01); *A61P 19/02* (2018.01); *A61P 25/16* (2018.01); *A61P 25/28* (2018.01); *A61P 29/00* (2018.01); *A61P 35/00* (2018.01); *C07D 401/10* (2013.01); *C07D 401/14* (2013.01); *C07D 471/04* (2013.01)

(58) Field of Classification Search
CPC .. C07D 403/10; C07D 401/10; C07D 401/14; C07D 471/04; A61P 17/06; A61P 9/10; A61P 25/28; A61P 19/02; A61P 3/10; A61P 29/00; A61P 35/00
See application file for complete search history.

(56) References Cited

U.S. PATENT DOCUMENTS 4,933,447 A * 6/1990 Koono ................. C07D 215/48
544/128

FOREIGN PATENT DOCUMENTS

| | | | | |
|---|---|---|---|---|
| EP | 0 308 897 | 3/1989 | | |
| EP | 1 553 074 | 7/2005 | | |
| EP | 1 987 827 | 11/2008 | | |
| WO | WO-2005115361 A2 * | 12/2005 | ........... | C07C 255/58 |
| WO | 2008/126034 | 10/2008 | | |
| WO | 2010/003133 | 1/2010 | | |
| WO | 2013/060881 | 5/2013 | | |
| WO | 2015/057655 | 4/2015 | | |
| WO | 2015/057659 | 4/2015 | | |
| WO | 2015/092592 | 6/2015 | | |
| WO | 2017/106607 | 6/2017 | | |

OTHER PUBLICATIONS

Surivet et al., 22(21) Bioorg. & Med. Chem. Letts. 6705-6711 (2012) (CAS Abstract) (Year: 2012).*
Barrat and Coffman, Immunol Rev, 223:271-283 (2008).
Berge et al., Pharmaceutical Salts, J. Pharma Sciences, 66(1): 1-19 (1977).
Enevold et al., J Rheumatol, 37:905-10 (2010).
Foster A.B., Advances in Drug Research, 14: 1-39 (1985).
Gillette et al., Biochemistry, 33(10): 2927-2937 (1994).
Theodora W. Greene and Peter G. M. Wuts in "Protective Groups in Organic Synthesis", Wiley Interscience, 3rd Edition 1999.
Handbook of Chemistry and Physics, 75th Ed.
Hanzlik et al., J. Org. Chem., 155: 3992-3997 (1990).
Jarman et al., Carcinogenesis, 16(4): 683-688 (1995).
Philip J. Kocienski, in "Protecting Groups", Georg Thieme Verlag Stuttgart, New York, 1994.
March's Advanced Organic Chemistry, 5th Ed., Ed.: Smith, M.B. and March, J., John Wiley & Sons, New York: 2001.
Organic Chemistry, Thomas Sorrell, University Science Books, Sausalito,1999.
Periodic Table of the Elements, CAS version.
Reider et al., J. Org. Chem., 52(15): 3326-3334 (1987).
International Search Report dated Oct. 26, 2018 in International Application No. PCT/US2018/042417, 11 pages.
Andaloussi et al., Bioorganic & Medicinal Chemistry Letters; 2013, 23(9):2663-2670.
Elderfield et al., Journal of Organic Chemistry; 1952, 17(3):431-441.
Database Registry, American Chemical Society, Chemical Abstracts Service; Nov. 2004, Accession No. 775541-12-3, 3 pages.

* cited by examiner

*Primary Examiner* — Timothy R Rozof
(74) *Attorney, Agent, or Firm* — Grüneberg and Myers PLLC

(57) ABSTRACT

The present invention relates to compounds of Formula I and pharmaceutically acceptable compositions thereof, useful as TLR7/8 antagonists.

17 Claims, No Drawings

TLR7/8 ANTAGONISTS AND USES THEREOF

RELATED APPLICATION

This application claims the benefit of U.S. Provisional application No. 62/533,820, filed on Jul. 18, 2017. The content of the aforementioned application is hereby incorporated by reference in its entirety.

TECHNICAL FIELD OF THE INVENTION

The present invention provides for compounds of Formula (I) as toll-like receptor 7/8 (TLR7/8) antagonists and their use in the treatment of immune disorders, and other diseases related to TLR7/8 overexpression.

BACKGROUND OF THE INVENTION

Toll-like receptors (TLR) currently comprising a gene family of 10 receptors with different specificities are part of the cellular pathogen pattern recognition system, which has evolved for defense against a variety of infections (bacteria, virus, fungi). Activation of TLRs leads to cytokine responses, e.g. with release of interferons and activation of specified immune cells. The functional expression of selected TLRs in tissues is highly different. Part of the receptors are located at the cell surface such as TLR4 (stimulated by *E. coli* lipopolysaccharide LPS), e.g. on epithelial cells, or TLR3, 7, 8 and 9 located at endosomal membranes in specified immune cells. The latter are all activated by nucleic acids, but recognize various types of them. For instance, TLR9 is activated by single stranded DNA containing CpG subsequences, TLR7 and 8 are activated by single stranded RNA, and TLR3 is activated by double-stranded RNA.

TLRs have been implicated in various autoimmune and inflammatory diseases, with the clearest example being the role played by TLR7 in the pathogenesis of systemic lupus erythematosus (Barrat and Coffman, Immunol Rev, 223: 271-283, 2008). Additionally, a TLR8 polymorphism has been associated with rheumatoid arthritis (Enevold et al., J Rheumatol, 37:905-10, 2010). Although various TLR7, TLR8 and TLR9 inhibitors have been described, additional TLR inhibitors are desirable. In particular, polynucleotides having inhibitory motifs for one or more of TLR7, TLR8 and TLR9 are needed to precisely inhibit an immune response in a subject (e.g., patient having an autoimmune disease or an inflammatory disorder).

For several years strong efforts are ongoing worldwide trying to exploit the strong immune activation induced by TLR7, 8 or 9 agonists for the treatment of cancer. Cancer immunotherapy, however, experienced a long history of failures. In recent years, though, the knowledge on cancer immune surveillance and the function of subsets of immune cells thereby was improved drastically. TLR7 or TLR9 agonists are in clinical development for cancer mono- or combination therapies, or as vaccine adjuvant. The TLR agonist approach for cancer immunotherapy is different from earlier efforts using, e.g. cytokines, interferons or monovalent vaccinations. TLR agonist mediated immune activation is pleiotropic via specified immune cells (primarily dendritic cells and B-cells, subsequently other cells), which generates an innate and adaptive immune response. Moreover, not only one interferon is induced, but rather the many different isoform's altogether, and not only type I (alpha, beta), but also (indirectly) type II (gamma, NK cells).

SUMMARY OF THE INVENTION

In one aspect, the invention provides compounds of Formula (I):

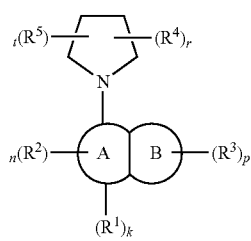

I and pharmaceutically acceptable derivatives, solvates, salts, hydrates and stereoisomers thereof.

In another aspect, the invention provides compounds of Formula (I) which are dual antagonists of TLR7 and TLR8. In another aspect, the invention provides compounds of Formula (I) which are suitable for the treatment and/or prevention of disorders related to TLR7/8. In another aspect, the invention provides compounds which are able to modulate, especially inhibit the activity or function of TLR7/8 in disease states in mammals, especially in humans.

According to another aspect of the invention are provided methods for the treatment and/or prevention of auto-immune disorders.

According to another aspect, the present invention provides compounds of Formula (I) which are selective for TLR7 or TLR8.

According to another aspect, the present invention provides compounds of Formula (I) which are selective for TLR7 and TLR8.

DETAILED DESCRIPTION OF CERTAIN EMBODIMENTS

1. General Description of Compounds of the Invention

In certain aspects, the present invention provides for antagonists of TLR7/8. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Fused rings, as described herein, are described by embodiments for each ring; Ring A and Ring B. Together, Ring A and Ring B form a fused heteroaryl ring as allowed by valence (e.g., when Ring A is

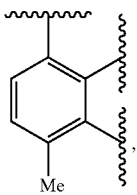 [SMILES: *c1ccc(C)c(*)c1*]

and Ring B is

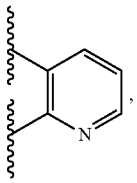 [SMILES: *c1cccnc1*]

then together Ring A and Ring B is

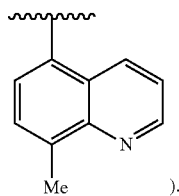 [SMILES: *c1ccc(C)c2ncccc12]

).

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

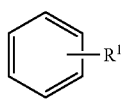

refers to at least

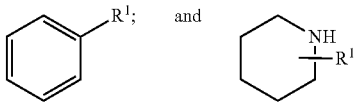

refers to at least

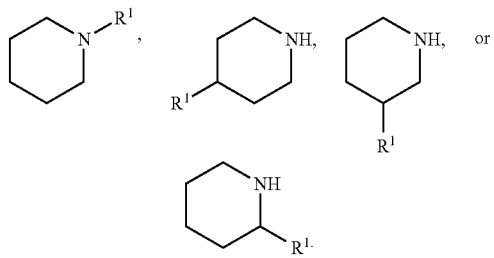

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which are optionally substituted with R°; —$(CH_2)_{0-4}O(CH_2)_{0-1}Ph$ which is optionally substituted with R°; —CH=CHPh, which is optionally substituted with R°; —$(CH_2)_{0-4}O(CH_2)_{0-1}$-pyridyl which is optionally substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° is optionally substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— -alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)-heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,
—CH$_2$NH$_2$, —CH$_2$SO$_2$CH$_3$,
-mono-, di-, or tri-alkyl silyl,
-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in TLR7/8 activity between a sample comprising a compound of the present invention, or composition thereof, and TLR7/8, and an equivalent sample comprising TLR7/8, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups.

The recitation of an embodiment for a variable herein includes that embodiment as any single embodiment or in combination with any other embodiments or portions thereof.

3. Description of Exemplary Compounds

According to one aspect, the present invention provides a compound of formula I,

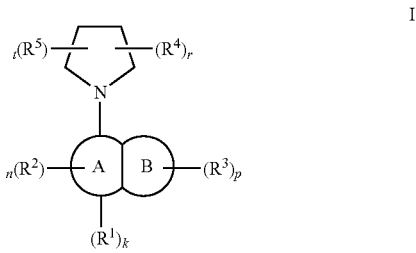

or a pharmaceutically acceptable salt thereof, wherein:

Ring A is aryl or heteroaryl having 1-4 heteroatoms independently selected from nitrogen, oxygen, and sulfur; each of which is optionally substituted;

Ring B is heteroaryl having 1-4 heteroatoms independently selected from nitrogen, oxygen, and sulfur; each of which is optionally substituted;

$R^1$ is —$CH_3$, —$CF_3$ or —CN;

each $R^2$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

each $R^3$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

each $R^4$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRC(O)OR, —$NRSO_2R$, or N(R)$_2$;

each $R^5$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

k is 0, 1 or 2;
n is 0, 1, or 2;
p is 0, 1, or 2;

r is 1, 2, or 3; and t is 1, 2, or 3;

wherein k is 0 when connected to nitrogen; and k is 1 or 2 when connected to carbon.

In certain embodiments, $R^1$ is —CH$_3$.

In certain embodiments, $R^1$ is —CF$_3$.

In certain embodiments, $R^1$ is —CN.

In certain embodiments, k is 0 and $R^1$ is absent.

In certain embodiments, Ring A is phenyl or a 6 membered monocyclic heteroaryl having 1-4 heteroatoms independently selected from nitrogen, oxygen, or sulfur.

In certain embodiments, Ring A is phenyl, pyridyl, pyrimidinyl, pyrazinyl, pyridazinyl, or triazinyl.

In certain embodiments, Ring A is phenyl or pyridyl.

In certain embodiments, Ring A is

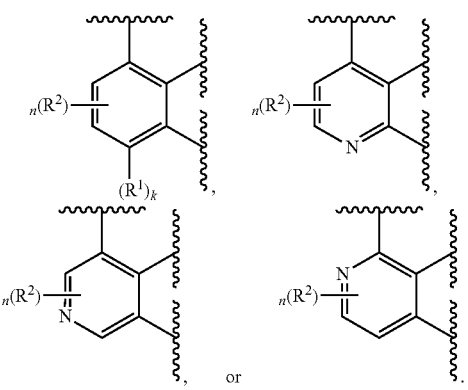

In certain embodiments, Ring A is

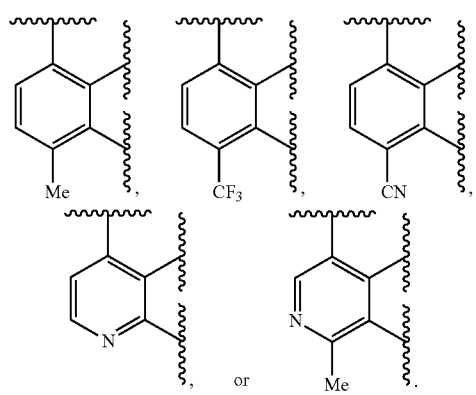

In certain embodiments, Ring A is

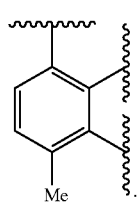

In certain embodiments, Ring A is

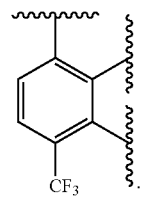

In certain embodiments, Ring A is

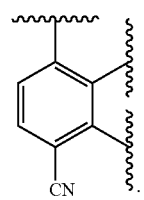 [SMILES: *c1ccc(C#N)c(*)c1*]

In certain embodiments, Ring A is

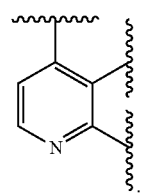 [SMILES: *c1ccnc(*)c1*]

In certain embodiments, Ring A is

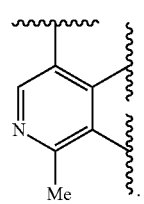 [SMILES: *c1cnc(C)c(*)c1*]

In certain embodiments, Ring B is a 5-6 membered monocyclic heteroaryl having 1-4 heteroatoms independently selected from nitrogen, oxygen, and sulfur.

In certain embodiments, Ring B is pyridyl, pyrimidinyl, pyrazinyl, pyridazinyl, triazinyl, pyrrole, imidazole, isoxazole, oxazole, or thiazole; each of which is optionally substituted.

In certain embodiments, Ring B is pyridyl, pyrazinyl, or pyrrole; each of which is optionally substituted.

In certain embodiments, Ring B is

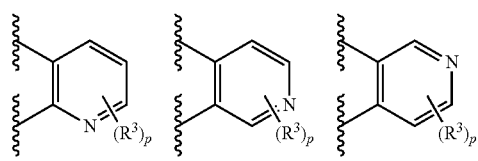

-continued

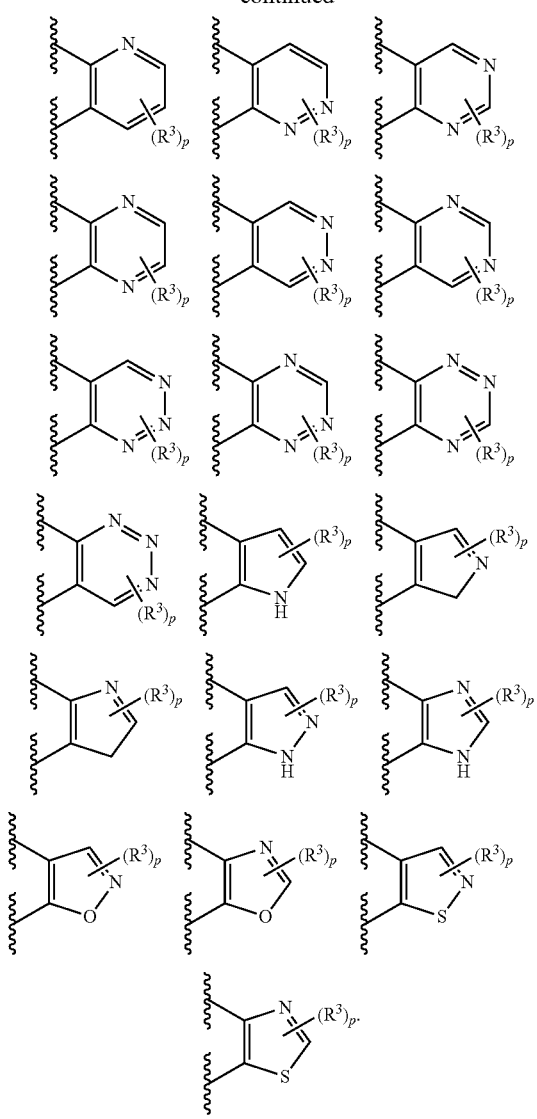

In certain embodiments, Ring B is

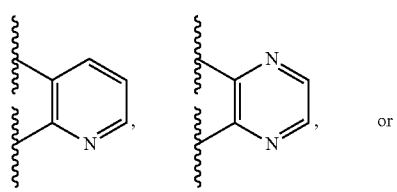

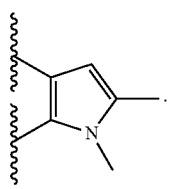

In certain embodiments, Ring B is

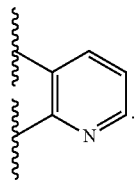 [SMILES: *c1cccnc1*]

In certain embodiments, Ring B is

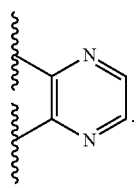 [SMILES: *c1nccnc1*]

In certain embodiments, Ring B is

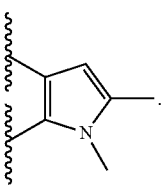 [SMILES: *c1cc(C)n(C)c1*]

In certain embodiments, each $R^2$ is independently —H.

In certain embodiments, each $R^2$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^2$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^2$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^2$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^3$ is independently —H.

In certain embodiments, each $R^3$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^3$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^3$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^3$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^4$ is independently —H.

In certain embodiments, each $R^4$ is independently $C_{1-6}$ aliphatic, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRC(O)OR, —NRC(O)OR, —NRSO$_2$R, or —N(R)$_2$.

In certain embodiments, each $R^4$ is independently $C_{1-6}$ aliphatic, —OR, —C(O)R, —CO$_2$R, —C(O)N(R)$_2$, —NRC(O)R, —NRC(O)OR, —NRC(O)N(R)$_2$, —NRSO$_2$R, or —N(R)$_2$; each of which is optionally substituted.

In certain embodiments, each $R^4$ is independently $C_{1-6}$ aliphatic, —C(O)N(R)$_2$, —NRC(O)R, or —N(R)$_2$; each of which is optionally substituted.

In certain embodiments, each $R^4$ is independently

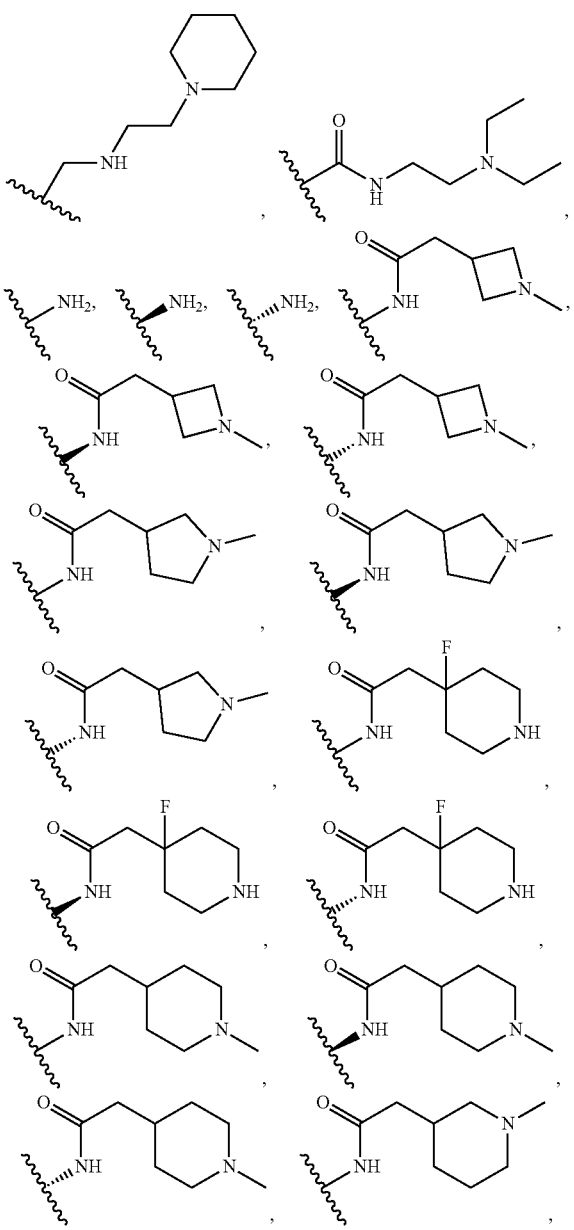

-continued

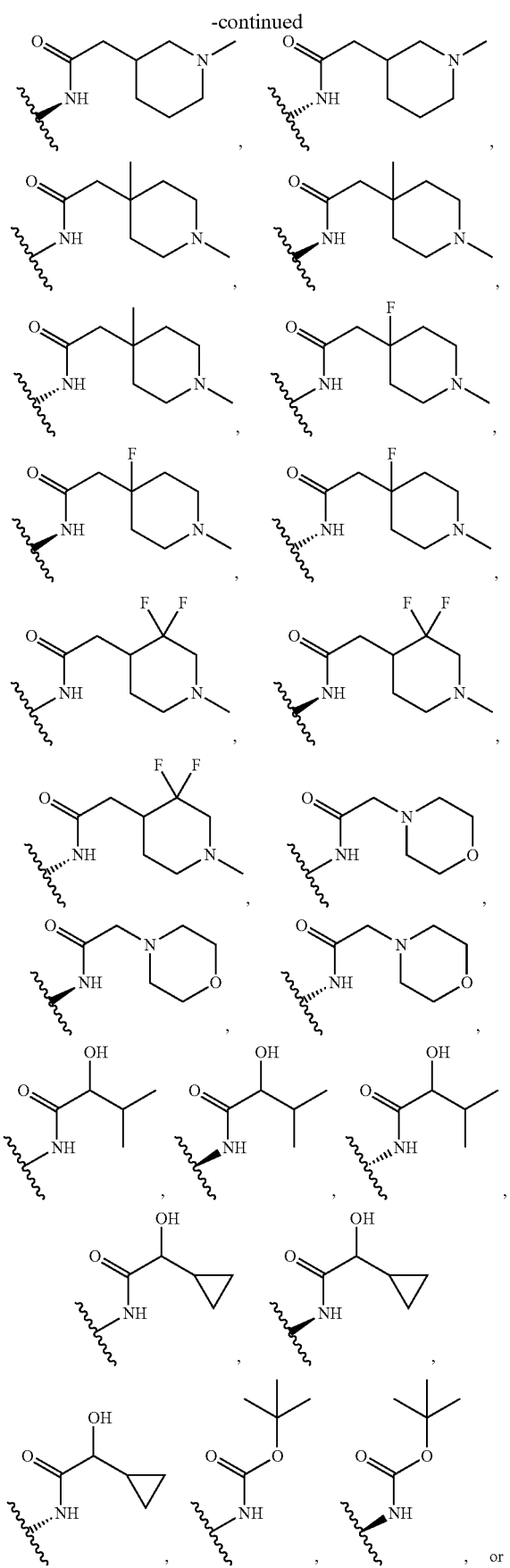

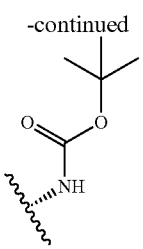

In certain embodiments, each $R^5$ is independently —H.

In certain embodiments, each $R^5$ is independently halogen, $C_{1-6}$ aliphatic, $C_{3-10}$ aryl, a 3-8 membered saturated or partially unsaturated carbocyclic ring, a 3-7 membered heterocyclic heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^5$ is independently methyl, ethyl, propyl, i-propyl, butyl, s-butyl, t-butyl, straight or branched pentyl, or straight or branched hexyl; each of which is optionally substituted; or each $R^5$ is independently —F, —Cl, —Br, or —I.

In certain embodiments, each $R^5$ is independently methyl, ethyl, —F, —Cl, or —Br.

In certain embodiments, each $R^5$ is independently

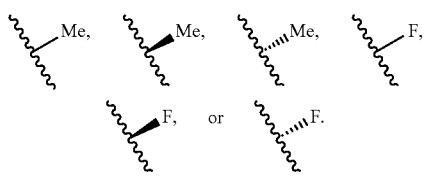

In certain embodiments, each of Ring A, Ring B, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-a,

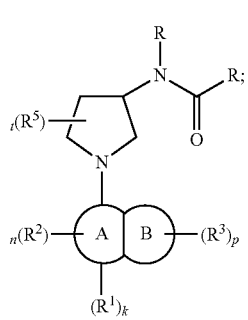

I-a or a pharmaceutically acceptable salt thereof, wherein each of R, $R^1$, $R^4$, $R^5$, r, and t, is as defined above and described in embodiments, classes and subclasses above and herein, singly or in combination.

In certain embodiments, the present invention provides a compound of formula I-b,

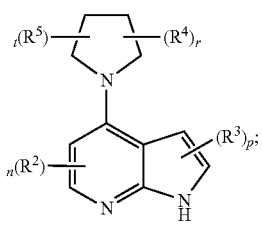

I-b or a pharmaceutically acceptable salt thereof, wherein each of $R^2$, $R^3$, $R^4$, $R^5$, n, p, r, and t, is as defined above and described in embodiments, classes and subclasses above and herein, singly or in combination.

In certain embodiments, the present invention provides a compound of formula I-c,

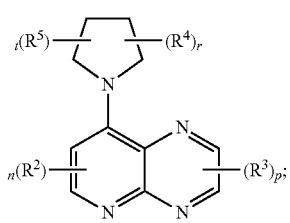

I-c or a pharmaceutically acceptable salt thereof, wherein each of $R^2$, $R^3$, $R^4$, $R^5$, n, p, r, and t, is as defined above and described in embodiments, classes and subclasses above and herein, singly or in combination.

In certain embodiments, the present invention provides a compound of formula I-c,

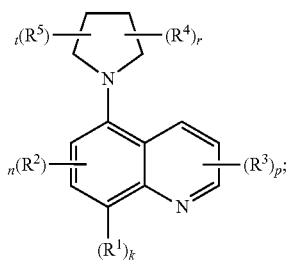

I-c or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-d,

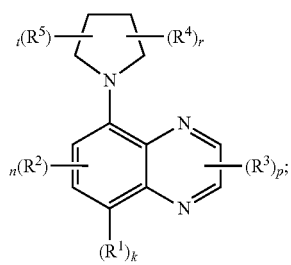

I-d or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-e,

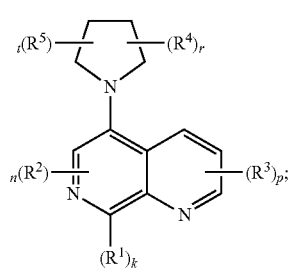

I-e or a pharmaceutically acceptable salt thereof, wherein each of $R^1$, $R^2$, $R^3$, $R^4$, $R^5$, k, n, p, r, and t, is as defined above and described in embodiments, classes and subclasses above and herein, singly or in combination.

In certain embodiments, the invention provides a compound selected from Table 1:

TABLE 1

| Compound Number | Example Number | Chemical Structure |
|---|---|---|
| 1 | 1 | 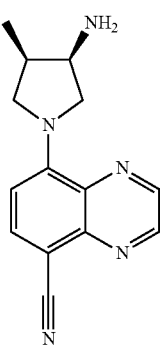 [SMILES: C[C@@H]1CN(c2ccc(C#N)c3nccnc23)C[C@@H]1N] |

TABLE 1-continued
| Compound Number | Example Number | Chemical Structure |
|---|---|---|
| 2 | 2 | 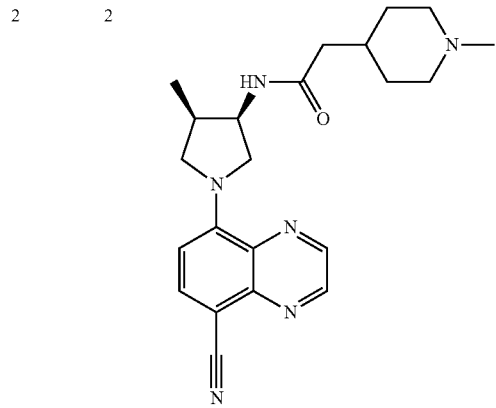 |
| 3 | 3 | 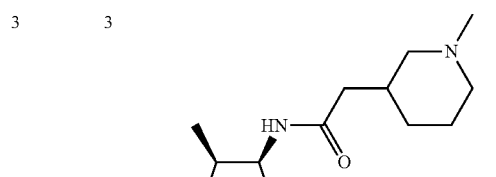 Isomer 1 |
| 4 | 3 | 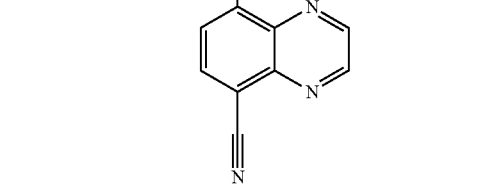 Isomer 2 |
| 5 | 3 | 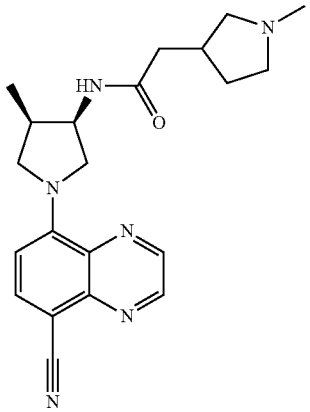 Isomer 1 |
| 6 | 3 | 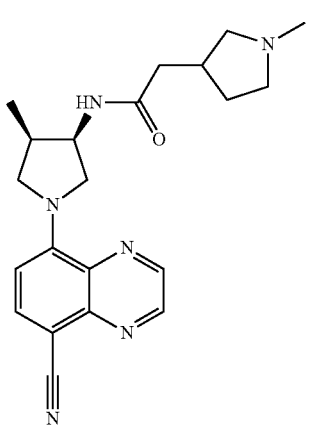 Isomer 2 |
| 7 | 2 | 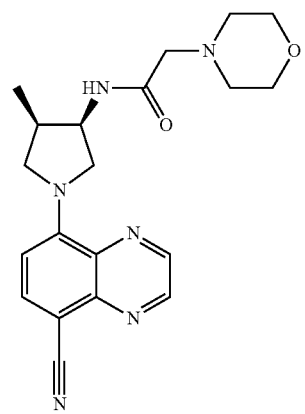 [SMILES: C[C@@H]1CN(c2ccc(C#N)c3nccnc23)C[C@@H]1NC(=O)CN1CCOCC1] |

TABLE 1-continued
| Compound Number | Example Number | Chemical Structure |
|---|---|---|
| 8 | 2 | 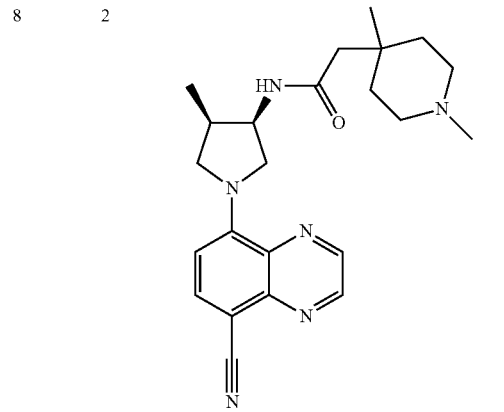 |
| 9 | 4 | 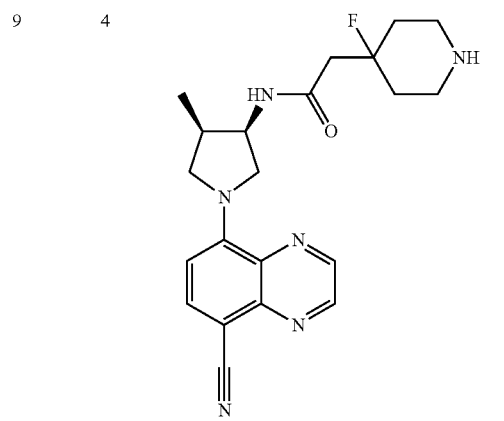 |
| 10 | 5 | 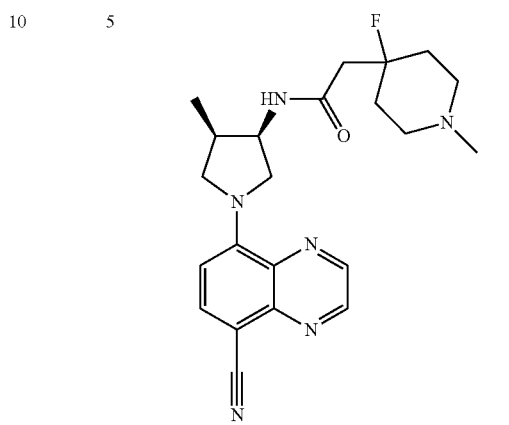 |
TABLE 1-continued
| Compound Number | Example Number | Chemical Structure |
|---|---|---|
| 11 | 6 | 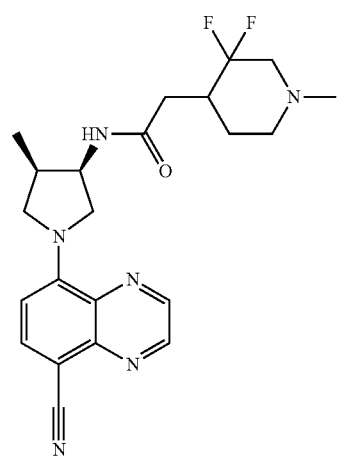<br>Isomer 1 |
| 12 | 6 | 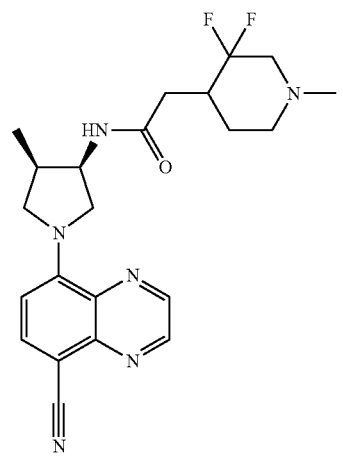<br>Isomer 2 |
| 13 | 3 | 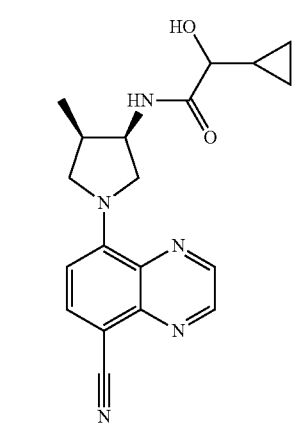<br>Isomer 1 |

TABLE 1-continued
| Compound Number | Example Number | Chemical Structure |
|---|---|---|
| 14 | 3 | 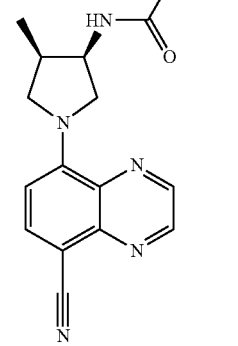<br>Isomer 2 |
| 15 | 2 | 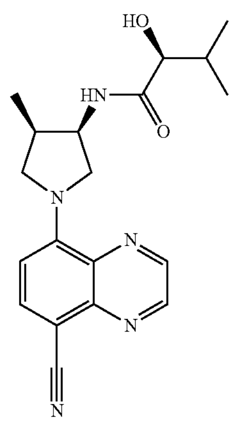 [SMILES: CC(C)[C@H](O)C(=O)N[C@H]1CN(c2ccc(C#N)c3nccnc23)C[C@H]1C] |
| 16 | 2 | 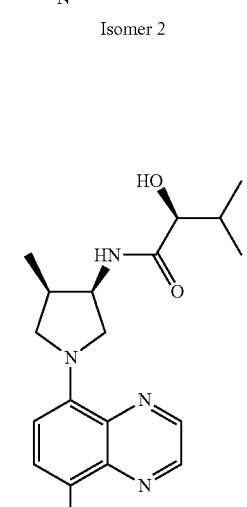 |
TABLE 1-continued
| Compound Number | Example Number | Chemical Structure |
|---|---|---|
| 17 | 7 | 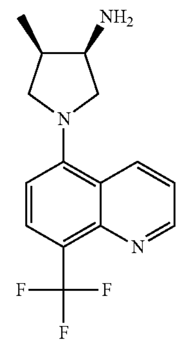 [SMILES: C[C@@H]1CN(c2ccc(C(F)(F)F)c3ncccc23)C[C@@H]1N] |
| 18 | 8 | 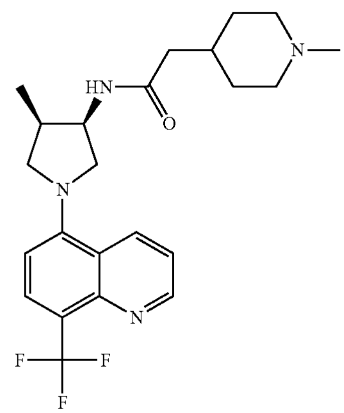 |
| 19 | 9 | 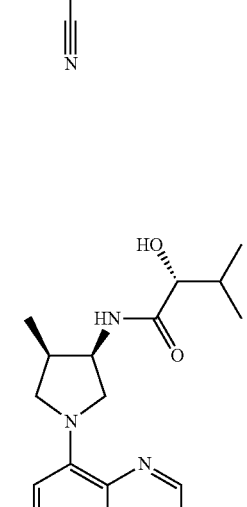<br>Isomer 1 |

TABLE 1-continued
| Compound Number | Example Number | Chemical Structure |
|---|---|---|
| 20 | 9 | 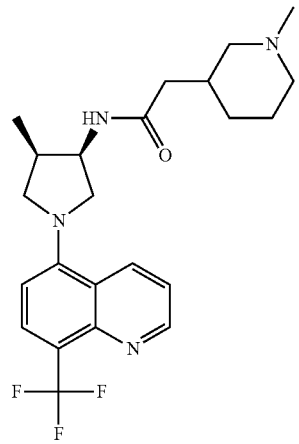<br>Isomer 2 |
| 21 | 9 | 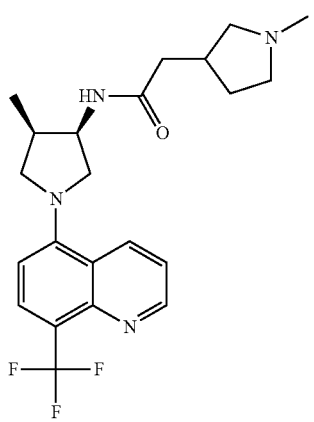<br>Isomer 1 |
| 22 | 9 | 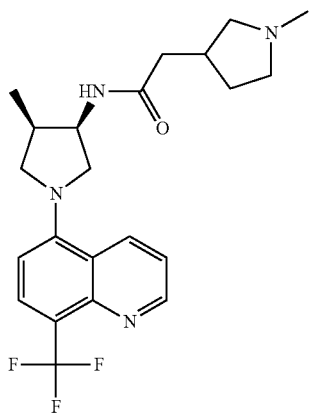<br>Isomer 2 |
| 23 | 8 | 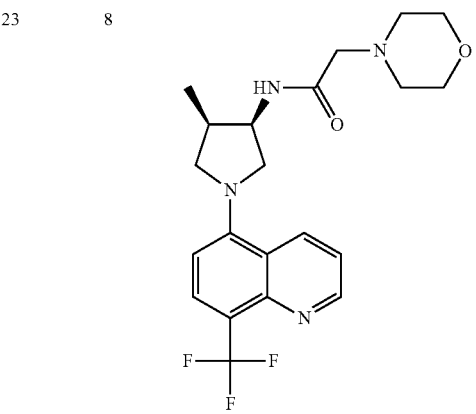 |
| 24 | 8 | 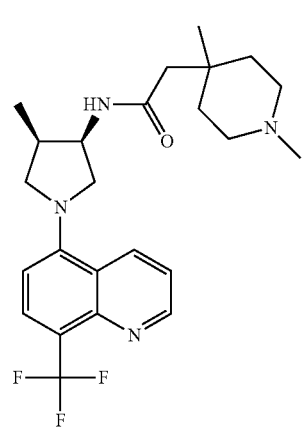 |
| 25 | 10 | 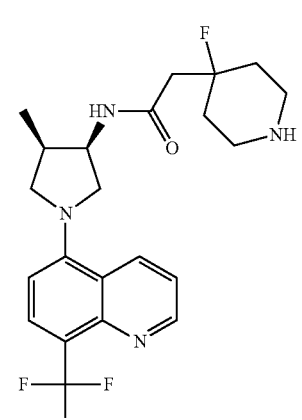 |

TABLE 1-continued
| Compound Number | Example Number | Chemical Structure |
|---|---|---|
| 26 | 11 | 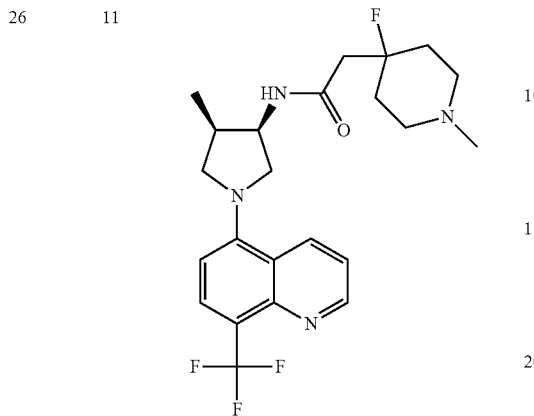 |
| 27 | 12 | 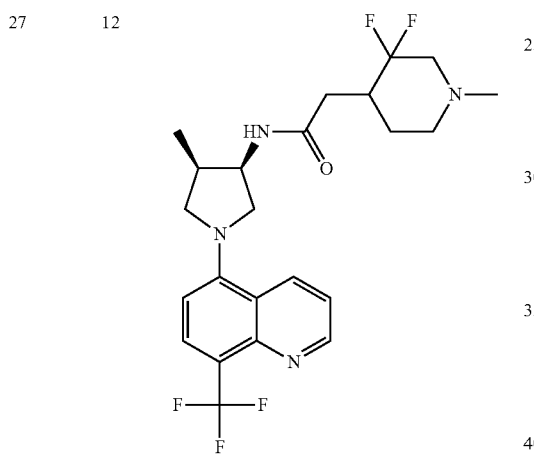  Isomer 1 |
| 28 | 12 | 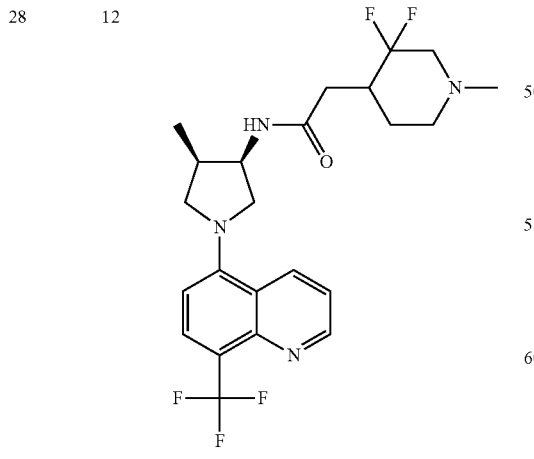  Isomer 2 |
TABLE 1-continued
| Compound Number | Example Number | Chemical Structure |
|---|---|---|
| 29 | 9 | 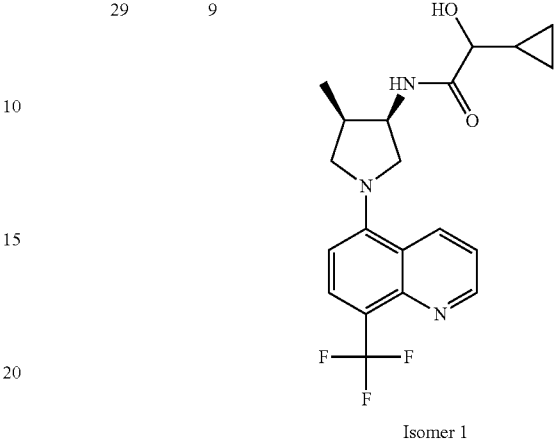  Isomer 1 |
| 30 | 9 | 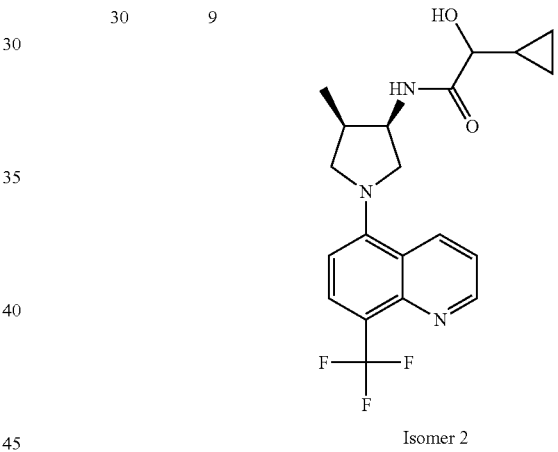  Isomer 2 |
| 31 | 8 | 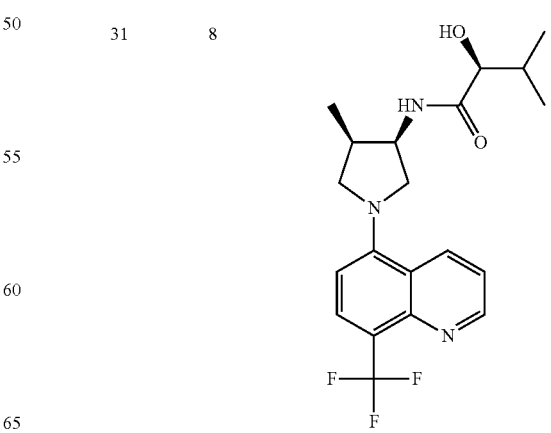 |

TABLE 1-continued
| Compound Number | Example Number | Chemical Structure |
|---|---|---|
| 32 | 8 | 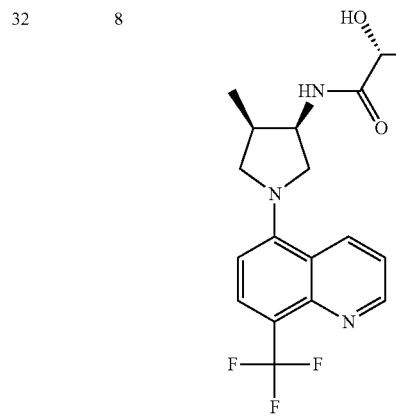 |
| 33 | 13 | 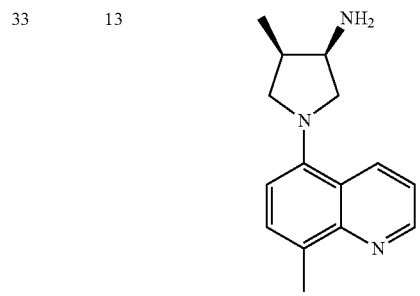 |
| 34 | 14 | 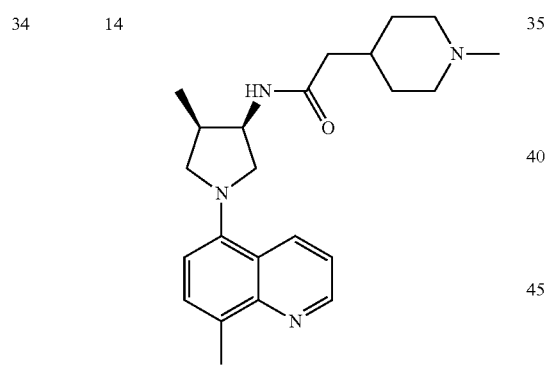 |
| 35 | 15 | 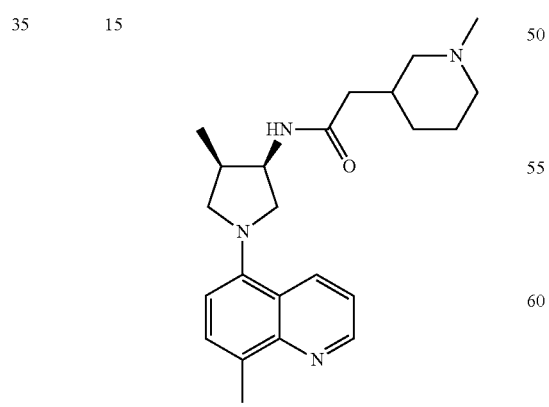<br>Isomer 1 |
TABLE 1-continued
| Compound Number | Example Number | Chemical Structure |
|---|---|---|
| 36 | 15 | 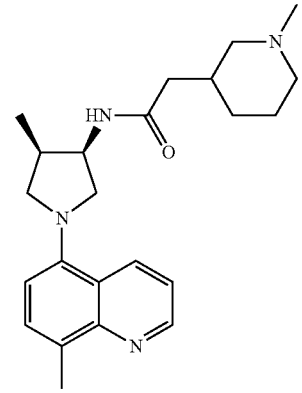<br>Isomer 2 |
| 37 | 15 | 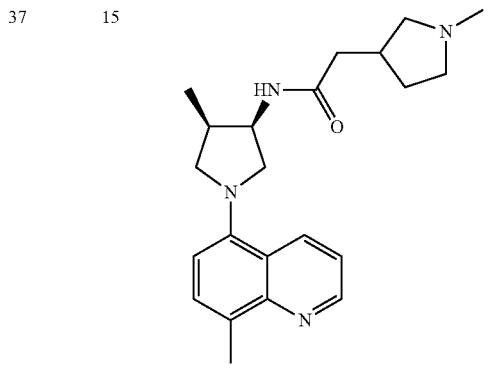<br>Isomer 1 |
| 38 | 15 | 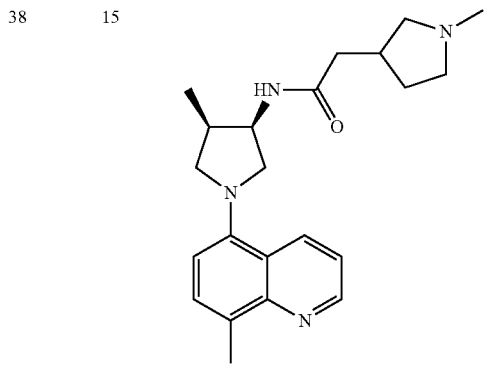<br>Isomer 2 |
| 39 | 14 | 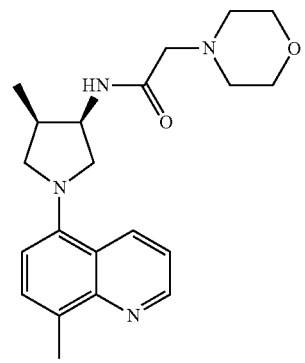 [SMILES: Cc1ccc(N2C[C@@H](C)[C@@H](NC(=O)CN3CCOCC3)C2)c2cccnc12] |

TABLE 1-continued

| Compound Number | Example Number | Chemical Structure |
|---|---|---|
| 40 | 14 | 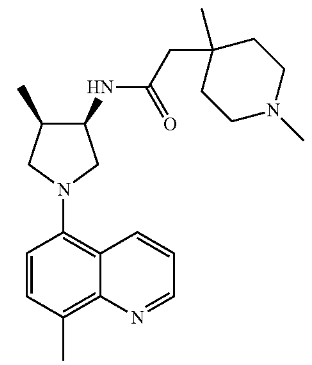 |
| 41 | 16 | 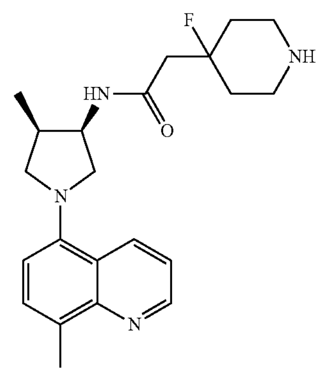 [SMILES: Cc1ccc(N2C[C@@H](C)[C@@H](NC(=O)CC3(F)CCNCC3)C2)c2cccnc12] |
| 42 | 17 | 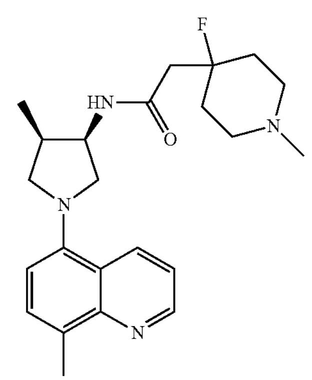 |
| 43 | 18 | Isomer 1 |
| 44 | 18 | Isomer 2 |
| 45 | 15 | Isomer 1 |
| 46 | 15 | Isomer 2 |

TABLE 1-continued

| Compound Number | Example Number | Chemical Structure |
|---|---|---|
| 47 | 14 | (structure: 8-methylquinolin-5-yl pyrrolidine with methyl substituent and (S)-2-hydroxy-3-methylbutanamide) |
| 48 | 14 | (structure: 8-methylquinolin-5-yl pyrrolidine with methyl substituent and (R)-2-hydroxy-3-methylbutanamide) |
| 49 | 19 | (structure: 3-amino-4-fluoropyrrolidin-1-yl with 8-(trifluoromethyl)quinolin-5-yl, cis Isomer 1) |
| 50 | 19 | (structure: 3-amino-4-fluoropyrrolidin-1-yl with 8-(trifluoromethyl)quinolin-5-yl, cis Isomer 2) |
| 51 | 20 | (structure: trans-3-amino-4-methylpyrrolidinyl attached to 8-methyl-1,7-naphthyridine) |
| 52 | 21 | (structure: methylpyrrolidine amide with 1-methylpiperidin-4-yl acetamide linked to 8-methyl-1,7-naphthyridine) |
| 53 | 21 | (structure: methylpyrrolidine amide with 1-methylazetidin-3-yl acetamide linked to 8-methyl-1,7-naphthyridine) |
| 54 | 22 | (structure: pyrrolidine-3-carboxamide with N-(2-(diethylamino)ethyl) linked to pyrido[2,3-b]pyrazine) |

TABLE 1-continued

| Compound Number | Example Number | Chemical Structure |
|---|---|---|
| 55 | 23 | 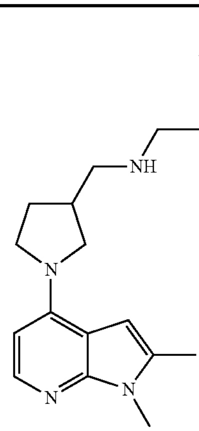 |
| 56 | 1 | 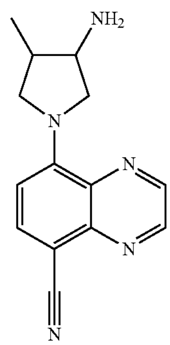 [SMILES: CC1CN(c2ccc(C#N)c3nccnc23)CC1N] |

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

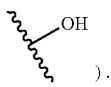

).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit TLR7/8, or a mutant thereof, in a biological sample or in a patient. In certain embodiments, the amount of compound in compositions of this invention is such that is effective to measurably inhibit TLR7/8, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this aremineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from a TLR7/8 related disorder, comprising administering to said subject an effective amount of a compound of formula I and related formulae.

The compounds of the present invention are useful as anticancer agents for cancers that are responsive to TLR7 activation. In certain embodiments, the cancers include, but are not limited to cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms tumor; leukemia, lymphoma, non-Hodgkins disease, chronic and acute myeloid leukaemia, acute lymphoblastic leukemia, Hodgkins disease, multiple myeloma and T-cell lymphoma; myelodysplastic syndrome, plasma cell neoplasia, paraneoplastic syndromes, cancers of unknown primary site and AIDS related malignancies.

In certain embodiments, the compounds of the invention are used to treat cancers of the skin or kidney. Sensitivity of a given cancer to activation of TLR7 can be assessed by, but not limited to measurement of a decrease in primary or metastatic tumor load (minor, partial or complete regression), alterations in the hemogram, altered hormone or cytokine concentrations in the blood, inhibition of further increase of tumor load, stabilization of the disease in the patient, assessment of biomarkers or surrogate markers relevant for the disease, prolonged overall survival of a patient, prolonged time to disease progression of a patient, prolonged progression-free survival of a patient, prolonged disease-free survival of a patient, improved quality of life of a patient, or modulation of the co-morbidity of the disease (for example, but not limited to pain, cachexia, mobilization, hopitalization, altered hemogram, weight loss, wound healing, fever).

The compounds according to the present invention may further be useful as immune response modifiers that can modulate the immune response in a number of different ways, rendering them useful in the treatment of a variety of disorders.

Provided herein are methods of inhibiting an immune response in an individual comprising administering to the individual an effective amount of an inhibitor of TLR7 and/or TLR8 (e.g., TLR inhibitor), using the compounds as described herein. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some variations, the TLR inhibitor inhibits a TLR7-dependent, a TLR8-dependent, and another TLR-dependent immune response. Unless otherwise noted, the term TLR inhibitor refers to any one of the TLR inhibitors disclosed herein. In some preferred embodiments, the individual is a human patient.

Methods of immunoregulation are provided by the present disclosure and include those that suppress and/or inhibit an immune response, including, but not limited to, an immune response. The present disclosure also provides methods for ameliorating symptoms associated with unwanted immune activation, including, but not limited to, symptoms associated with autoimmunity. Immune suppression and/or inhibition according to the methods described herein may be practiced on individuals including those suffering from a disorder associated with an unwanted activation of an immune response. The present disclosure also provides methods for inhibiting a TLR7 and/or TLR8 induced response (e.g., in vitro or in vivo). In some variations, the cell is contacted with the TLR inhibitor in an amount effective to inhibit a response from the cell that contributes to an immune response.

Inhibition of TLR7 and/or TLR8 are useful for treating and/or preventing a variety of diseases or disorders that are responsive to cytokines. Conditions for which TLR7 and/or TLR8 inhibitors may be used as treatments include, but are not limited to autoimmune diseases and inflammatory disorders. Provided herein are methods of treating or preventing a disease or disorder in an individual comprising administering to the individual an effective amount of an inhibitor of TLR7 and/or TLR8. Further, provided are methods for ameliorating symptoms associated with a disease or disorder comprising administering an effective amount of an inhibitor of TLR7 and/or TLR8 to an individual having the disease or disorder. Methods are also provided herein for preventing or delaying development of a disease or a disorder, comprising administering an effective amount of an inhibitor of one or more of TLR7 and/or TLR8 to an individual having the disease or the disorder. In certain embodiments, the inhibitor is a compound as described herein.

Provided herein are methods of inhibiting an immune response in an individual, the method comprising administering to the individual at least one TLR inhibitor as disclosed herein in an amount effective to inhibit the immune response in the individual. In some variations, the immune response is associated with an autoimmune disease. In further aspects, wherein inhibiting the immune response ameliorates one or more symptoms of the autoimmune disease. In still further aspects, wherein inhibiting the immune response treats the autoimmune disease. In yet further aspects, wherein inhibiting the immune response prevents or delays development of the autoimmune disease. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some aspects, at least one TLR inhibitor is administered in an amount effective to inhibit an immune response in the individual.

Provided herein are also methods of treating or preventing an autoimmune disease in an individual, comprising administering to the individual an effective amount of a TLR7 and/or TLR8 inhibitor. In some aspects, the autoimmune disease is characterized by joint pain, antinuclear antibody positivity, malar rash, or discoid rash. In some aspects, the autoimmune disease is associated with the skin, muscle tissue, and/or connective tissue. In some embodiments, the autoimmune disease is not evidenced in the individual by skin, muscle tissue, and/or connective tissue symptoms. In some embodiments, the autoimmune disease is systemic. Autoimmune diseases include, without limitation, rheumatoid arthritis (RA), autoimmune pancreatitis (AIP), systemic lupus erythematosus (SLE), type I diabetes mellitus, multiple sclerosis (MS), antiphospholipid syndrome (APS), sclerosing cholangitis, systemic onset arthritis, irritable bowel disease (IBD), scleroderma, Sjogren's disease, vitiligo, polymyositis, pemphigus vulgaris, pemphigus foliaceus, inflammatory bowel disease including Crohn's disease and ulcerative colitis, autoimmune hepatitis, hypopituitarism, graft-versus-host disease (GvHD), autoimmune skin diseases, uveitis, pernicious anemia, and hypoparathyroidism. Autoimmune diseases may also include, without limitation, polyangiitis overlap syndrome, Kawasaki's disease, sarcoidosis, glomerulonephritis, and cryopathies.

In some aspects, the autoimmune disease is selected from the group consisting of arthritis, pancreatitis, mixed connective tissue disease (MCTD), lupus, antiphospholipid syndrome (APS), systemic onset arthritis, and irritable bowel syndrome.

In other aspects, the autoimmune disease is selected from the group consisting of systemic lupus erythematosus (SLE), rheumatoid arthritis, autoimmune skin disease, and multiple sclerosis.

In other aspects, the autoimmune disease is selected from the group consisting of pancreatitis, glomerulonephritis, pyelitis, sclerosing cholangitis, and type I diabetes. In some aspects, the autoimmune disease is rheumatoid arthritis. In some aspects, the autoimmune disease is autoimmune pancreatitis (AIP). In some aspects, the autoimmune disease is glomerulonephritis. In some aspects, the autoimmune disease is pyelitis. In some aspects, the autoimmune disease is sclerosing cholangitis. In some aspects the autoimmune disorder is psoriasis. In some aspects, the autoimmune disease is a rheumatoid disease or disorder. In some aspects, the rheumatoid disease or disorder is rheumatoid arthritis. In some aspects, the disease is diabetes and/or diabetic-related disease or disorder. In some aspects, wherein the autoimmune disease is associated with RNA-containing immune complexes. In some aspects, the autoimmune disease is Sjogren's disease.

Provided herein are methods of inhibiting an immune response in an individual, the method comprising administering to the individual at least one TLR inhibitor as disclosed herein in an amount effective to inhibit the immune response in the individual. In some variations, the immune response is associated with an inflammatory disorder. As used herein, the term "inflammatory disorder" encompasses autoimmune diseases, as well as inflammatory conditions without a known autoimmune component (e.g., artherosclerosis, asthma, etc.). In further aspects, inhibiting the immune response ameliorates one or more symptoms of the inflammatory disorder. In still further aspects, inhibiting the immune response treats the inflammatory disorder. In yet further aspects, inhibiting the immune response prevents or delays development of the inflammatory disorder. In some aspects, the inflammatory disorder is selected from the group consisting of non-rheumatoid arthritis, kidney fibrosis, and liver fibrosis. In some aspects, the inflammatory disorder is an interface dermatitis. In some further aspects, the interface dermatitis is selected from the group consisting of lichen planus, lichenoid eruption, lichen planus-like keratosis, lichen striatus, keratosis lichenoides chronica, erythema multiforme, fixed drug eruption, pityriasis lichenoides, phototoxic dermatitis, radiation dermatitis, viral exanthems, dermatomyositis, secondary syphilis, lichen sclerosus et atrophicus, mycosis fungoides, bullous pemphigoid, lichen aureus, porokeratosis, acrodermatitis chronicus atrophicans, and regressing melanoma. In some aspects, the inflammatory condition is a skin disorder such as atopic dermatitis (eczema). In some aspects, the inflammatory disorder is a sterile inflammatory condition such as drug-induced liver and/or pancreas inflammation. In some further aspects, the inflammatory disease is an inflammatory liver disorder. In some other further aspects, the inflammatory disease is an inflammatory pancreatic disorder.

Provided herein are methods of inhibiting an immune response in an individual, the method comprising administering to the individual at least one TLR inhibitor as disclosed herein in an amount effective to inhibit the immune response in the individual. In some variations, the immune response is associated with chronic pathogen stimulation. In some variations, the immune response is associated with infection by HIV. In further aspects, wherein inhibiting the immune response ameliorates one or more symptoms of the viral disease or disorder resulting from infection by HIV. In still further aspects, wherein inhibiting the immune response treats the viral disease or disorder resulting from infection by HIV. In yet further aspects, wherein inhibiting the immune response prevents or delays development of the viral disease or disorder resulting from infection by HIV. Other variations provided herein relate to immunoinhibitory therapy of individuals having been exposed to or infected with HIV. Administration of a TLR inhibitor to an individual having been exposed to or infected with HIV results in suppression of HIV induced cytokine production. In some aspects, at least one TLR inhibitor is administered in an amount effective to suppress HIV induced cytokine production in an individual exposed to or infected with a HIV.

Provided herein are methods for inhibiting a TLR7 and/or TLR8-dependent immune response in an individual, the method comprising administering to the individual a TLR inhibitor in an amount effective to inhibit the immune response in the individual. In some variations, the immune response is associated with an autoimmune disease. In some aspects, the autoimmune disease is rheumatoid arthritis. In some aspects, the TLR inhibitor is effective in suppressing one or more symptoms of rheumatoid arthritis. In some aspects, the autoimmune disease is multiple sclerosis. In some aspects, the TLR inhibitor is effective in suppressing one or more symptoms of multiple sclerosis. In some aspects, the autoimmune disease is lupus. In some aspects, the TLR inhibitor is effective in suppressing one or more symptoms of lupus. In some aspects, the autoimmune disease is pancreatitis. In some aspects, the TLR inhibitor is effective in suppressing one or more symptoms of pancreatitis. In some aspects, the autoimmune disease is diabetes. In some aspects, the TLR inhibitor is effective in suppressing one or more symptoms of diabetes. In some aspects, the disease is Sjogren's disease. In some aspects, the TLR inhibitor is effective in suppressing one or more symptoms of Sjogren's disease. In some variations, the immune response is associated with an inflammatory disorder. In some aspects, the TLR inhibitor is effective in suppressing one or more symptoms of an inflammatory disorder. In some variations, the immune response is associated with chronic pathogen stimulation. In some aspects, the TLR inhibitor is effective in suppressing one or more symptoms of chronic pathogen stimulation. In some variations, the immune response is associated with viral disease resulting from infection with HIV. In some aspects, the TLR inhibitor is effective in suppressing one or more symptoms of viral disease resulting from infection with HIV. In any variation, the TLR inhibitor is a polynucleotide comprising an inhibitory motif for one or more of TLR7, TLR8, and TLR9.

In some embodiments of any of the methods involving administration of a TLR inhibitor to an individual (e.g., methods of inhibiting an immune response, treating or preventing an autoimmune disease or inflammatory disorder, etc.) the TLR inhibitor has a therapeutically acceptable safety profile. The TLR inhibitor may for example, have a therapeutically acceptable histological profile including an acceptably low, if any, toxicity of the liver, kidney, pancreas, or other organs. On occasion, polynucleotides have been associated with toxicity to certain organs such as the liver, kidney and pancreas. In some embodiments, the TLR inhibitor has a safety profile that is unexpected and advantageous. In some embodiments, a safety profile includes evaluation of toxicity, histological profile, and/or necrosis (e.g., liver, kidneys and/or heart). In some embodiments, the TLR inhibitor has a therapeutically acceptable level of toxicity. In some embodiments, the TLR inhibitor has a reduced level of toxicity as compared to another TLR inhibitor. In some embodiments, the TLR inhibitor induces a therapeutically acceptable reduction in body weight as compared to the initial body weight of a treated individual. In some embodiments, the TLR inhibitor induces less than 5%, 7.5%, 10%, 12.5, or 15% reduction in total body weight. In some embodiments, the TLR inhibitor has a therapeutically acceptable histology profile. In some embodiments, the TLR inhibitor has a better (e.g., lower severity score) histology profile, for example, as compared to a reference TLR inhibitor. In some embodiments, the TLR inhibitor has a better (e.g., lower severity score) histology profile upon evaluation of the liver, kidneys and/or heart, for example. In some embodiments, the TLR inhibitor has a therapeutically acceptable necrosis score. In some embodiments, the TLR inhibitor has reduced necrosis and/or better (e.g., lower) necrosis score, for example, as compared to a reference TLR inhibitor. In some embodiments, the TLR inhibitor has reduced renal and/or hepatocellular necrosis and/or a better renal and/or hepatocellular necrosis score, for example, as compared to a reference TLR inhibitor.

Accordingly, the invention provides a method of activating TLR7 in an animal, especially a mammal, preferably a human comprising administering an effective amount of a compound of Formula I to the animal. As with all compositions for inhibition of an immune response, the effective amounts and method of administration of the particular TLR inhibitor formulation can vary based on the individual, what condition is to be treated and other factors evident to one skilled in the art. An effective amount of a compound will vary according to factors known in the art but is expected to be a dose of about 0.1 to 10 mg/kg, 0.5 to 10 mg/kg, 1 to 10 mg/kg, 0.1 to 20 mg/kg, 0.1 to 20 mg/kg, or 1 to 20 mg/kg.

The invention also provides a method of treating a viral infection in an animal comprising administering an effective amount of a compound of Formula I to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose as indicated above with respect to the activation of TLR7, or a dose of about 100 ng/kg to about 50 mg/kg, preferably about 10 rig/kg to about 5 mg/kg.

In various embodiments, compounds of formula (I), and related formulae exhibit a IC50 for the binding to TLR7/8 of less than about 5 µM, preferably less than about 1 µM and even more preferably less than about 0.100 µM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit TLR7/8 activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing TLR7/8-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of TLR7/8 activity if expedient.

The invention also relates to the use of compounds according to formula (I) and/or physiologically acceptable salts thereof for the prophylactic or therapeutic treatment and/or monitoring of diseases that are caused, mediated and/or propagated by TLR7/8 activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by TLR7/8 activity. In certain embodiments, the invention provides the use of a compound according to formula I or physiologically acceptable salts thereof, for the production of a medicament for the prophylactic or therapeutic treatment of a TLR7/8-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with TLR7/8 activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with TLR7/8 activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The TLR inhibitors of the present disclosure can be administered in combination with one or more additional therapeutic agents. As described herein, the TLR inhibitors can be combined with a physiologically acceptable carrier. The methods described herein may be practiced in combination with other therapies that make up the standard of care for the disorder, such as administration of anti-inflammatory agents.

In some embodiments, a TLR inhibitor as described herein is administered in combination with a corticosteroid. In some embodiments, the corticosteroid is a glucocorticosteroid. In some embodiments, the corticosteroid is a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof, hydrocortisone and derivatives, prodrugs, isomers and analogs thereof (i.e., cortisol or Cortef), hydrocortisone and derivatives, prodrugs, isomers and analogs thereof, betamethasone and derivatives, prodrugs, isomers and analogs thereof (i.e., Celestone), budesonide and derivatives, prodrugs, isomers and analogs thereof (i.e., Entocort EC), methylprednisolone and derivatives, prodrugs, isomers and analogs thereof (i.e., Medrol), prednisolone and derivatives, prodrugs, isomers and analogs thereof (i.e., Deltasone, Crtan, Meticorten, Orasone, or Sterapred), triamcinolone and derivatives, prodrugs, isomers and analogs thereof (i.e., Kenacort or Kenalog), and the like. In some embodiments, the corticosteroid is fludrocortisone or a derivative, prodrug, isomer or analog thereof. In some embodiments, the corticosteroid is fludrocortisone. In some embodiments, the corticosteroid is hydroxycortisone or a derivative, prodrug, isomer or analog thereof. In some embodiments, the corticosteroid is hydroxycortisone.

In some embodiments, the corticosteroid is administered between about any of 0.001 mg to 1 mg, 0.5 mg to 1 mg, 1 mg to 2 mg, 2 mg to 20 mg, 20 mg to 40 mg, 40 to 80 mg, 80 to 120 mg, 120 mg to 200 mg, 200 mg to 500 mg, or 500 mg to 1000 mg per day. In some embodiments, the corticosteroid is administered between about any of 0.1 mg/kg to 0.5 mg/kg, 0.5 mg/kg to 1 mg/kg, 1 mg/kg to 2 mg/kg, 2 mg/kg to 5 mg/kg, 5 mg/kg to 10 mg/kg, 10 mg/kg to 15 mg/kg, 15 mg/kg to 20 mg/kg, 20 mg/kg to 25 mg/kg, 25 mg/kg to 35 mg/kg, or 35 mg/kg to 50 mg/kg per day.

In some embodiments, the TLR inhibitor used in combination therapy, given in amounts of the TLR inhibitor delivered, may be, for example, from about any of 0.1 to 10 mg/kg, 0.5 to 10 mg/kg, 1 to 10 mg/kg, 0.1 to 20 mg/kg, 0.1 to 20 mg/kg, or 1 to 20 mg/kg.

In some embodiments, the TLR inhibitor is administered simultaneously with one or more additional therapeutic agents including, but not limited to, a corticosteroid (simultaneous administration). In some embodiments, the TLR inhibitor is administered sequentially with an additional therapeutic agent including, but not limited to, a corticosteroid (sequential administration). In some embodiments, sequential administration includes administering the TLR inhibitor or additional therapeutic agent followed within about any of one minutes, five minutes, 30 minutes, one hour, five hours, 24 hours, 48 hours, or a week. In some embodiments, the TLR inhibitor is administered by the same route of administration as the additional therapeutic agent. In some embodiments, the TLR inhibitor is administered by a different route of administration than the additional therapeutic agent. In some embodiments, the additional therapeutic agent is administered parentally (e.g., central venous line, intra-arterial, intravenous, intramuscular, intraperitoneal, intradermal, or subcutaneous injection), orally, gastrointestinally, topically, naso-pharyngeal and pulmonary (e.g. inhalation or intranasally). In some embodiments, the additional therapeutic agent is a corticosteroid.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustinel[13];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamidel[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab, tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1]Prop. INN (Proposed International Nonproprietary Name);
[2]Rec. INN (Recommended International Nonproprietary Names);
[3]USAN (United States Adopted Name);
[4] no INN).

In some embodiments, the combination of a TLR inhibitor with one or more additional therapeutic agents reduces the effective amount (including, but not limited to, dosage volume, dosage concentration, and/or total drug dose administered) of the TLR inhibitor and/or the one or more additional therapeutic agents administered to achieve the same result as compared to the effective amount administered when the TLR inhibitor or the additional therapeutic agent is administered alone. In some embodiments, the combination of a TLR inhibitor with a corticosteroid reduces the effective amount of corticosteroid administered as compared to the corticosteroid administered alone. In some embodiments, the combination of a TLR inhibitor with the additional therapeutic agents reduces the frequency of administrations of the therapeutic agent compared to administration of the additional therapeutic agent alone. In some embodiments, the combination of a TLR inhibitor with the additional therapeutic agent reduces the total duration of treatment compared to administration of the additional therapeutic agent alone. In some embodiments, the combination of a TLR inhibitor with the additional therapeutic agent reduces the side effects associated with administration of the additional therapeutic agent alone. In some embodiments, the additional therapeutic agent is a corticosteroid. In some embodiments, the corticosteroid is fludrocortisone or a derivative, prodrug, isomer or analog thereof. In some embodiments, the corticosteroid is fludrocortisone. In some embodiments, the combination of an effective amount of the TLR inhibitor with the additional therapeutic agent is more efficacious compared to an effective amount of the TLR inhibitor or the additional therapeutic agent alone.

TLR inhibitors also may be useful as a vaccine adjuvant for use in conjunction with any material that modulates either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like. In some aspects, the combination therapy including but not limited to the combination of a TLR inhibitor and a vaccine is used in the treatment of an autoimmune disease or an inflammatory disorder. In some aspects, the combination therapy including but not limited to the combination of a TLR inhibitor and a vaccine is used in the treatment of an infectious disease.

In some embodiments, the combination therapy including but not limited to the combination of a TLR inhibitor and a corticosteroid is used in the treatment of an autoimmune disease or an inflammatory disorder. In some embodiments, the autoimmune disease is selected from but not limited to rheumatoid arthritis, systemic lupus erythematosus, autoimmune skin disease, multiple sclerosis, pancreatitis, glomerulonephritis, pyelitis, Sclerosing cholangitis, and type I diabetes. In some embodiments, the autoimmune disease is Sjogren's disease.

Also provided herein are kits comprising a TLR inhibitor as provided herein, and instructions for use in the methods of inhibiting a TLR7- and/or TLR8-dependent immune response.

The kits may comprise one or more containers comprising a TLR inhibitor (or a formulation comprising a TLR inhibitor) as described herein, and a set of instructions, generally written instructions although electronic storage media (e.g., magnetic diskette or optical disk) containing instructions are also acceptable, relating to the use and dosage of the TLR inhibitor or formulation for the intended treatment (e.g., suppression of a response to a TLR7 and/or TLR8 agonists, suppression of a TLR7 and/or TLR8-dependent immune response, ameliorating one or more symptoms of an autoimmune disease, ameliorating a symptom of chronic inflammatory disease, decreasing cytokine production in response to a virus, and/or treating and/or preventing one or more symptoms of a disease or disorder mediated by TLR7 and/or TLR8). The instructions included with the kit generally include information as to dosage, dosing schedule, and route of administration for the intended treatment. The containers for the TLR inhibitor (or formulations comprising a TLR inhibitor) may be unit doses, bulk packages (e.g., multi-dose packages) or sub-unit doses. The kits may further comprise a container comprising an adjuvant.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting TLR7/8 activity in a biological sample comprising the step of contacting said biological sample with a compound of this invention, or a composition comprising said compound.

According to another embodiment, the invention relates to a method of inhibiting TLR7/8, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of TLR7/8, including the evaluation of the many factors thought to influence, and be influenced by, the production of TLR7/8 and the interaction of TLR7/8. The present compounds are also useful in the development of other compounds that interact with TLR7/8 since the present compounds provide important structure-activity relationship (SAR) information that facilitate that development. Compounds of the present invention that bind to TLR7/8 can be used as reagents for detecting TLR7/8 in living cells, fixed cells, in biological fluids, in tissue homogenates, in purified, natural biological materials, etc. For example, by labeling such compounds, one can identify cells expressing TLR7/8. In addition, based on their ability to bind TLR7/8, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing TLR7/8 inside permeabilized cells. The compounds of the invention can also be utilized as commercial research reagents for various medical research and diagnostic uses. Such uses can include but are not limited to: use as a calibration standard for quantifying the activities of candidate TLR7/8 inhibitors in a variety of functional assays; use as blocking reagents in random compound screening, i.e. in looking for new families of TLR7/8 ligands, the compounds can be used to block recovery of the presently claimed TLR7/8 compounds; use in the co-crystallization with TLR7/8, i.e. the compounds of the present invention will allow formation of crystals of the compound bound to TLR7/8, enabling the determination of enzyme/compound structure by x-ray crystallography; other research and diagnostic applications, wherein TLR7/8 is preferably activated or such activation is conveniently calibrated against a known quantity of an TLR7/8 inhibitor, etc.; use in assays as probes for determining the expression of TLR7/8 in cells; and developing assays for detecting compounds which bind to the same site as the TLR7/8 binding ligands.

The compounds of the invention can be applied either themselves and/or in combination with physical measurements for diagnostics of treatment effectiveness. Pharmaceutical compositions containing said compounds and the use of said compounds to treat TLR7/8-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of TLR7/8, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All solvents used were commercially available and were used without further purification. Reactions were typically run using anhydrous solvents under an inert atmosphere of nitrogen. Flash column chromatography was generally carried out using Silica gel 60 (0.035-0.070 mm particle size).

All NMR experiments were recorded either on Bruker Mercury Plus 400 NMR Spectrometer equipped with a Bruker 400 BBFO probe at 400 MHz for proton NMR or on Bruker Mercury Plus 300 NMR Spectrometer equipped with a Bruker 300 BBFO probe at 300 MHz for proton NMR, or on Bruker Avance III 400 NMR Spectrometer equipped with a Bruker PABBO BB-1H/D Z GRD probe at 400 MHz for proton NMR. All deuterated solvents contained typically 0.03% to 0.05% v/v tetramethylsilane, which was used as the reference signal (set at δ 0.00 for both $^1H$ and $^{13}C$). In cases where the deuterated solvents did not contain tetramethylsilane, the residual non-deuterated solvent peaks were used as a reference signal, as per published guidelines (J. Org. Chem., Vol. 62, No. 21, 1997).

LC-MS analyses were performed one either one of the two following instruments:

SHIMADZU LC-MS machine consisting of an UFLC 20-AD system and LCMS 2020 MS detector. The column used was a Shim-pack XR-ODS, 2.2 µm, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

Agilent 1200 Series mass spectrometers from Agilent Technologies, using either Atmospheric Chemical Ionization (APCI) or Electrospray Ionization (ESI). Diode Array detector was scanned from 200-400 nm. The mass spectrometer was scanned between m/z 90-900 with a scan time of 0.6 s. Column: XBridge C8, 3.5 µm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B or a LC/MS Waters ZMD (ESI).

HPLC data were either obtained from the SHIMAZU LC-MS machine or using Agilent 1100 series HPLC from Agilent technologies using a column (XBridge C8, 3.5 µm, 4.6×50 mm) and two mobile phases (mobile phase A: water+0.1% TFA; mobile phase B: ACN+0.1% TFA). The flow rate was 2 ml/min. The gradient method was: 0 min: 5% B; 8 min: 100% B; 8.1 min: 100% B; 8.5 min: 5% B; 10 min 5% B, unless otherwise indicated.

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, $3^{rd}$ Edition 1999.

Intermediate 1: 8-bromoquinoxaline-5-carbonitrile

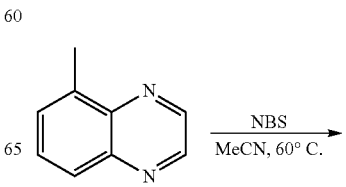

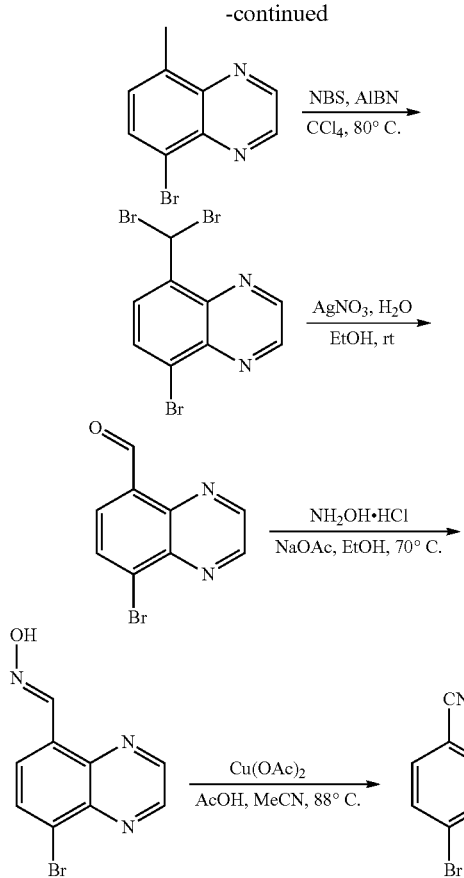

5-Bromo-8-methylquinoxaline

To a solution of 5-methylquinoxaline (9.50 g, 66.0 mmol) in acetonitrile (80 mL) was added 1-bromopyrrolidine-2,5-dione (27.0 g, 151.7 mmol) at room temperature. The resulting solution was stirred for 16 h at 60° C. After cooling to room temperature, the reaction mixture was concentrated under reduced pressure and the residue was diluted with ethyl acetate (500 mL). The insoluble solids in the mixture were filtered out and the filtrate was washed with brine and dried over $Na_2SO_4$. The solvent was removed under reduced pressure to yield 5-bromo-8-methylquinoxaline as brown solid (6.00 g, 41%). MS: m/z=222.9 $[M+H]^+$.

5-Bromo-8-(dibromomethyl)quinoxaline

To a solution of 5-bromo-8-methylquinoxaline (6.00 g, 27.0 mmol) in $CCl_4$ (200 mL) was added NBS (19.2 g, 108.1 mmol) and AIBN (0.71 g, 4.3 mmol) at room temperature. The resulting solution was then stirred for 16 h at 80° C. After cooling to room temperature, the reaction mixture was concentrated under reduced pressure and the residue was diluted with ethyl acetate (500 mL). The insoluble solids in the mixture were filtered out, and then the filtrate was washed with brine and dried over $Na_2SO_4$. The solvent was removed under reduced pressure and the residue was purified by flash chromatography eluting with EtOAc in petroleum ether (0% to 5% gradient) to yield 5-bromo-8-(dibromomethyl)quinoxaline as light yellow solid (7.15 g, 70%). MS: m/z=378.7 $[M+H]^+$.

8-Bromoquinoxaline-5-carbaldehyde

To a solution of 5-bromo-8-(dibromomethyl)quinoxaline (13.5 g, 35.7 mmol) in ethanol (290 mL) was added a solution of AgNO3 (24.3 g, 142.9 mmol) in water (90 mL) dropwise at room temperature. The resulting mixture was then stirred for 1 h at room temperature. When the reaction was done, the reaction mixture was diluted with acetonitrile (300 mL) and precipitation happened. The precipitates were filtered out and the filtrate was concentrated under reduced pressure to yield 8-bromoquinoxaline-5-carbaldehyde as yellow solid (10.0 g, crude). MS: m/z=236.8 $[M+H]^+$.

(E)-8-Bromoquinoxaline-5-carbaldehyde Oxime

To a solution of 8-bromoquinoxaline-5-carbaldehyde (10 g, crude) in ethanol (100 mL) was added NaOAc (6.34 g, 73.4 mmol) and $NH_2OH \cdot HCl$ (3.12 g, 42.7 mmol) at room temperature. The resulting mixture was stirred for 3 h at 70° C. When the reaction was done, the insoluble solids in the reaction mixture were filtered out at 70° C., and then the filtrate was cooled to 0° C. and precipitation happened. The precipitates were collected by filtration and dried in oven to yield (E)-N-[(8-bromoquinoxalin-5-yl)methylidene]hydroxylamine as yellow solid (2.96 g, 33% for 2 steps). MS: m/z=253.9 $[M+H]^+$.

8-Bromoquinoxaline-5-carbonitrile

To a solution of (E)-N-[(8-bromoquinoxalin-5-yl)methylidene]hydroxylamine (3.47 g, 13.8 mmol) in acetonitrile (20 mL) was added $Cu(OAc)_2$ (577 mg, 3.18 mmol) and acetic acid (1.24 g, 20.7 mmol) at room temperature. The resulting mixture was stirred for 15 h at 88° C. After cooling to room temperature, the reaction mixture was diluted with acetonitrile (10 mL). The insoluble solids in the mixture were filtered out and the filtrate was concentrated under reduced pressure. The residue was purified by flash chromatography eluting with EtOAc in petroleum ether (0% to 15% gradient) to yield 8-bromoquinoxaline-5-carbonitrile as yellow solid (1.22 g, 38%). MS: m/z=235.8 $[M+H]^+$.

Intermediate 2: 5-bromo-8-methyl-[1,7]naphthyridine

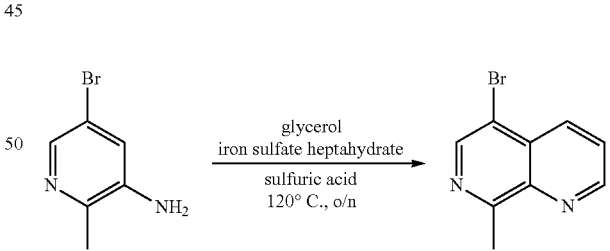

5-bromo-8-methyl-[1,7]naphthyridine

To a mixture of 5-bromo-2-methyl-pyridin-3-ylamine (3.00 g; 16.0 mmol), glycerol (4.7 mL; 64.1 mmol), iron(II) sulfate heptahydrate (892 mg; 3.2 mmol) was added sulfuric acid (5.6 mL; 96.2 mmol) dropwise. The resulting mixture was heated at 120° C. overnight. The reaction mixture was treated with ice, a solution 2N of sodium hydroxide, ethyl acetate and dichloromethane. After filteration to remove the dark brown solid solids, the organic layer was separated and washed with brine, dried and concentrated. The crude was purified by chromatography on silica gel, eluting with ethyla acetate and hexanes, to afford 5-bromo-8-methyl-[1,7]naphthyridine (470 mg, 13%). MS: m/z=224 [M+H]⁺.

Intermediate 3: 8-chloropyrido[2,3-b]pyrazine

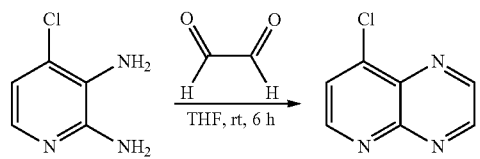

8-chloropyrido[2,3-b]pyrazine

To a solution of 4-chloropyridine-2,3-diamine (1.90 g, 13.20 mmol) in THF (100 mL) was added oxaldehyde (1.00 g, 17.20 mmol) at room temperature. The resulting solution was then stirred for 6 h at room temperature. When the reaction was done, the reaction mixture was concentrated under reduced pressure and the residue was purified by flash chromatography eluting with EtOAc in petroleum ether (0% to 50% gradient) to yield 8-chloropyrido[2,3-b]pyrazine as yellow solid (2.10 g, 91%). MS: m/z=166.1 [M+H]⁺.

Intermediate 4: 4-bromo-1,2-dimethyl-1H-pyrrolo[2,3-b]pyridine

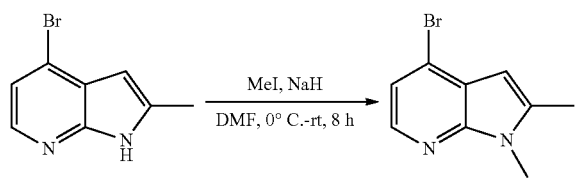

4-bromo-1,2-dimethyl-1H-pyrrolo[2,3-b]pyridine

At 0° C., to a solution of 4-bromo-2-methyl-1H-pyrrolo[2,3-b]pyridine (6.00 g, 27.0 mmol) in N,N-dimethylformamide (60 mL) was added sodium hydride (1.62 g, 40.5 mmol). The reaction was stirred at 0° C. for 15 min, then iodomethane (2.1 mL, 32.4 mmol) was added and the resulting mixture was stirred at room temperature for 8 h. When the reaction was done, the reaction mixture was quenched with water (250 mL) and the resulting mixture was extracted with ethyl acetate (3×100 mL). The combined organic phase was washed with brine, dried over anhydrous sodium sulfate, filtered and concentrated under reduced pressure. The residual gum was triturated with hexane (40 mL) and dried to yield 4-bromo-1,2-dimethyl-1H-pyrrolo[2,3-b]pyridine as a brown semi-solid (3.80 g, 62%). MS: m/z=227 [M+H]⁺.

Example 1: Synthesis of compound 1 (8-[(3R,4R)-3-amino-4-methylpyrrolidin-1-yl]quinoxaline-5-carbonitrile)

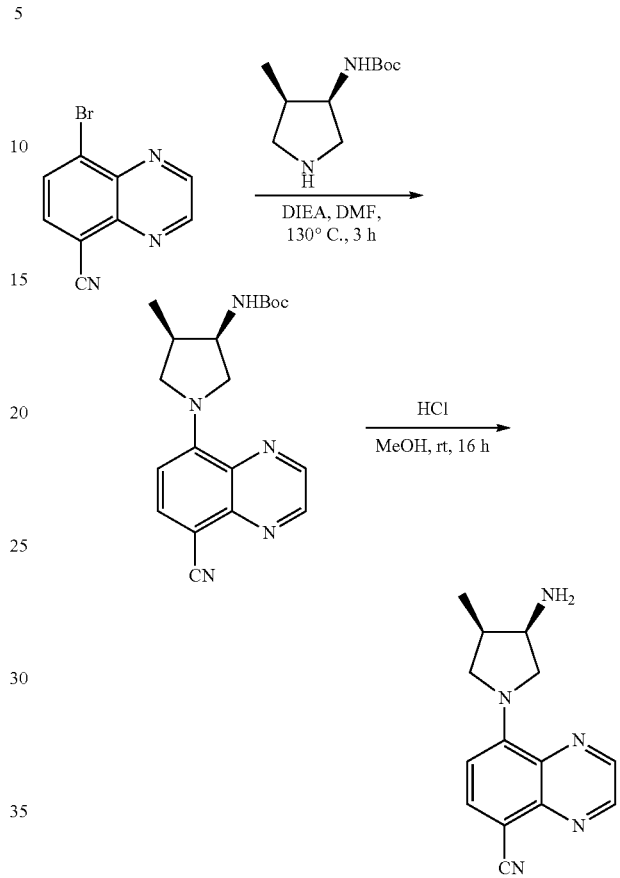

tert-butyl N-[(3R,4R)-1-(8-cyanoquinoxalin-5-yl)-4-methylpyrrolidin-3-yl]carbamate To a solution of 8-bromoquinoxaline-5-carbonitrile (900 mg, 3.85 mmol) and tert-butyl N-[(3R,4R)-4-methylpyrrolidin-3-yl]carbamate (808 mg, 4.03 mmol) in N,N-dimethylformamide (7 mL), was added DIEA (1.58 g, 12.20 mmol) at room temperature. The reaction solution was stirred for 3 hours at 130° C. When the reaction was done, it was quenched by the addition of water (30 mL). The resulting mixture was extracted with ethyl acetate (50 mL×3). The organic phases were combined, washed with brine and dried over Na₂SO₄. The solvent was removed under reduced pressure to yield tert-butyl N-[(3R,4R)-1-(8-cyanoquinoxalin-5-yl)-4-methylpyrrolidin-3-yl]carbamate as yellow solid (1.19 g, 44%). MS: m/z=354.1 [M+H]⁺.

8-[(3R,4R)-3-amino-4-methylpyrrolidin-1-yl]quinoxaline-5-

To a solution of tert-butyl N-[(3R,4R)-1-(8-cyanoquinoxalin-5-yl)-4-methylpyrrolidin-3-yl]carbamate (720 mg, 2.04 mmol) in MeOH was added hydrogen chloride solution (12 N, 6 mL, 72 mmol) at room temperature. The resulting mixture was stirred for 6 hours at room temperature. When the reaction was done, the reaction mixture was concentrated under reduced pressure and the residue was purified by prep-HPLC under the following conditions: column, XBridge Prep C18 OBD column, 250 mm, 5 um, 13 nm; mobile phase, acetonitrile in water (with 0.05% NH$_3$.H$_2$O), 29% to 42% gradient in 8 min; detector, UV 254 nm. 8-[(3R,4R)-3-amino-4-methylpyrrolidin-1-yl]quinoxaline-5-carbonitrile was obtained as white solid (490 mg, 95%).

Compound 1

HPLC: 98.1% purity, RT=1.05 min. MS: m/z=254.3 [M+H]$^+$. $^1$H NMR (400 MHz, Methanol-d$_4$, ppm) δ 8.79 (d, J=1.8 Hz, 1H), 8.73 (d, J=1.8 Hz, 1H), 7.97-7.89 (m, 1H), 6.72 (d, J=8.8 Hz, 1H), 4.21-4.12 (m, 1H), 4.05-3.95 (m, 1H), 3.93-3.85 (m, 1H), 3.79-3.69 (m, 1H), 3.63-3.52 (m, 1H), 2.53-2.38 (m, 1H), 1.16 (d, J=7.0 Hz, 3H).

The following compound was synthesized in an analogous manner:

Compound 56 8-(3-Amino-4-methyl-pyrrolidin-1-yl)-quinoxaline-5-carbonitrile hydrochloride From 8-bromoquinoxaline-5-carbonitrile and (4-Methyl-pyrrolidin-3-yl)-carbamic acid tert-butyl ester. HPLC: 92% purity, RT=1.50 min. MS: m/z=254 [M+H]$^+$.

Example 2: Synthesis of Compound 2 (N-[(3R,4R)-1-(8-cyanoquinoxalin-5-yl)-4-methylpyrrolidin-3-yl]-2-(1-methylpiperidin-4-yl)acetamide)

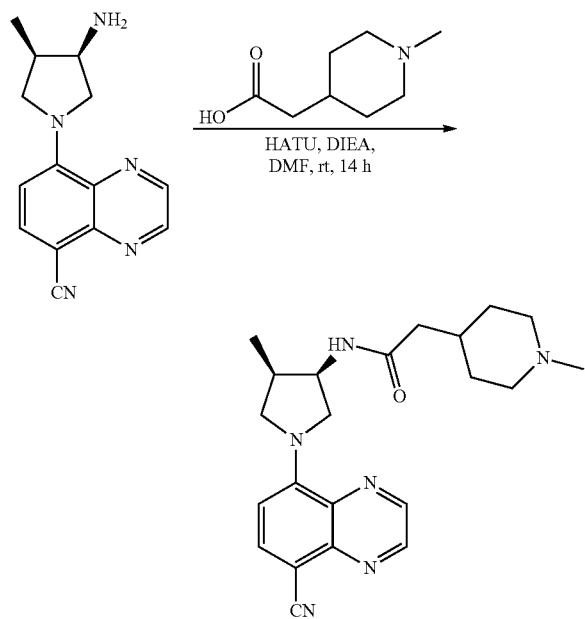

N-[(3R,4R)-1-(8-cyanoquinoxalin-5-yl)-4-methyl-pyrrolidin-3-yl]-2-(1-methylpiperidin-4-yl)acetamide To a solution of 8-[(3R,4R)-3-amino-4-methylpyrrolidin-1-yl]quinoxaline-5-carbonitrile (48 mg, 0.19 mmol) in N,N-dimethylformamide (10 mL), were added 2-(1-methylpiperidin-4-yl)acetic acid (59 mg, 0.38 mmol), DIEA (145 mg, 1.13 mmol) and HATU (143 mg, 0.38 mmol) at room temperature. The resulting solution was stirred for 14 hours at room temperature. When the reaction was done, the solvent was removed under reduced pressure and the residue was purified by prep-HPLC under the following conditions: column, XBridge Shield RP18 OBD column, 150 mm, 5 um, 13 nm; mobile phase, acetonitrile in water (with 10 mM NH$_4$HCO$_3$), 13% to 40% gradient in 8 min; detector, UV 254 nm. N-[(3R,4R)-1-(8-cyanoquinoxalin-5-yl)-4-methyl-pyrrolidin-3-yl]-2-(1-methylpiperidin-4-yl)acetamide was obtained as yellow solid (18 mg, 25%).

Compound 2

HPLC: 92.4% purity, RT=3.85 min. MS: m/z=393.4 [M+H]$^+$. $^1$H NMR (400 MHz, Methanol-d$_4$, ppm) δ 8.81 (d, J=1.8 Hz, 1H), 8.75 (d, J=1.8 Hz, 1H), 7.95 (d, J=8.7 Hz, 1H), 6.75 (d, J=8.7 Hz, 1H), 4.64-4.56 (m, 1H), 4.31-4.21 (m, 1H), 4.08-3.92 (m, 2H), 3.74-3.64 (m, 1H), 2.89-2.78 (m, 2H), 2.69-2.54 (m, 1H), 2.29-2.09 (m, 5H), 2.06-1.94 (m, 2H), 1.83-1.62 (m, 3H), 1.37-1.20 (m, 2H), 1.10 (d, J=6.8 Hz, 3H).

The following compounds were synthesized in an analogous manner:

Compound 7 (N-[(3R,4R)-1-(8-cyanoquinoxalin-5-yl)-4-methylpyrrolidin-3-yl]-2-(morpholin-4-yl)acetamide)

From 8-[(3R,4R)-3-amino-4-methylpyrrolidin-1-yl]quinoxaline-5-carbonitrile and 2-(morpholin-4-yl)acetic acid, purified by prep-HPLC under the following conditions: column, XBridge Prep C18 OBD column, 150 mm, 5 um, 13 nm; mobile phase, acetonitrile in water (with 10 mM NH$_4$HCO$_3$ and 0.1% NH$_3$.H$_2$O), 5% to 75% gradient in 7 min; detector, UV 254 nm (18 mg, 25%, yellow solid). HPLC: 91.7% purity, RT=2.14 min. MS: m/z=381.3 [M+H]$^+$. $^1$H NMR (400 MHz, Methanol-d$_4$, ppm) δ 8.83 (d, J=1.8 Hz, 1H), 8.76 (d, J=1.8 Hz, 1H), 7.97 (d, J=8.7 Hz, 1H), 6.78 (d, J=8.7 Hz, 1H), 4.64-4.54 (m, 1H), 4.31-4.21 (m, 1H), 4.12-3.96 (m, 2H), 3.76-3.62 (m, 5H), 3.09-3.04 (m, 2H), 2.71-2.59 (m, 1H), 2.57-2.45 (m, 4H), 1.12 (d, J=6.8 Hz, 3H).

Compound 8 (N-[(3R,4R)-1-(8-cyanoquinoxalin-5-yl)-4-methylpyrrolidin-3-yl]-2-(1,4-dimethylpiperidin-4-yl)acetamide)

From 8-[(3R,4R)-3-amino-4-methylpyrrolidin-1-yl]quinoxaline-5-carbonitrile (43 mg, 0.17 mmol) and 2-(1,4-dimethylpiperidin-4-yl)acetic acid, purified by prep-HPLC under the following conditions: column, XBridge Prep C18 OBD column, 150 mm, 5 um, 13 nm; mobile phase, acetonitrile in water (with 10 mM NH$_4$HCO$_3$), 22% to 35% gradient in 7 min; detector, UV 254 nm (12 mg, 17%, yellow solid). HPLC: 94.5% purity, RT=4.31 min. MS: m/z=407.3 [M+H]$^+$. $^1$H NMR (300 MHz, DMSO-d$_6$, ppm) δ 8.91 (d, J=1.8 Hz, 1H), 8.80 (d, J=1.8 Hz, 1H), 8.01 (d, J=8.7 Hz, 1H), 7.89 (d, J=8.3 Hz, 1H), 6.71 (d, J=8.8 Hz, 1H), 4.52-4.39 (m, 1H), 4.19-4.09 (m, 1H), 3.97-3.90 (m, 1H), 3.79-3.55 (m, 2H), 2.47-1.93 (m, 10H), 1.55-1.39 (m, 2H), 1.31-1.25 (m, 2H), 1.08-0.88 (m, 6H).

Compound 15 ((2S)—N-[(3R,4R)-1-(8-cyanoquinoxalin-5-yl)-4-methylpyrrolidin-3-yl]-2-hydroxy-3-methylbutanamide)

From 8-[(3R,4R)-3-amino-4-methylpyrrolidin-1-yl]quinoxaline-5-carbonitrile and (2S)-2-hydroxy-3-methylbutanoic acid, purified by prep-HPLC under the following conditions: column, XBridge Shield Prep C18 OBD column, 150 mm, 5 um, 13 nm; mobile phase, acetonitrile in water (with 10 mmol/L NH$_4$HCO$_3$ and 0.1% NH$_3$.H$_2$O), 30% to 35% gradient in 7 min; detector, UV 254 nm (29 mg, 27%, yellow solid). HPLC: 95.0% purity, RT=3.35 min. MS: m/z=354.3 [M+H]$^+$. $^1$H NMR (400 MHz, DMSO-d$_6$, ppm) δ 8.93 (d, J=1.9 Hz, 1H), 8.81 (d, J=1.8 Hz, 1H), 8.03 (d, J=8.7 Hz, 1H), 7.79 (d, J=8.5 Hz, 1H), 6.73 (d, J=8.8 Hz, 1H), 5.09 (d, J=6.1 Hz, 1H), 4.55-4.45 (m, 1H), 4.21-4.12 (m, 1H), 4.05-3.74 (m, 2H), 3.71-3.58 (m, 2H), 2.58-2.49 (m, 1H), 1.98-1.85 (m, 1H), 0.98 (d, J=6.8 Hz, 3H), 0.86 (d, J=6.8 Hz, 3H), 0.73 (d, J=6.8 Hz, 3H).

Compound 16 ((2R)—N-[(3R,4R)-1-(8-cyanoquinoxalin-5-yl)-4-methylpyrrolidin-3-yl]-2-hydroxy-3-methylbutanamide)

From 8-[(3R,4R)-3-amino-4-methylpyrrolidin-1-yl]quinoxaline-5-carbonitrile and (2R)-2-hydroxy-3-methylbutanoic acid, purified by prep-HPLC under the following conditions: column, XBridge Shield Prep C18 OBD column, 150 mm, 5 um, 13 nm; mobile phase, acetonitrile in water (with 10 mmol/L NH$_4$HCO$_3$ and 0.1% NH$_3$.H$_2$O), 35% to 39% gradient in 7 min; detector, UV 254 nm (14 mg, 26%, yellow solid). HPLC: 96.1% purity, RT=2.16 min. MS: m/z=354.4 [M+H]$^+$. $^1$H NMR (300 MHz, Methanol-d$_4$, ppm) δ 8.79 (d, J=1.8 Hz, 1H), 8.73 (d, J=1.8 Hz, 1H), 7.94 (d, J=8.7 Hz, 1H), 6.75 (d, J=8.7 Hz, 1H), 4.61-4.54 (m, 1H), 4.30-4.18 (m, 1H), 4.11-3.91 (m, 2H), 3.86-3.78 (m, 1H), 3.76-3.63 (m, 1H), 2.66-2.57 (m, 1H), 2.11-1.96 (m, 1H), 1.10 (d, J=6.8 Hz, 3H), 0.96 (d, J=6.9 Hz, 3H), 0.86 (d, J=6.8 Hz, 3H).

Example 3: Synthesis of Compounds 3 and 4 (N-[(3R,4R)-1-(8-cyanoquinoxalin-5-yl)-4-methylpyrrolidin-3-yl]-2-[(3S)-1-methylpiperidin-3-yl]acetamide and N-[(3R,4R)-1-(8-cyanoquinoxalin-5-yl)-4-methylpyrrolidin-3-yl]-2-[(3R)-1-methylpiperidin-3-yl]acetamide)

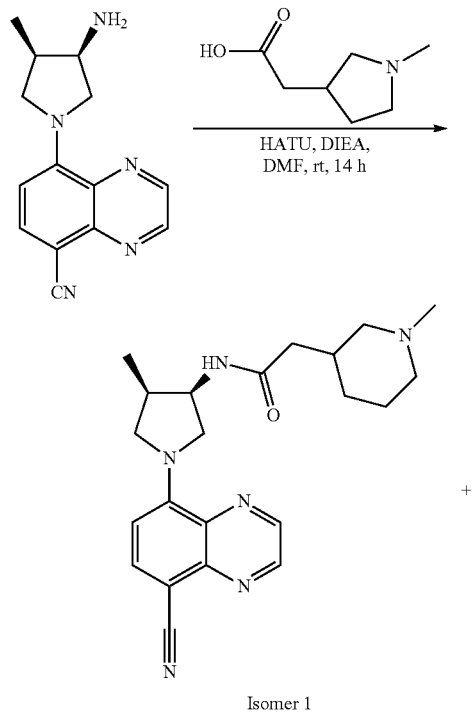

Isomer 1

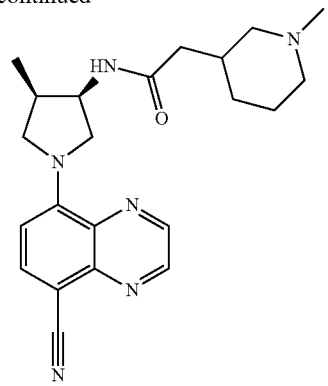

Isomer 2

N-[(3R,4R)-1-(8-cyanoquinoxalin-5-yl)-4-methylpyrrolidin-3-yl]-2-[(3S)-1-methylpiperidin-3-yl]acetamide and N-[(3R,4R)-1-(8-cyanoquinoxalin-5-yl)-4-methylpyrrolidin-3-yl]-2-[(3R)-1-methylpiperidin-3-yl]acetamide To a solution of 8-[(3R,4R)-3-amino-4-methylpyrrolidin-1-yl]quinoxaline-5-carbonitrile (48 mg, 0.19 mmol) in N,N-dimethylformamide (4 mL) was added 2-(1-methylpiperidin-3-yl)acetic acid (59 mg, 0.38 mmol), HATU (144 mg, 0.38 mmol) and DIEA (147 mg, 1.14 mmol) at room temperature. The resulting solution was stirred for 14 hours at room temperature. When the reaction was done, it was quenched by the addition of water (15 mL). The resulting mixture was extracted with DCM (30 mL×3). The organic phases were combined, washed with brine and dried over Na$_2$SO$_4$. The solvent was removed under reduced pressure and the residue was first purified by prep-HPLC under the following conditions: column, XBridge C18 OBD Prep Column, 150 mm, 5 um; mobile phase, acetonitrile in water (with 10 mM NH$_4$HCO$_3$), 25% to 31% gradient in 8 min; detector, UV 254 nm. Then the two diastereomers were obtained by separation on chiral prep-HPLC under the following conditions: column, CHIRALPAK IG, 2×15 cm, 3 um; mobile phase, 100% MeOH (with 0.1% DEA) in 20 min; detector, UV 254 nm.

Isomer 1:

(18 mg, 25%, yellow solid) HPLC: 90.3% purity, RT=3.55 min. MS: m/z=393.4 [M+H]$^+$. $^1$H NMR (400 MHz, Methanol-d$_4$, ppm) δ 8.82 (d, J=1.7 Hz, 1H), 8.76 (d, J=1.8 Hz, 1H), 7.96 (d, J=8.7 Hz, 1H), 6.77 (d, J=8.7 Hz, 1H), 4.62-4.57 (m, 1H), 4.32-4.22 (m, 1H), 4.09-3.94 (m, 2H), 3.75-3.65 (m, 1H), 2.92-2.78 (m, 2H), 2.68-2.56 (m, 1H), 2.27 (s, 3H), 2.18-2.11 (m, 2H), 2.04-1.99 (m, 2H), 1.84-1.64 (m, 3H), 1.64-1.53 (m, 1H), 1.11 (d, J=6.8 Hz, 3H), 1.03-0.90 (m, 1H).

Isomer 2:

(11 mg, 13%, yellow solid) HPLC: 95.3% purity, RT=5.07 min. MS: m/z=393.1 [M+H]$^+$. $^1$H NMR (300 MHz, Methanol-d$_4$, ppm) δ 8.83-8.69 (m, 2H), 7.94 (d, J=8.7 Hz, 1H), 6.74 (d, J=8.8 Hz, 1H), 4.60-4.53 (m, 1H), 4.30-4.18 (m, 1H), 4.08-3.89 (m, 2H), 3.74-3.60 (m, 1H), 3.04-2.97 (m, 2H), 2.67-2.51 (m, 1H), 2.40 (s, 3H), 2.32-1.96 (m, 6H), 1.82-1.72 (m, 2H), 1.67-1.56 (m, 1H), 1.30-0.85 (m, 4H).

The following compounds were synthesized in an analogous manner:

Compounds 5 and 6 (N-[(3R,4R)-1-(8-cyanoquinoxalin-5-yl)-4-methylpyrrolidin-3-yl]-2-[(3S)-1-methylpyrrolidin-3-yl]acetamide and N-[(3R,4R)-1-(8-cyanoquinoxalin-5-yl)-4-methylpyrrolidin-3-yl]-2-[(3R)-1-methylpyrrolidin-3-yl]acetamide)

From 8-[(3R,4R)-3-amino-4-methylpyrrolidin-1-yl]quinoxaline-5-carbonitrile and 2-(1-methylpyrrolidin-3-yl)acetic acid, purified by prep-HPLC under the following conditions: column, XBridge C18 OBD Prep Column, 150 mm, 5 um; mobile phase, acetonitrile in water (with 10 mM NH$_4$HCO$_3$ and 0.1% NH$_3$.H$_2$O), 15% to 45% gradient in 8 min; detector, UV 254 nm. The two diastereomers were obtained by separation on chiral prep-HPLC under the following conditions: column, CHIRALPAK IC-3, 0.46×10 cm, 3 um; mobile phase, MtBE (with 0.1% DEA) in MeOH, 70% isocratic in 30 min; detector, UV 254 nm. Isomer 1: (13 mg, 15%, yellow solid) HPLC: 97.3% purity, RT=3.00 min. MS: m/z=379.3 [M+H]$^+$. $^1$H NMR (300 MHz, DMSO-d$_6$, ppm) δ 8.91 (d, J=1.8 Hz, 1H), 8.80 (d, J=1.8 Hz, 1H), 8.00 (d, J=8.4 Hz, 2H), 6.71 (d, J=8.8 Hz, 1H), 4.51-4.40 (m, 1H), 4.15-4.08 (m, 1H), 3.96-3.89 (m, 1H), 3.80-3.73 (m, 1H), 3.61-3.54 (m, 1H), 2.37-2.26 (m, 5H), 2.23-1.98 (m, 6H), 1.91-1.75 (m, 1H), 1.36-1.21 (m, 1H), 0.94 (d, J=6.8 Hz, 3H). Isomer 2: (15 mg, 16%, yellow solid) HPLC: 94.1% purity, RT=4.39 min. MS: m/z=379.3 [M+H]$^+$. $^1$H NMR (300 MHz, Methanol-d$_4$, ppm) δ 8.82-8.69 (m, 2H), 7.93 (d, J=8.7 Hz, 1H), 6.73 (d, J=8.7 Hz, 1H), 4.59-4.52 (m, 1H), 4.29-4.17 (m, 1H), 4.08-3.88 (m, 2H), 3.73-3.60 (m, 1H), 2.80-2.68 (m, 1H), 2.66-2.52 (m, 4H), 2.33-2.17 (m, 6H), 2.14-1.95 (m, 1H), 1.57-1.39 (m, 1H), 1.07 (d, J=6.8 Hz, 3H).

Compounds 13 and 14 ((2S)—N-[(3R,4R)-1-(8-cyanoquinoxalin-5-yl)-4-methylpyrrolidin-3-yl]-2-cyclopropyl-2-hydroxyacetamide and (2R)—N-[(3R,4R)-1-(8-cyanoquinoxalin-5-yl)-4-methylpyrrolidin-3-yl]-2-cyclopropyl-2-hydroxyacetamide)

From 8-[(3R,4R)-3-amino-4-methylpyrrolidin-1-yl]quinoxaline-5-carbonitrile (52 mg, 0.20 mmol) and 2-cyclopropyl-2-hydroxyacetic acid, purified by prep-HPLC under the following conditions: column, XBridge Prep C18 OBD Column, 150 mm, 5 um; mobile phase, acetonitrile in water (with 10 mmol/L NH$_4$HCO$_3$ and 0.1% NH$_3$.H$_2$O), 5% to 62% gradient in 7 min; detector, UV 254 nm. The two diastereomers were obtained by separation on chiral prep-HPLC under the following conditions: column, CHIRALPAK IA-3, 0.46×5 cm, 3 um; mobile phase, hexane (with 0.1% DEA) in EtOH, 50% isocratic in 15 min; detector, UV 254 nm. Isomer 1: (20 mg, 27%, yellow solid) HPLC: 96.1% purity, RT=1.17 min. MS: m/z=352.2 [M+H]$^+$. $^1$H NMR (400 MHz, DMSO-d$_6$, ppm) δ 8.93 (d, J=1.8 Hz, 1H), 8.82 (d, J=1.8 Hz, 1H), 8.04 (d, J=8.7 Hz, 1H), 7.78 (d, J=8.5 Hz, 1H), 6.74 (d, J=8.8 Hz, 1H), 5.09 (d, J=6.1 Hz, 1H), 4.52-4.47 (m, 1H), 4.21-4.16 (m, 1H), 4.00-3.95 (m, 1H), 3.89-3.81 (m, 1H), 3.62-3.57 (m, 1H), 3.45 (t, J=6.4 Hz, 1H), 2.61-2.50 (m, 1H), 1.08-0.95 (m, 4H), 0.40-0.22 (m, 4H). Isomer 2: (11 mg, 13%, yellow solid) HPLC: 97.4% purity, RT=1.19 min. MS: m/z=352.2 [M+H]$^+$. $^1$H NMR (400 MHz, DMSO-d$_6$, ppm) δ 8.94 (d, J=1.7 Hz, 1H), 8.83 (d, J=1.7 Hz, 1H), 8.05 (d, J=8.6 Hz, 1H), 7.70 (d, J=8.4 Hz, 1H), 6.74 (d, J=8.7 Hz, 1H), 5.28 (d, J=5.7 Hz, 1H), 4.56-4.46 (m, 1H), 4.25-4.15 (m, 1H), 4.03-3.94 (m, 1H), 3.91-3.83 (m, 1H), 3.67-3.53 (m, 2H), 2.61-2.52 (m, 1H), 1.12-1.02 (m, 1H), 1.00 (d, J=6.8 Hz, 3H), 0.41-0.25 (m, 4H).

Example 4: Synthesis of Compound 9 (N-[(3R,4R)-1-(8-cyanoquinoxalin-5-yl)-4-methylpyrrolidin-3-yl]-2-(4-fluoropiperidin-4-yl)acetamide)

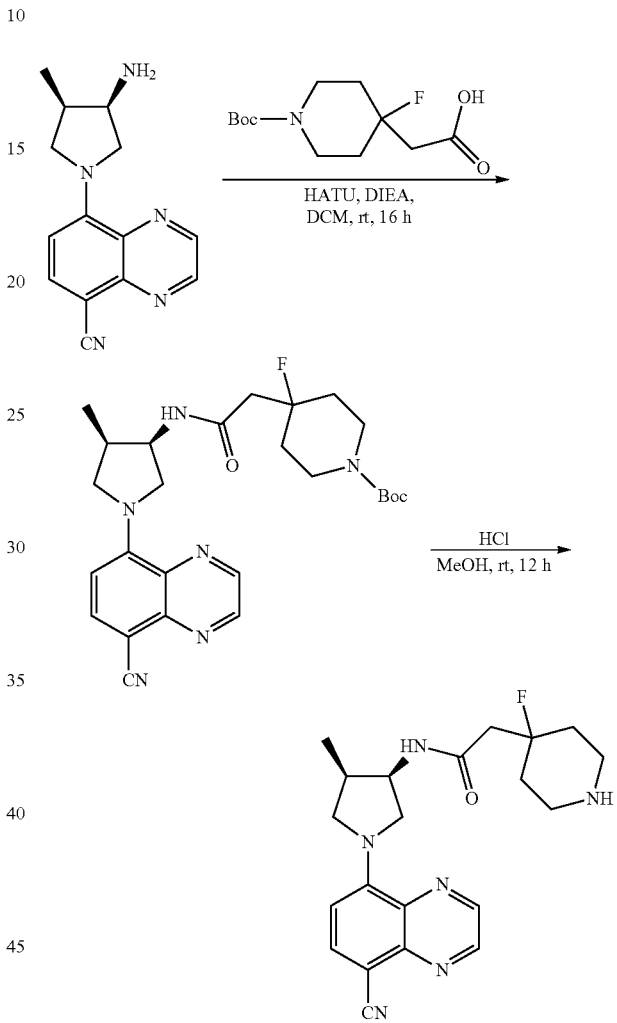

tert-butyl 4-([[[(3R,4R)-1-(8-cyanoquinoxalin-5-yl)-4-methylpyrrolidin-3-yl]carbamoyl]methyl)-4-fluoropiperidine-1-carboxylate To a solution of 8-[(3R,4R)-3-amino-4-methylpyrrolidin-1-yl]quinoxaline-5-carbonitrile (129 mg, 0.51 mmol) in DCM (8 mL) were added 2-[1-[(tert-butoxy)carbonyl]-4-fluoropiperidin-4-yl]acetic acid (266 mg, 1.02 mmol), HATU (388 mg, 1.02 mmol) and DIEA (394 mg, 3.06 mmol) at room temperature. The resulting solution was stirred for 16 h at room temperature. When the reaction was done, the reaction mixture was concentrated under reduced pressure and the residue was purified by prep-HPLC under the following conditions: column, XBridge Prep C18 OBD column, 150 mm, 5 um, 13 nm; mobile phase, acetonitrile in water (with 10 mM NH$_4$HCO$_3$ and 0.1% NH$_3$.H$_2$O), 40% to 53% gradient in 7 min; detector, UV 254 nm. 4-([[[(3R,4R)-

1-(8-cyanoquinoxalin-5-yl)-4-methylpyrrolidin-3-yl]carbamoyl]methyl)-4-fluoropiperidine-1-carboxylate was obtained as yellow solid (76 mg, 30%). MS: m/z=497.3 [M+H]⁺.

N-[(3R,4R)-1-(8-cyanoquinoxalin-5-yl)-4-methylpyrrolidin-3-yl]-2-(4-fluoropiperidin-4-yl)acetamide To a solution of tert-butyl 4-([[[(3R,4R)-1-(8-cyanoquinoxalin-5-yl)-4-methylpyrrolidin-3-yl]carbamoyl]methyl)-4-fluoropiperidine-1-carboxylate (76 mg, 0.15 mmol) in MeOH (4 mL) was added hydrogen chloride solution (12 N, 4 mL, 48 mmol) at the room temperature. The resulting solution was stirred for 12 h at room temperature. When the reaction was done, the reaction mixture was concentrated under reduced pressure and the residue was purified by prep-HPLC under the following conditions: column, XBridge Prep C18 OBD column, 150 mm, 5 um, 13 nm; mobile phase, acetonitrile in water (with 10 mM NH₄HCO₃ and 0.1% NH₃.H₂O), 15% to 42% gradient in 7 min; detector, UV 254 nm. N-[(3R,4R)-1-(8-cyanoquinoxalin-5-yl)-4-methylpyrrolidin-3-yl]-2-(4-fluoropiperidin-4-yl)acetamide was obtained as yellow solid (13 mg, 19%).

Compound 9

MS: m/z=497.3 [M+H]⁺. ¹H NMR (300 MHz, DMSO-d₆, ppm) δ 8.95 (d, J=1.8 Hz, 1H), 8.84 (d, J=1.8 Hz, 1H), 8.13-8.01 (m, 2H), 6.75 (d, J=8.8 Hz, 1H), 4.52-4.43 (m, 1H), 4.26-3.86 (m, 2H), 3.84-3.74 (m, 1H), 3.62-3.52 (m, 1H), 2.74-2.61 (m, 4H), 2.50-2.36 (m, 3H), 1.76-1.55 (m, 4H), 1.00 (d, J=6.8 Hz, 3H).

Example 5: Synthesis of Compound 10 (N-[(3R,4R)-1-(8-cyanoquinoxalin-5-yl)-4-methylpyrrolidin-3-yl]-2-(4-fluoro-1-methylpiperidin-4-yl)acetamide)

N-[(3R,4R)-1-(8-cyanoquinoxalin-5-yl)-4-methylpyrrolidin-3-yl]-2-(4-fluoro-1-methylpiperidin-4-yl)acetamide To a solution of N-[(3R,4R)-1-(8-cyanoquinoxalin-5-yl)-4-methylpyrrolidin-3-yl]-2-(4-fluoropiperidin-4-yl)acetamide (32 mg, 0.08 mmol) in MeOH (3 mL) was added (HCHO)ₙ (44 mg, 0.49 mmol), NaOAC (135 mg, 1.64 mmol) and NaBH₄ (15 mg, 0.41 mmol) at the room temperature. The resulting solution was stirred for 3 h at room temperature. When the reaction was done, the reaction mixture was concentrated under reduced pressure and the residue was purified by prep-HPLC under the following conditions: column, XBridge Shield RP18 OBD column, 150 mm, 5 um, 13 nm; mobile phase, acetonitrile in water (with 10 mM NH₄HCO₃), 35% to 65% gradient in 7 min; detector, UV 254 nm. N-[(3R,4R)-1-(8-cyanoquinoxalin-5-yl)-4-methylpyrrolidin-3-yl]-2-(4-fluoro-1-methylpiperidin-4-yl)acetamide was obtained as yellow solid (7 mg, 21%).

Compound 10

HPLC: 90.3% purity, RT=5.76 min. MS: m/z=411.3 [M+H]⁺. ¹H NMR (300 MHz, Methanol-d₄, ppm) δ 8.78 (d, J=1.8 Hz, 1H), 8.71 (d, J=1.8 Hz, 1H), 7.92 (d, J=8.7 Hz, 1H), 6.73 (d, J=8.7 Hz, 1H), 4.62-4.52 (m, 1H), 4.31-4.16 (m, 1H), 4.11-3.88 (m, 2H), 3.73-3.59 (m, 1H), 3.38-3.31 (m, 2H), 3.22-3.06 (m, 2H), 2.80 (s, 3H), 2.73-2.52 (m, 3H), 2.25-1.96 (m, 4H), 1.09 (d, J=6.8 Hz, 3H).

Example 6: Synthesis of Compounds 11 and 12 (N-[(3R,4R)-1-(8-cyanoquinoxalin-5-yl)-4-methylpyrrolidin-3-yl]-2-[(4S)-3,3-difluoro-1-methylpiperidin-4-yl]acetamide and N-[(3R,4R)-1-(8-cyanoquinoxalin-5-yl)-4-methylpyrrolidin-3-yl]-2-[(4R)-3,3-difluoro-1-methylpiperidin-4-yl]acetamide)

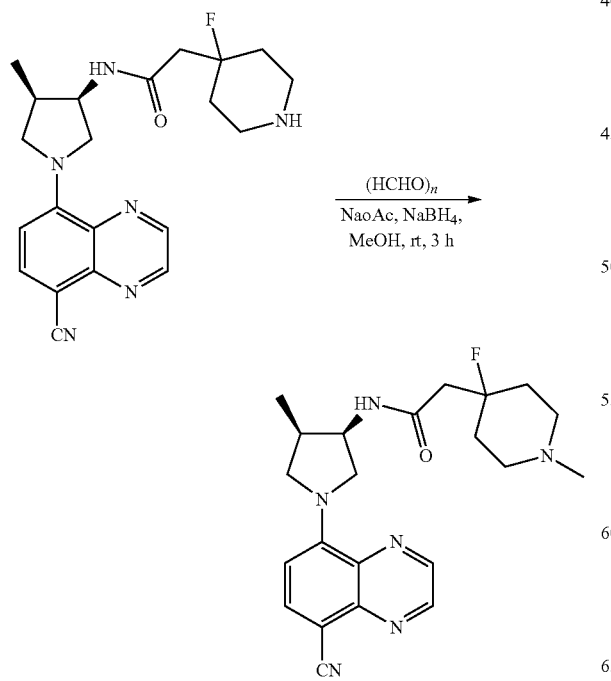

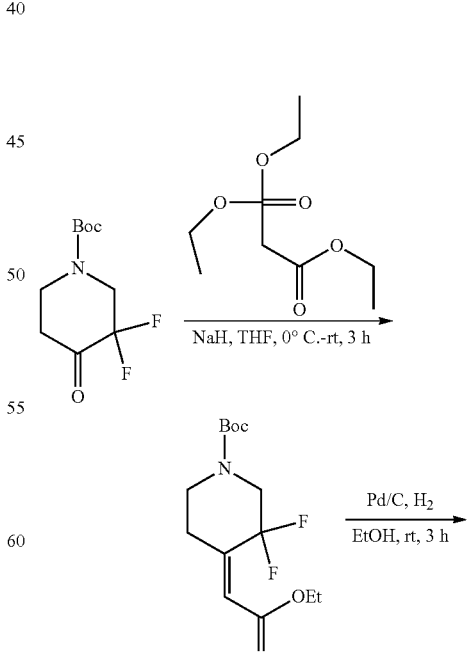

-continued

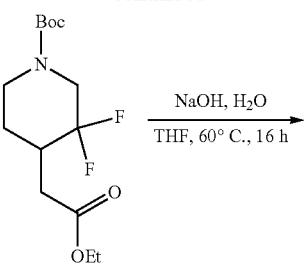

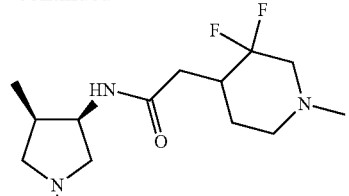

Isomer 2 tert-butyl 4-(2-ethoxy-2-oxoethylidene)-3,3-dimethylpiperidine-1-carboxylate

At 0° C., to a solution of ethyl (diethoxyphosphoryl) formate (950 mg, 4.52 mmol) in THF (50 mL) was added sodium hydride (102 mg, 4.25 mmol) at 0° C. The resulting mixture was stirred for 15 min and then was added by tert-butyl 3,3-difluoro-4-oxopiperidine-1-carboxylate (798 mg, 3.39 mmol) at 0° C. The reaction mixture was stirred for 0.5 h at 0° C., warmed up to room temperature and stirred for 3 h at room temperature. When the reaction was done, it was quenched by the addition of water (20 mL). The resulting mixture was extracted with ethyl acetate (40 mL×3). The organic phases were combined, washed with brine and dried over $Na_2SO_4$. The solvent was removed under reduced pressure and the residue was purified by flash chromatography eluting with EtOAc in petroleum ether (0% to 50% gradient) to yield tert-butyl 4-(2-ethoxy-2-oxoethylidene)-3,3-dimethylpiperidine-1-carboxylate as colorless oil (560 mg, 35%). MS: m/z=205.9 [M−100+1]$^+$.

tert-butyl 4-(2-ethoxy-2-oxoethyl)-3,3-difluoropiperidine-1-carboxylate

To a solution of tert-butyl 4-(2-ethoxy-2-oxoethylidene)-3,3-difluoropiperidine-1-carboxylate (1.11 g, 3.62 mmol) in EtOH (30 mL) was added Palladium carbon (138 mg, 0.13 mmol) under nitrogen atmosphere. The reaction tank was vacuumed and flushed with hydrogen. The reaction mixture was then hydrogenated for 3 h under hydrogen atmosphere at room temperature using a hydrogen balloon. When the reaction was done, the reaction mixture was filtered through a celite pad and the filtrate was concentrated under reduced pressure to yield tert-butyl 4-(2-ethoxy-2-oxoethyl)-3,3-difluoropiperidine-1-carboxylate as colorless oil (1.01 g, 92%). MS: m/z=207.9 [M−100+1]$^+$.

2-[1-[(tert-butoxy)carbonyl]-3,3-difluoropiperidin-4-yl]acetic

To a solution of tert-butyl 4-(2-ethoxy-2-oxoethyl)-3,3-difluoropiperidine-1-carboxylate (1.01 g, 3.29 mmol) in tetrahydrofuran (25 mL) was added sodium hydroxide solution (500 mg in 25 mL water, 12.5 mmol) at room temperature. The resulting mixture was stirred for 16 h at 60° C. When the reaction was done, the reaction mixture was concentrated under vacuum. The pH value of the residue mixture was adjusted to 5 with hydrogen chloride solution (4

N), and then the resulting mixture was extracted with ethyl acetate (50 mL×3). The organic phases were combined, washed with brine and dried over Na$_2$SO$_4$. The solvent was removed under reduced pressure to yield 2-[1-[(tert-butoxy)carbonyl]-3,3-difluoropiperidin-4-yl]acetic acid as colorless oil (504 mg, 42%). MS: m/z=280.1 [M+H]$^+$.

2-4-([[(3R,4R)-1-(8-cyanoquinoxalin-5-yl)-4-methylpyrrolidin-3-yl]carbamoyl]methyl)-3,3-difluoropiperidine-1-carboxylate To a solution 8-[(3R,4R)-3-amino-4-methylpyrrolidin-1-yl]quinoxaline-5-carbonitrile (208 mg, 0.82 mmol) in DCM (14 mL) was added 2-[1-[(tert-butoxy)carbonyl]-3,3-difluoropiperidin-4-yl]acetic acid (581 mg, 2.08 mmol), HATU (620 mg, 1.63 mmol) and DIEA (633 mg, 4.90 mmol) at room temperature. The resulting solution was stirred for 1 h at room temperature. When the reaction was done, it was quenched by the addition of water (15 mL). The resulting mixture was extracted with ethyl acetate (50 mL×3). The organic phases were combined, washed with brine and dried over Na$_2$SO$_4$. The solvent was removed under reduced pressure to yield tert-butyl 4-([[(3R,4R)-1-(8-cyanoquinoxalin-5-yl)-4-methylpyrrolidin-3-yl]carbamoyl]methyl)-3,3-difluoropiperidine-1-carboxylate as yellow solid (320 mg, crude). MS: m/z=515.3 [M+H]$^+$.

N-[(3R,4R)-1-(8-cyanoquinoxalin-5-yl)-4-methylpyrrolidin-3-yl]-2-[(4S)-3,3-difluoro-1-methylpiperidin-4-yl]acetamide and N-[(3R,4R)-1-(8-cyanoquinoxalin-5-yl)-4-methylpyrrolidin-3-yl]-2-[(4R)-3,3-difluoro-1-methylpiperidin-4-yl]acetamide To a solution of tert-butyl 4-([[(3R,4R)-1-(8-cyanoquinoxalin-5-yl)-4-methylpyrrolidin-3-yl]carbamoyl]methyl)-3,3-difluoropiperidine-1-carboxylate (320 mg, crude) in HCOOH (26 mL) was added formalin (10%, 15 mL, 54 mmol) at room temperature. The resulting mixture was stirred for 1 h at 140° C. When the reaction was done, the reaction mixture was concentrated under reduced pressure and the residue was purified by prep-HPLC under the following conditions: column, XBridge C18 OBD Prep Column, 150 mm, 5 um; mobile phase, acetonitrile in water (with 10 mM NH$_4$HCO$_3$ and 0.1% NH$_3$.H$_2$O), 30% to 44% gradient in 8 min; detector, UV 254 nm. Then the two diastereomers were obtained by separation on chiral prep-HPLC under the following conditions: column, CHIRALPAK IA-3, 0.46×5 cm, 3 um; mobile phase, hexane (with 0.1% DEA) in EtOH, 50% isocratic in 15 min; detector, UV 254 nm.

Isomer 1:
(93 mg, 59%, yellow solid) HPLC: 93.2% purity, RT=2.67 min. MS: m/z=429.4 [M+H]$^+$. $^1$H NMR (300 MHz, Methanol-d$_4$, ppm) δ 8.78 (d, J=1.8 Hz, 1H), 8.72 (d, J=1.8 Hz, 1H), 7.93 (d, J=8.7 Hz, 1H), 6.73 (d, J=8.7 Hz, 1H), 4.62-4.53 (m, 1H), 4.30-4.17 (m, 1H), 4.07-3.88 (m, 2H), 3.73-3.60 (m, 1H), 3.03-2.97 (m, 1H), 2.86-2.75 (m, 1H), 2.69-2.50 (m, 2H), 2.34-2.01 (m, 7H), 1.85-1.72 (m, 1H), 1.60-1.42 (m, 1H), 1.07 (d, J=6.9 Hz, 3H).

Isomer 2:
(11 mg, 13%, yellow solid) HPLC: 93.1% purity, RT=2.74 min. MS: m/z=429.4 [M+H]$^+$. $^1$H NMR (300 MHz, Methanol-d$_4$, ppm) δ 8.82-8.69 (m, 2H), 7.93 (d, J=8.7 Hz, 1H), 6.73 (d, J=8.7 Hz, 1H), 4.60-4.53 (m, 1H), 4.31-4.18 (m, 1H), 4.07-3.89 (m, 2H), 3.73-3.60 (m, 1H), 3.04-2.94 (m, 1H), 2.81-2.70 (m, 1H), 2.69-2.50 (m, 2H), 2.38-1.89 (m, 7H), 1.79-1.68 (m, 1H), 1.56-1.41 (m, 1H), 1.07 (d, J=6.9 Hz, 3H).

Example 7: Synthesis of compound 17 ((3R,4R)-4-methyl-1-[8-(trifluoromethyl)quinolin-5-yl]pyrrolidin-3-amine)

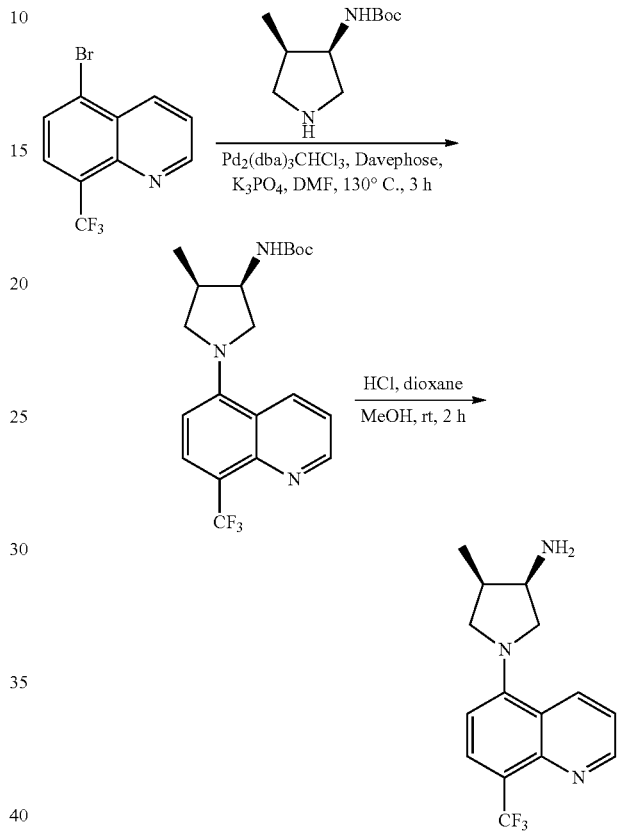

tert-butyl N-[(3R,4R)-4-methyl-1-[8-(trifluoromethyl)quinolin-5-yl]pyrrolidin-3-yl]carbamate To a solution of 5-bromo-8-(trifluoromethyl)quinoline (245 mg, 0.89 mmol) in N,N-dimethylformamide (5 mL) was added tert-butyl N-[(3R,4R)-4-methylpyrrolidin-3-yl]carbamate (241 mg, 1.20 mmol), Pd$_2$(dba)$_3$.CHCl$_3$ (124 mg, 0.12 mmol), K$_3$PO$_4$ (768 mg, 3.62 mmol) and DavePhos (93 mg, 0.23 mmol) at the room temperature. The resulting mixture was stirred for 3 h at 130° C. When the reaction was done, the solids in the reaction mixture were filtered out, and the filtrate was diluted by water (20 mL). The resulting mixture was extracted with DCM (50 mL×3). The organic phases were combined, washed with brine and dried over Na$_2$SO$_4$. The solution was removed under reduced pressure and the residue was purified by flash chromatography eluting with EtOAc in hexane (0% to 20% gradient) to yield tert-butyl N-[(3R,4R)-4-methyl-1-[8-(trifluoromethyl)quinolin-5-yl]pyrrolidin-3-yl]carbamate as brown solid (298 mg, 85%). MS: m/z=396.2 [M+H]$^+$.

(3R,4R)-4-methyl-1-[8-(trifluoromethyl)quinolin-5-yl]pyrrolidin-3-amine

To a solution of tert-butyl N-[(3R,4R)-4-methyl-1-[8-(trifluoromethyl)quinolin-5-yl]pyrrolidin-3-yl]carbamate (50 mg, 0.13 mmol) in methanol (3 mL) was added hydrogen chloride solution (6 M in dioxane, 2 mL, 12 mmol) at room temperature. The resulting solution was stirred for 2 h at room temperature. When the reaction was done, the reaction mixture was concentrated under reduced pressure and the residue was purified by prep-HPLC under the following conditions: column, XBridge Shield Prep C18 OBD column, 150 mm, 5 um, 13 nm; mobile phase, acetonitrile in water (with 10 mmol/L $NH_4HCO_3$ and 0.1% $NH_3.H_2O$), 30% to 51% gradient in 7 min; detector, UV 254 nm. (3R,4R)-4-methyl-1-[8-(trifluoromethyl)quinolin-5-yl]pyrrolidin-3-amine was obtained as yellow solid (25 mg, 64%).

Compound 17

HPLC: 93.4% purity, RT=2.08 min. MS: m/z=296.0 [M+H]$^+$. $^1$H NMR (300 MHz, DMSO-d$_6$, ppm) δ 8.89 (d, J=3.9 Hz, 1H), 8.70 (d, J=8.8 Hz, 1H), 7.86 (d, J=8.4 Hz, 1H), 7.51-7.40 (m, 1H), 6.67 (d, J=8.5 Hz, 1H), 3.92-3.80 (m, 1H), 3.58-3.43 (m, 3H), 3.38-3.27 (m, 1H), 2.37-2.22 (m, 1H), 1.03 (d, J=6.8 Hz, 3H).

Example 8: Synthesis of compound 18 (N-[(3R,4R)-4-methyl-1-[8-(trifluoromethyl)quinolin-5-yl]pyrrolidin-3-yl]-2-(1-methylpiperidin-4-yl)acetamide)

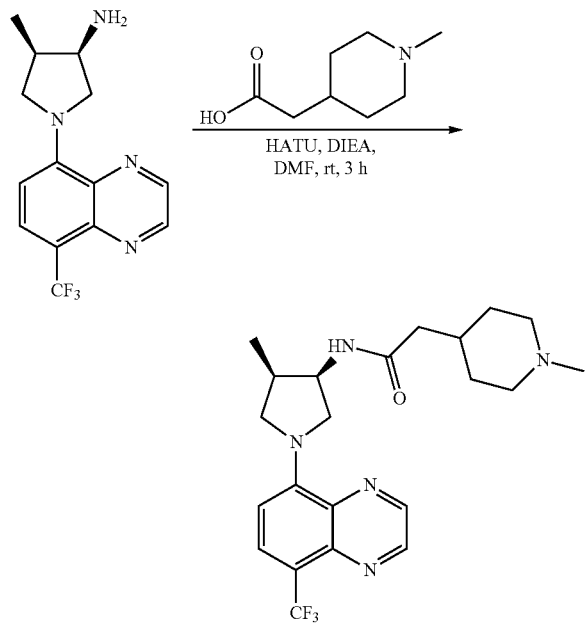

N-[(3R,4R)-4-methyl-1-[8-(trifluoromethyl)quinolin-5-yl]pyrrolidin-3-yl]-2-(1-methylpiperidin-4-yl)acetamide To a solution of (3R,4R)-4-methyl-1-[8-(trifluoromethyl)quinolin-5-yl]pyrrolidin-3-amine (38 mg, 0.13 mmol) in N,N-dimethylformamide (3 mL) was added 2-(1-methylpiperidin-4-yl)acetic acid (63 mg, 0.40 mmol), DIEA (31 mg, 0.24 mmol) and HATU (307 mg, 0.81 mmol, 6.36 equiv, 95%) at the room temperature. The resulting solution was stirred for 3 h at room temperature. When the reaction was done, the reaction mixture was concentrated under reduced pressure and the residue was purified by prep-HPLC under the following conditions: column, XBridge Shield Prep C18 OBD column, 150 mm, 5 um, 13 nm; mobile phase, acetonitrile in water (with 10 mmol/L $NH_4HCO_3$ and 0.1% $NH_3.H_2O$), 35% to 42% gradient in 7 min; detector, UV 254 nm. N-[(3R,4R)-4-methyl-1-[8-(trifluoromethyl)quinolin-5-yl]pyrrolidin-3-yl]-2-(1-methylpiperidin-4-yl)acetamide was obtained as yellow solid (25 mg, 44%).

Compound 18

HPLC: 98.4% purity, RT=0.90 min. MS: m/z=435.2 [M+H]$^+$. $^1$H NMR (300 MHz, DMSO-d$_6$, ppm) δ 8.95-8.86 (m, 1H), 8.69 (d, J=8.8, 1.7 Hz, 1H), 7.98-7.84 (m, 2H), 7.54-7.43 (m, 1H), 6.72 (d, J=8.5 Hz, 1H), 4.54-4.40 (m, 1H), 4.04-3.92 (m, 1H), 3.68-3.56 (m, 1H), 3.58-3.45 (m, 1H), 3.37-3.25 (m, 2H), 2.74-2.60 (m, 2H), 2.14-1.99 (m, 5H), 1.78 (d, J=9.4 Hz, 2H), 1.61-1.44 (m, 3H), 1.19-1.02 (m, 2H), 0.97 (d, J=6.8 Hz, 3H).

The following compounds were synthesized in an analogous manner:

Compound 23 (N-[(3R,4R)-4-methyl-1-[8-(trifluoromethyl)quinolin-5-yl]pyrrolidin-3-yl]-2-(morpholin-4-yl)acetamide)

From (3R,4R)-4-methyl-1-[8-(trifluoromethyl)quinolin-5-yl]pyrrolidin-3-amine and 2-(morpholin-4-yl)acetic acid, purified by prep-HPLC under the following conditions: column, XBridge Shield Prep C18 OBD column, 150 mm, 5 um, 13 nm; mobile phase, acetonitrile in water (with 0.05% $NH_3.H_2O$), 39% to 59% gradient in 8 min; detector, UV 254 nm (35 mg, 39%, yellow solid). HPLC: 96.3% purity, RT=2.80 min. MS: m/z=423.1 [M+H]$^+$. $^1$H NMR (300 MHz, DMSO-d$_6$, ppm) δ 8.96-8.87 (m, 1H), 8.70 (d, J=8.8, 1.7 Hz, 1H), 7.95-7.80 (m, 2H), 7.55-7.44 (m, 1H), 6.76 (d, J=8.5 Hz, 1H), 4.52-4.43 (m, 1H), 4.01-3.89 (m, 1H), 3.72-3.37 (m, 7H), 3.06-2.88 (m, 2H), 2.59-2.51 (m, 1H), 2.47-2.37 (m, 4H), 0.98 (d, J=6.8 Hz, 3H).

Compound 24 (2-(1,4-dimethylpiperidin-4-yl)-N-[(3R,4R)-4-methyl-1-[8-(trifluoromethyl)quinolin-5-yl]pyrrolidin-3-yl]acetamide)

From (3R,4R)-4-methyl-1-[8-(trifluoromethyl)quinolin-5-yl]pyrrolidin-3-amine (60 mg, 0.20 mmol) and 2-(1,4-dimethylpiperidin-4-yl)acetic acid, purified by prep-HPLC under the following conditions: column, XBridge Shield Prep C18 OBD column, 150 mm, 5 um, 13 nm; mobile phase, acetonitrile in water (with 10 mmol/L $NH_4HCO_3$ and 0.1% $NH_3.H_2O$), 40% to 52% gradient in 10 min; detector, UV 254 nm (45 mg, 49%, yellow solid). HPLC: 98.4% purity, RT=4.24 min. MS: m/z=449.4 [M+H]$^+$. $^1$H NMR (300 MHz, DMSO-d$_6$, ppm) δ 8.95-8.87 (m, 1H), 8.70 (d, J=8.8, 1.7 Hz, 1H), 7.94-7.84 (m, 2H), 7.55-7.44 (m, 1H), 6.72 (d, J=8.5 Hz, 1H), 4.50-4.41 (m, 1H), 4.04-3.92 (m, 1H), 3.66-3.46 (m, 2H), 3.40-3.30 (m, 1H), 2.36-2.30 (m, 2H), 2.22-1.99 (m, 8H), 1.58-1.44 (m, 2H), 1.34-1.27 (m, 2H), 1.03-0.91 (m, 6H).

Compound 31 ((2S)-2-hydroxy-3-methyl-N-[(3R,4R)-4-methyl-1-[8-(trifluoromethyl)quinolin-5-yl]pyrrolidin-3-yl]butanamide)

From (3R,4R)-4-methyl-1-[8-(trifluoromethyl)quinolin-5-yl]pyrrolidin-3-amine and (2S)-2-hydroxy-3-methylbutanoic acid, purified by prep-HPLC under the following conditions: column, XBridge Shield Prep C18 OBD column, 150 mm, 5 um; mobile phase, acetonitrile in water (with 10 mmol/L $NH_4HCO_3$ and 0.1% $NH_3.H_2O$), 40% to 56% gradient in 7 min; detector, UV 254 nm (42 mg, 53%, yellow solid). HPLC: 98.2% purity, RT=4.89 min. MS: m/z=396.1 $[M+H]^+$. $^1$H NMR (300 MHz, DMSO-$d_6$, ppm) δ 8.94-8.86 (m, 1H), 8.72 (d, J=8.8, 1.7 Hz, 1H), 7.88 (d, J=8.4 Hz, 1H), 7.67 (d, J=8.5 Hz, 1H), 7.53-7.42 (m, 1H), 6.74 (d, J=8.5 Hz, 1H), 4.58-4.36 (m, 1H), 3.96-3.84 (m, 1H), 3.72-3.60 (m, 2H), 3.59-3.42 (m, 2H), 2.60-2.49 (m, 1H), 2.06-1.91 (m, 1H), 0.97 (d, J=6.8 Hz, 3H), 0.88 (d, J=6.9 Hz, 3H), 0.79 (d, J=6.7 Hz, 3H).

Compound 32 ((2R)-2-hydroxy-3-methyl-N-[(3R,4R)-4-methyl-1-[8-(trifluoromethyl)quinolin-5-yl]pyrrolidin-3-yl]butanamide)

From (3R,4R)-4-methyl-1-[8-(trifluoromethyl)quinolin-5-yl]pyrrolidin-3-amine (60 mg, 0.20 mmol) and (2S)-2-hydroxy-3-methylbutanoic acid, purified by prep-HPLC under the following conditions: column, XBridge Shield Prep C18 OBD column, 150 mm, 5 um; mobile phase, acetonitrile in water (with 10 mmol/L $NH_4HCO_3$ and 0.1% $NH_3.H_2O$), 40% to 56% gradient in 7 min; detector, UV 254 nm (42 mg, 52%, yellow solid). HPLC: 97.6% purity, RT=1.68 min. MS: m/z=396.2 $[M+H]^+$. $^1$H NMR (300 MHz, Methanol-$d_4$, ppm) δ 8.89-8.80 (m, 1H), 8.73 (d, J=8.8, 1.7 Hz, 1H), 7.91 (d, J=8.5 Hz, 1H), 7.53-7.42 (m, 1H), 6.87 (d, J=8.5 Hz, 1H), 4.64-4.55 (m, 1H), 4.03-3.86 (m, 2H), 3.77-3.64 (m, 1H), 3.61-3.43 (m, 2H), 2.75-2.59 (m, 1H), 2.14-1.97 (m, 1H), 1.11 (d, J=6.9 Hz, 3H), 0.98 (d, J=6.9 Hz, 3H), 0.80 (d, J=6.8 Hz, 3H).

Example 9: Synthesis of compounds 19 and 20 (N-[(3R,4R)-4-methyl-1-[8-(trifluoromethyl)quinolin-5-yl]pyrrolidin-3-yl]-2-[(3S)-1-methylpiperidin-3-yl]acetamide and N-[(3R,4R)-4-methyl-1-[8-(trifluoromethyl)quinolin-5-yl]pyrrolidin-3-yl]-2-[(3R)-1-methylpiperidin-3-yl]acetamide)

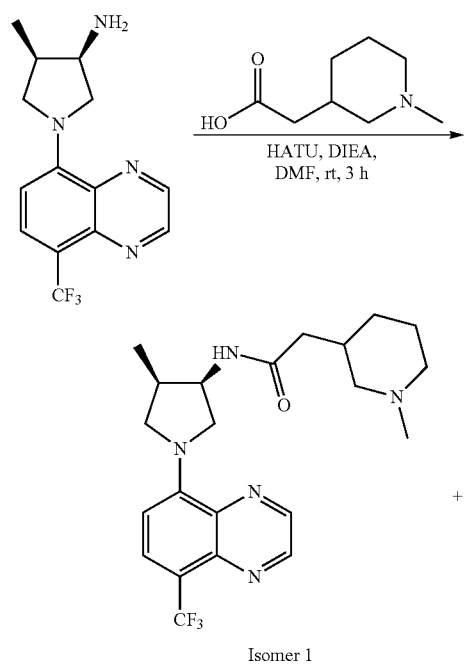

Isomer 1

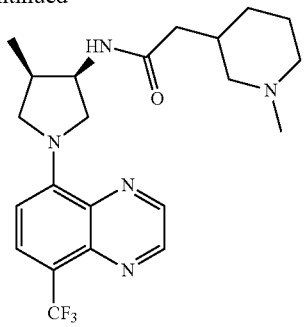

Isomer 2

N-[(3R,4R)-4-methyl-1-[8-(trifluoromethyl)quinolin-5-yl]pyrrolidin-3-yl]-2-[(3S)-1-methylpiperidin-3-yl]acetamide and N-[(3R,4R)-4-methyl-1-[8-(trifluoromethyl)quinolin-5-yl]pyrrolidin-3-yl]-2-[(3R)-1-methylpiperidin-3-yl]acetamide To a solution of (3R,4R)-4-methyl-1-[8-(trifluoromethyl)quinolin-5-yl]pyrrolidin-3-amine (119 mg, 0.40 mmol) in N,N-dimethylformamide (5 mL) were added 2-(1-methylpiperidin-3-yl)acetic acid (152 mg, 0.97 mmol), DIEA (76 mg, 0.59 mmol) and HATU (735 mg, 1.93 mmol) at room temperature. The resulting mixture was stirred for 3 h at room temperature. When the reaction was done, the reaction mixture was concentrated under reduced pressure and the residue was first purified by prep-HPLC under the following conditions: column, XBridge Prep C18 OBD Column, 150 mm, 5 um; mobile phase, acetonitrile in water (with 10 mmol/L $NH_4HCO_3$ and 0.1% $NH_3.H_2O$), 40% to 70% gradient in 7 min; detector, UV 254 nm. Then the two diastereomers were obtained by separation on chiral prep-HPLC under the following conditions: column, CHIRAL-PAK IG, 0.46×15 cm, 3 um; mobile phase, hexane (with 0.1% DEA) in EtOH, 88% isocratic in 30 min; detector, UV 254 nm.

Isomer 1:

(20 mg, 11%, yellow solid) HPLC: 97.8% purity, RT=2.39 min. MS: m/z=435.3 $[M+H]^+$. $^1$H NMR (300 MHz, DMSO-$d_6$, ppm) δ 8.95-8.87 (m, 1H), 8.70 (d, J=8.8, 1.7 Hz, 1H), 8.00-7.85 (m, 2H), 7.55-7.44 (m, 1H), 6.73 (d, J=8.5 Hz, 1H), 4.58-4.37 (m, 1H), 4.04-3.92 (m, 1H), 3.69-3.57 (m, 1H), 3.59-3.46 (m, 1H), 3.38-3.27 (m, 1H), 2.62-2.51 (m, 3H), 2.14-1.94 (m, 5H), 1.88-1.73 (m, 2H), 1.65-1.48 (m, 3H), 1.44-1.33 (m, 1H), 0.97 (d, J=6.7 Hz, 3H), 0.91-0.74 (m, 1H).

Isomer 2:

(25 mg, 14%, yellow solid) HPLC: 99.5% purity, RT=1.25 min. MS: m/z=435.3 $[M+H]^+$. $^1$H NMR (300 MHz, DMSO-$d_6$, ppm) δ 8.94-8.86 (m, 1H), 8.69 (d, 1H), 7.99-7.83 (m, 2H), 7.54-7.43 (m, 1H), 6.72 (d, J=8.6 Hz, 1H), 4.50-4.41 (m, 1H), 4.04-3.92 (m, 1H), 3.67-3.55 (m, 1H), 3.58-3.45 (m, 1H), 3.37-3.25 (m, 2H), 2.62-2.52 (m, 2H), 2.12-1.97 (m, 5H), 1.92-1.73 (m, 2H), 1.60-1.49 (m, 3H), 1.45-1.34 (m, 1H), 0.96 (d, J=6.8 Hz, 3H), 0.88-0.78 (m, 1H).

The following compounds were synthesized in an analogous manner:

Compounds 21 and 22 (N-[(3R,4R)-4-methyl-1-[8-(trifluoromethyl)quinolin-5-yl]pyrrolidin-3-yl]-2-[(3S)-1-methylpyrrolidin-3-yl]acetamide and N-[(3R,4R)-4-methyl-1-[8-(trifluoromethyl)quinolin-5-yl]pyrrolidin-3-yl]-2-[(3R)-1-methylpyrrolidin-3-yl]acetamide)

From (3R,4R)-4-methyl-1-[8-(trifluoromethyl)quinolin-5-yl]pyrrolidin-3-amine (109 mg, 0.37 mmol) and 2-(1-methylpyrrolidin-3-yl)acetic acid, purified by prep-HPLC under the following conditions: column, XBridge Prep C18 OBD Column, 150 mm, 5 um; mobile phase, acetonitrile in water (with 0.05% NH$_3$.H$_2$O), 39% to 54% gradient in 8 min; detector, UV 254 nm. The two diastereomers were obtained by separation on chiral prep-HPLC under the following conditions: column, CHIRALPAK IC-3, 0.46×15 cm, 3 um; mobile phase, hexane (with 0.1% DEA) in IPA, 50% isocratic in 30 min; detector, UV 254 nm. Isomer 1: (20 mg, 11%, yellow solid) HPLC: 99.5% purity, RT=2.87 min. MS: m/z=421.2 [M+H]$^+$. $^1$H NMR (300 MHz, DMSO-d$_6$, ppm) δ 8.95-8.86 (m, 1H), 8.69 (d, J=8.7, 1.7 Hz, 1H), 7.98 (d, J=8.3 Hz, 1H), 7.88 (d, J=8.5 Hz, 1H), 7.54-7.43 (m, 1H), 6.72 (d, J=8.5 Hz, 1H), 4.50-4.41 (m, 1H), 4.03-3.91 (m, 1H), 3.67-3.45 (m, 2H), 3.37-3.27 (m, 1H), 2.58-2.30 (m, 5H), 2.26-2.01 (m, 6H), 1.91-1.73 (m, 1H), 1.39-1.21 (m, 1H), 0.96 (d, J=6.7 Hz, 3H). Isomer 2: (20 mg, 11%, yellow solid) HPLC: 98.8% purity, RT=2.88 min. MS: m/z=421.1 [M+H]$^+$. $^1$H NMR (300 MHz, DMSO-d$_6$, ppm) δ 8.94-8.86 (m, 1H), 8.74-8.64 (m, 1H), 7.99 (d, J=8.3 Hz, 1H), 7.88 (d, J=8.5 Hz, 1H), 7.54-7.43 (m, 1H), 6.72 (d, J=8.5 Hz, 1H), 4.49-4.42 (m, 1H), 4.04-3.92 (m, 1H), 3.67-3.45 (m, 2H), 3.36-3.29 (m, 1H), 2.59-2.33 (m, 5H), 2.28-2.05 (m, 6H), 1.97-1.79 (m, 1H), 1.44-1.26 (m, 1H), 0.96 (d, J=6.8 Hz, 3H).

Compounds 29 and 30 ((2S)-2-cyclopropyl-2-hydroxy-N-[(3R,4R)-4-methyl-1-[8-(trifluoromethyl)quinolin-5-yl]pyrrolidin-3-yl]acetamide and (2R)-2-cyclopropyl-2-hydroxy-N-[(3R,4R)-4-methyl-1-[8-(trifluoromethyl)quinolin-5-yl]pyrrolidin-3-yl]acetamide)

From (3R,4R)-4-methyl-1-[8-(trifluoromethyl)quinolin-5-yl]pyrrolidin-3-amine and 2-cyclopropyl-2-hydroxyacetic acid, purified by prep-HPLC under the following conditions: column, XBridge Prep C18 OBD Column, 150 mm, 5 um; mobile phase, acetonitrile in water (with 10 mmol/L NH$_4$HCO$_3$ and 0.1% NH$_3$.H$_2$O), 35% to 52% gradient in 7 min; detector, UV 254 nm. The two diastereomers were obtained by separation on chiral prep-HPLC under the following conditions: column, CHIRALPAK IA-3, 0.46×15 cm, 3 um; mobile phase, hexane (with 0.1% DEA) in EtOH, 90% isocratic in 30 min; detector, UV 254 nm. Isomer 1: (25 mg, 19%, yellow solid) HPLC: 99.8% purity, RT=1.59 min. MS: m/z=394.1 [M+H]$^+$. $^1$H NMR (300 MHz, DMSO-d$_6$, ppm) δ 8.94-8.86 (m, 1H), 8.71 (d, J=8.7, 1.7 Hz, 1H), 7.89 (d, J=8.5 Hz, 1H), 7.74 (d, J=8.4 Hz, 1H), 7.54-7.43 (m, 1H), 6.73 (d, J=8.5 Hz, 1H), 4.53-4.46 (m, 1H), 4.02-3.89 (m, 1H), 3.72-3.60 (m, 1H), 3.55-3.40 (m, 3H), 2.60-2.51 (m, 1H), 1.09-0.93 (m, 4H), 0.43-0.21 (m, 4H). Isomer 2: (18 mg, 10%, yellow solid) HPLC: 99.7% purity, RT=2.30 min. MS: m/z=394.1 [M+H]$^+$. $^1$H NMR (300 MHz, Methanol-d$_4$, ppm) δ 8.89-8.80 (m, 1H), 8.75 (d, J=8.8, 1.7 Hz, 1H), 7.91 (d, J=8.4 Hz, 1H), 7.53-7.42 (m, 1H), 6.88 (d, J=8.4 Hz, 1H), 4.66-4.59 (m, 1H), 4.03-3.91 (m, 1H), 3.76-3.63 (m, 2H), 3.60-3.43 (m, 2H), 2.75-2.59 (m, 1H), 1.24-1.07 (m, 4H), 0.57-0.37 (m, 4H).

Example 10: Synthesis of compound 25 (2-(4-fluoropiperidin-4-yl)-N-[(3R,4R)-4-methyl-1-[8-(trifluoromethyl)quinolin-5-yl]pyrrolidin-3-yl]acetamide)

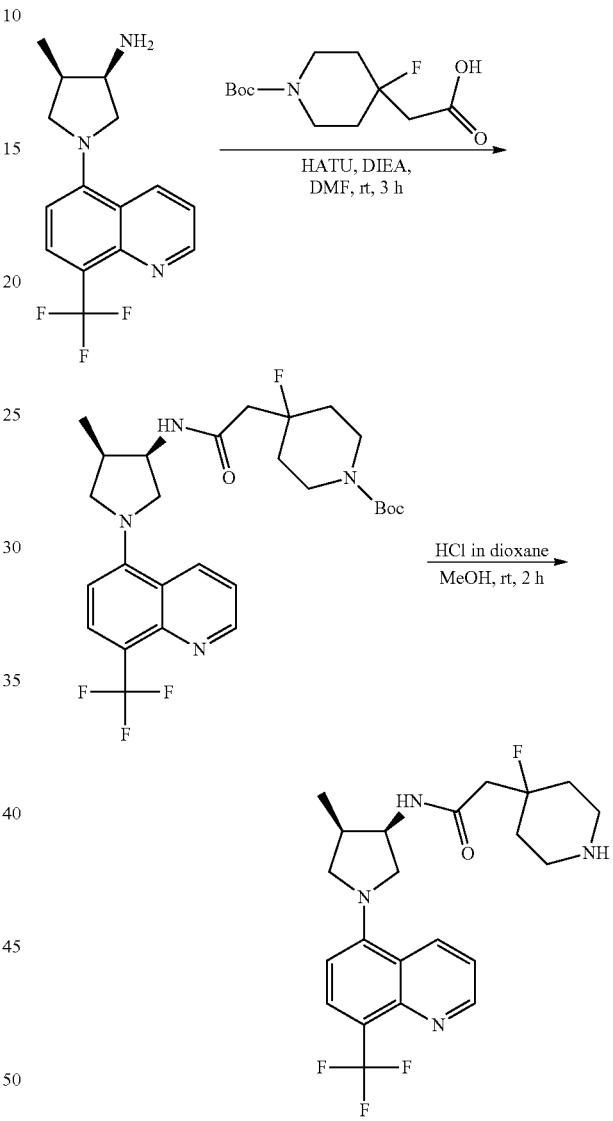

tert-butyl 4-fluoro-4-([[(3R,4R)-4-methyl-1-[8-(trifluoromethyl)quinolin-5-yl]pyrrolidin-3-yl]carbamoyl]methyl)piperidine-1-carboxylate To a solution of (3R,4R)-4-methyl-1-[8-(trifluoromethyl)quinolin-5-yl]pyrrolidin-3-amine (48 mg, 0.16 mmol) in N,N-dimethylformamide (1 mL) were added 2-[1-[(tert-butoxy)carbonyl]-4-fluoropiperidin-4-yl]acetic acid (82 mg, 0.31 mmol), DIEA (31 mg, 0.24 mmol) and HATU (307 mg, 0.81 mmol) at the room temperature. The resulting solution was stirred for 3 h at room temperature. When the reaction was done, the reaction mixture was diluted with water (10 mL) and the resulting mixture was extracted with ethyl acetate (30 mL×3). The organic phases were combined, washed with brine and dried over Na₂SO₄. The solvent was removed under reduced pressure to yield tert-butyl 4-fluoro-4-([[(3R,4R)-4-methyl-1-[8-(trifluoromethyl)quinolin-5-yl]pyrrolidin-3-yl]carbamoyl]methyl)piperidine-1-carboxylate as yellow solid (80 mg, crude).

2-(4-fluoropiperidin-4-yl)-N-[(3R,4R)-4-methyl-1-[8-(trifluoromethyl)quinolin-5-yl]pyrrolidin-3-yl]acetamide To a solution of tert-butyl 4-fluoro-4-([[(3R,4R)-4-methyl-1-[8-(trifluoromethyl)quinolin-5-yl]pyrrolidin-3-yl]carbamoyl]methyl)piperidine-1-carboxylate (80 mg, crude) in methanol (3 mL) was added hydrogen chloride solution (6 N in dioxane, 2 mL, 12 mmol) at the room temperature. The resulting mixture was stirred for 2 h at room temperature. When the reaction was done, the reaction mixture was concentrated under reduced pressure and the residue was purified by prep-HPLC under the following conditions: column, XBridge Shield Prep C18 OBD column, 150 mm, 5 um, 13 nm; mobile phase, acetonitrile in water (with 10 mmol/L NH₄HCO₃ and 0.1% NH₃.H₂O), 32% to 38% gradient in 7 min; detector, UV 254 nm. 2-(4-fluoropiperidin-4-yl)-N-[(3R,4R)-4-methyl-1-[8-(trifluoromethyl)quinolin-5-yl]pyrrolidin-3-yl]acetamide was obtained as yellow solid (12 mg, 1.3% for 2 steps).

Compound 25

HPLC: 95.2% purity, RT=2.93 min. MS: m/z=439.4 [M+H]⁺. ¹H NMR (300 MHz, DMSO-d₆, ppm) δ 8.86-8.78 (m, 1H), 8.61 (d, J=8.8 Hz, 1H), 7.80 (d, J=8.5 Hz, 1H), 7.67 (d, J=7.5 Hz, 1H), 7.45-7.34 (m, 1H), 6.70 (d, J=8.4 Hz, 1H), 4.52-4.43 (m, 1H), 4.10-3.90 (m, 1H), 3.63-3.45 (m, 3H), 2.81-2.60 (m, 4H), 2.40-2.20 (m, 4H), 1.85-1.55 (m, 4H), 1.05-0.85 (m, 3H).

Example 11: Synthesis of compound 26 (2-(4-fluoro-1-methylpiperidin-4-yl)-N-[(3R,4R)-4-methyl-1-[8-(trifluoromethyl)quinolin-5-yl]pyrrolidin-3-yl]acetamide)

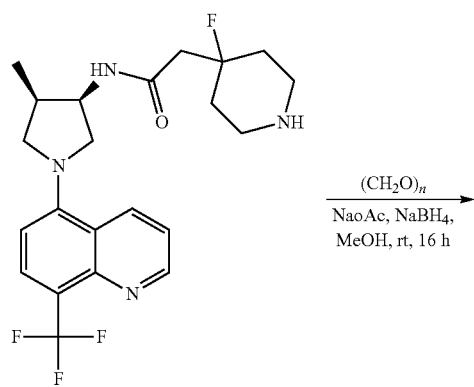

(CH₂O)ₙ
NaOAc, NaBH₄,
MeOH, rt, 16 h

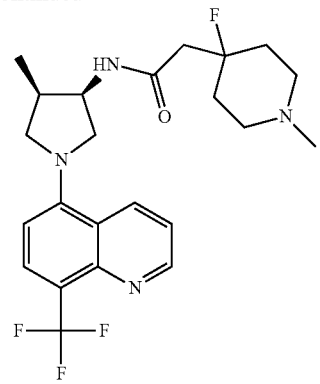

2-(4-fluoro-1-methylpiperidin-4-yl)-N-[(3R,4R)-4-methyl-1-[8-(trifluoromethyl)quinolin-5-yl]pyrrolidin-3-yl]acetamide To a solution of 2-(4-fluoropiperidin-4-yl)-N-[(3R,4R)-4-methyl-1-[8-(trifluoromethyl)quinolin-5-yl]pyrrolidin-3-yl]acetamide (48 mg, 0.11 mmol) in methanol (3 mL) was added (CH₂O)ₙ(95 mg, 1.05 mmol), NaOAC (190 mg, 2.32 mmol) and NaBH₄ (66 mg, 1.76 mmol) at the room temperature. The resulting mixture was stirred for 12 h at room temperature. When the reaction was done, it was quenched by the addition of water (5 mL). The resulting mixture was extracted with ethyl acetate (30 mL×3). The organic phases were combined, washed with brine and dried over Na₂SO₄. The solvent was removed under reduced pressure and the residue was purified by prep-HPLC under the following conditions: column, XBridge Shield Prep C18 OBD column, 150 mm, 5 um, 13 nm; mobile phase, acetonitrile in water (with 10 mmol/L NH₄HCO₃ and 0.1% NH₃.H₂O), 30% to 55% gradient in 7 min; detector, UV 254 nm. 2-(4-fluoro-1-methylpiperidin-4-yl)-N-[(3R,4R)-4-methyl-1-[8-(trifluoromethyl)quinolin-5-yl]pyrrolidin-3-yl]acetamide was obtained as yellow solid (20 mg, 40%).

Compound 26

HPLC: 98.3% purity, RT=3.39 min. MS: m/z=453.5 [M+H]⁺. ¹H NMR (300 MHz, Methanol-d₄, ppm) δ 8.88-8.79 (m, 1H), 8.74 (d, J=8.8, 1.7 Hz, 1H), 7.90 (d, J=8.5 Hz, 1H), 7.51-7.40 (m, 1H), 6.83 (d, J=8.5 Hz, 1H), 4.65-4.54 (m, 1H), 4.05-3.93 (m, 1H), 3.72-3.60 (m, 1H), 3.62-3.49 (m, 1H), 3.47-3.36 (m, 1H), 2.74-2.45 (m, 5H), 2.40-2.26 (m, 5H), 1.95-1.89 (m, 3H), 1.98-1.75 (m, 1H), 1.09 (d, J=6.8 Hz, 3H).

Example 12: Synthesis of compounds 27 and 28 (2-[(4S)-3,3-difluoro-1-methylpiperidin-4-yl]-N-[(3R,4R)-4-methyl-1-[8-(trifluoromethyl)quinolin-5-yl]pyrrolidin-3-yl]acetamide and 2-[(4R)-3,3-difluoro-1-methylpiperidin-4-yl]-N-[(3R,4R)-4-methyl-1-[8-(trifluoromethyl)quinolin-5-yl]pyrrolidin-3-yl]acetamide)

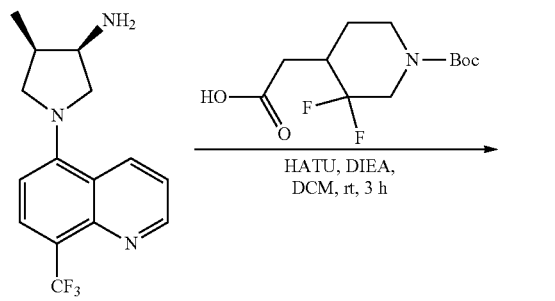

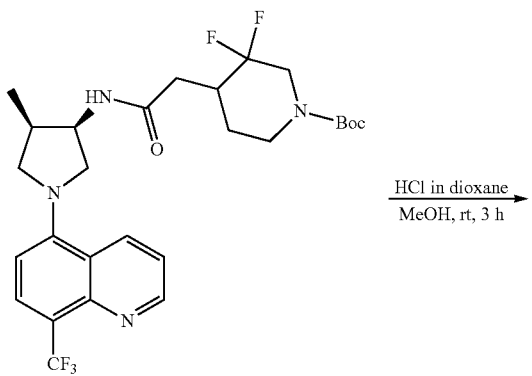

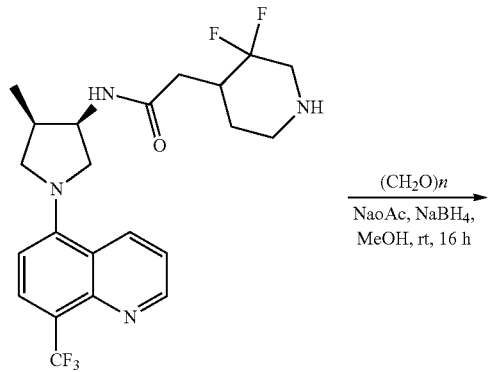

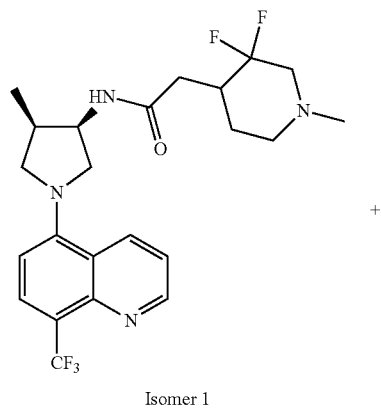

Isomer 1

+

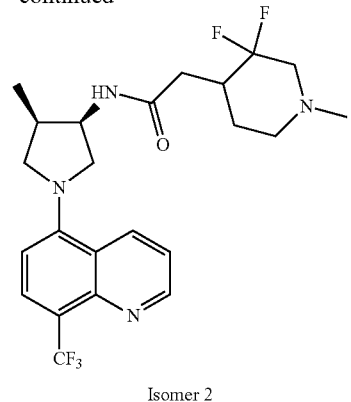

Isomer 2 tert-butyl 3,3-difluoro-4-([[[(3R,4R)-4-methyl-1-[8-(trifluoromethyl)quinolin-5-yl]pyrrolidin-3-yl]carbamoyl]methyl)piperidine-1-carboxylate To a solution of (3R,4R)-4-methyl-1-[8-(trifluoromethyl)quinolin-5-yl]pyrrolidin-3-amine (50 mg, 0.17 mmol) in dichloromethane (3 mL) were added 2-[1-[(tert-butoxy)carbonyl]-3,3-difluoropiperidin-4-yl]acetic acid (62 mg, 0.22 mmol), DIEA (32 mg, 0.24 mmol) and HATU (307 mg, 0.81 mmol) at room temperature. The resulting solution was stirred for 3 h at room temperature. When the reaction was done, it was quenched by the addition of water (10 mL). The resulting mixture was extracted with ethyl acetate (50 mL×3). The organic phases were combined, washed with brine and dried over $Na_2SO_4$. The solution was concentrated under reduced pressure to yield 3,3-difluoro-4-([[[(3R,4R)-4-methyl-1-[8-(trifluoromethyl)quinolin-5-yl]pyrrolidin-3-yl]carbamoyl]methyl)piperidine-1-carboxylate as a yellow solid (80 mg, crude). MS: m/z=557.5 $[M+H]^+$.

tert-butyl 3,3-difluoro-4-([[[(3R,4R)-4-methyl-1-[8-(trifluoromethyl)quinolin-5-yl]pyrrolidin-3-yl]carbamoyl]methyl)piperidine-1-carboxylate To a solution of tert-butyl 3,3-difluoro-4-([[[(3R,4R)-4-methyl-1-[8-(trifluoromethyl)quinolin-5-yl]pyrrolidin-3-yl]carbamoyl]methyl)piperidine-1-carboxylate (80 mg, crude) in methanol (3 mL) was added hydrogen chloride solution (6 N in dioxane, 2 mL, 12 mmol) at room temperature. The resulting mixture was stirred for 3 h at room temperature. When the reaction was done, it was quenched by the addition of water (10 mL). The pH value of the resulting mixture was adjusted to 8 with sat. $NaHCO_3$ solution. The resulting mixture was extracted with ethyl acetate (50 mL×3). The organic phases were combined, washed with brine and dried over $Na_2SO_4$. The solvent was removed under reduced pressure to yield 2-(3,3-difluoropiperidin-4-yl)-N-[(3R,4R)-4-methyl-1-[8-(trifluoromethyl)quinolin-5-yl]pyrrolidin-3-yl]acetamide as a yellow solid (60 mg, crude). MS: m/z=557.5 $[M+H]^+$.

2-[(4S)-3,3-difluoro-1-methylpiperidin-4-yl]-N-[(3R,4R)-4-methyl-1-[8-(trifluoromethyl)quinolin-5-yl]pyrrolidin-3-yl]acetamide and 2-[(4R)-3,3-difluoro-1-methylpiperidin-4-yl]-N-[(3R,4R)-4-methyl-1-[8-(trifluoromethyl)quinolin-5-yl]pyrrolidin-3-yl]acetamide To a solution of 2-(3,3-difluoropiperidin-4-yl)-N-[(3R,4R)-4-methyl-1-[8-(trifluoromethyl)quinolin-5-yl]pyrrolidin-3-yl]acetamide (60 mg, crude) in methanol (4 mL) was added (CH$_2$O)$_n$(110 mg, 2.45 mmol), NaOAC (200 mg, 4.86 mmol) and NaBH$_4$ (72 mg, 3.79 mmol) at room temperature. The resulting mixture was stirred for 16 h at room temperature. When the reaction was done, the reaction mixture was concentrated under reduced pressure and the residue was first purified by prep-HPLC under the following conditions: column, XBridge Prep C18 OBD Column, 150 mm, 5 um; mobile phase, acetonitrile in water (with 10 mmol/L NH$_4$HCO$_3$ and 0.1% NH$_3$.H$_2$O), 35% to 50% gradient in 8 min; detector, UV 254 nm. Then the two diastereomers were obtained by separation on chiral prep-HPLC under the following conditions: column, CHIRALPAK IC-3, 0.46×15 cm, 3 um; mobile phase, hexane (with 0.1% DEA) in IPA, 50% isocratic in 20 min; detector, UV 254 nm.

Isomer 1:

(12 mg, 15% for 3 steps, off-white solid) HPLC: 99.0% purity, RT=3.06 min. MS: m/z=471.5 [M+H]$^+$. $^1$H NMR (300 MHz, DMSO-d$_6$, ppm) δ 8.96-8.87 (m, 1H), 8.75-8.65 (m, 1H), 8.12 (d, J=8.4 Hz, 1H), 7.90 (d, J=8.4 Hz, 1H), 7.55-7.44 (m, 1H), 6.73 (d, J=8.5 Hz, 1H), 4.51-4.42 (m, 1H), 4.06-3.94 (m, 1H), 3.68-3.46 (m, 2H), 2.98-2.86 (m, 1H), 2.67-2.56 (m, 1H), 2.50-2.44 (m, 2H), 2.29-2.02 (m, 7H), 1.98-1.84 (m, 1H), 1.64-1.52 (m, 1H), 1.38-1.20 (m, 1H), 0.98 (d, J=6.7 Hz, 3H).

Isomer 2:

(12 mg, 15% for 3 steps, yellow solid) HPLC: 99.5% purity, RT=3.01 min. MS: m/z=471.5 [M+H]$^+$. $^1$H NMR (300 MHz, DMSO-d$_6$, ppm) δ 9.01-8.93 (m, 1H), 8.83-8.71 (m, 1H), 8.20 (d, J=8.4 Hz, 1H), 7.95 (d, J=8.5 Hz, 1H), 7.61-7.50 (m, 1H), 6.79 (d, J=8.6 Hz, 1H), 4.64-4.40 (m, 1H), 4.10-3.98 (m, 1H), 3.74-3.62 (m, 1H), 3.65-3.52 (m, 1H), 3.14-2.83 (m, 2H), 2.82-2.71 (m, 1H), 2.53-2.47 (m, 1H), 2.38-1.88 (m, 8H), 1.81-1.70 (m, 1H), 1.52-1.34 (m, 1H), 1.02 (d, J=6.7 Hz, 3H).

Example 13: Synthesis of compound 33 ((3R,4R)-4-methyl-1-(8-methylquinolin-5-yl)pyrrolidin-3-amine)

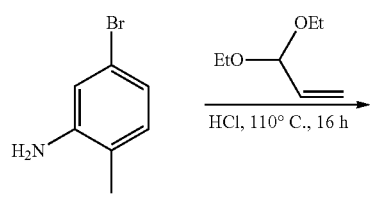

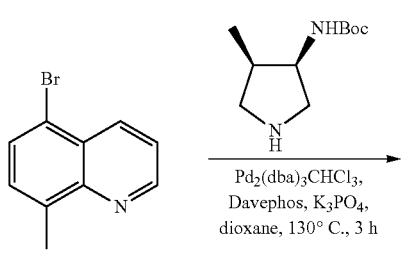

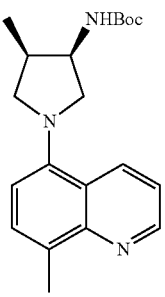

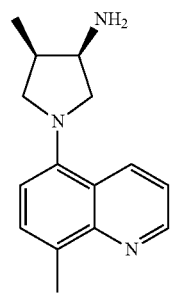

5-bromo-8-methylquinoline

To a mixture of 5-bromo-2-methylaniline (980 mg, 5.27 mmol) in HCl solution (2 M, 30 mL) was added 3,3-diethoxyprop-1-ene (1.67 g, 12.80 mmol) at room temperature. The resulting mixture was stirred for 16 h at 110° C. When the reaction was done, the pH value of the reaction mixture was adjusted to 7-8 with sodium bicarbonate solution (4 M). The resulting mixture was extracted with DCM (100 mL×3). The organic phases were combined, washed with brine and dried over Na$_2$SO$_4$. The organic phases were combined, washed with brine and dried over Na$_2$SO$_4$. The solvent was removed under reduced pressure and the residue was purified by flash chromatography eluting with EtOAc in hexane (0% to 70% gradient) to yield 5-bromo-8-methylquinoline as yellow solid (360 mg, 30%). MS: m/z=223.9 [M+H]$^+$.

tert-butyl N-[(3R,4R)-4-methyl-1-(8-methylquinolin-5-yl)pyrrolidin-3-yl]carbamate To a solution of 5-bromo-8-methylquinoline (360 mg, 1.62 mmol) in N,N-dimethylformamide (10 mL) was added tert-butyl N-[(3R,4R)-4-methylpyrrolidin-3-yl]carbamate (342 mg, 1.71 mmol), Pd$_2$(dba)$_3$CHCl$_3$ (177 mg, 0.17 mmol), K$_3$PO$_4$ (1088 mg, 5.12 mmol) and Davephos (135 mg, 0.34 mmol) at room temperature. The resulting mixture was stirred for 3 h at 130° C. When the reaction was done, it was quenched by the addition of water (20 mL). The resulting mixture was extracted with DCM (100 mL×3). The organic phases were combined, washed with brine and dried over Na$_2$SO$_4$. The organic phases were combined, washed with brine and dried over Na$_2$SO$_4$. The solvent was removed under reduced pressure and the residue was purified by flash chromatography eluting with EtOAc in hexane (0% to 25% gradient) to yield tert-butyl N-[(3R,4R)-4-methyl-1-(8-methylquinolin-5-yl)pyrrolidin-3-yl]carbamate as yellow oil (400 mg, 72%). MS: m/z=342.2 [M+H]$^+$.

(3R,4R)-4-methyl-1-(8-methylquinolin-5-yl)pyrrolidin-3-amine

To a solution of tert-butyl N-[(3R,4R)-4-methyl-1-(8-methylquinolin-5-yl)pyrrolidin-3-yl]carbamate (200 mg, 0.59 mmol) in methanol (5 mL) was added hydrogen chloride solution (4 M in dioxane, 3 mL, 12 mmol) at room temperature. The resulting mixture was stirred for 1 h at room temperature. When the reaction was done, the reaction mixture was concentrated under reduced pressure and the residue was purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 5% to 60% gradient in 7 min; detector, UV 254 nm. (3R,4R)-4-methyl-1-(8-methylquinolin-5-yl)pyrrolidin-3-amine was obtained as yellow solid (60 mg, 42%).

Compound 33

HPLC: 99.5% purity, RT=1.07 min. MS: m/z=242.3 [M+H]$^+$. $^1$H NMR (300 MHz, Methanol-d$_4$, ppm) δ 8.82-8.74 (m, 1H), 8.71-8.61 (m, 1H), 7.48-7.37 (m, 2H), 6.92 (d, J=7.9 Hz, 1H), 3.77-3.65 (m, 1H), 3.62-3.51 (m, 1H), 3.50-3.38 (m, 1H), 3.37-3.25 (m, 1H), 3.23-3.12 (m, 1H), 2.63 (s, 3H), 2.56-2.40 (m, 1H), 1.14 (d, J=7.0 Hz, 3H).

Example 14: Synthesis of compound 34 (N-[(3R,4R)-4-methyl-1-(8-methylquinolin-5-yl)pyrrolidin-3-yl]-2-(1-methylpiperidin-4-yl)acetamide)

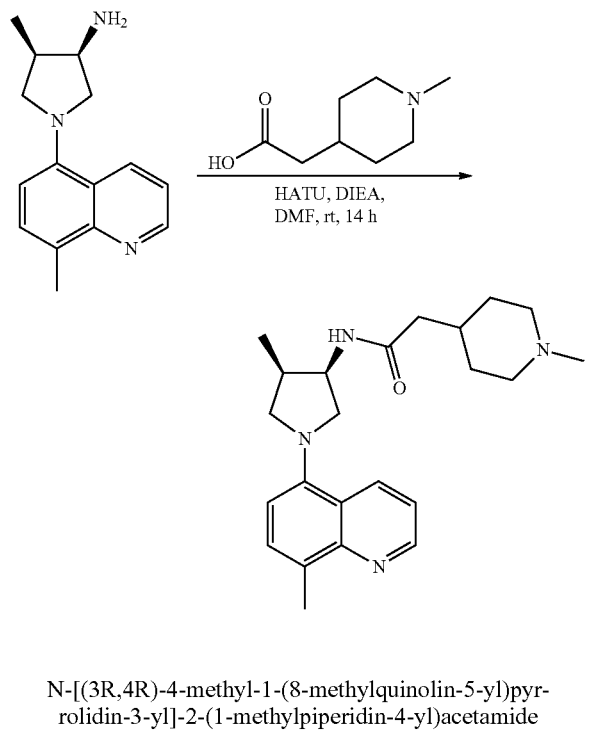

N-[(3R,4R)-4-methyl-1-(8-methylquinolin-5-yl)pyrrolidin-3-yl]-2-(1-methylpiperidin-4-yl)acetamide To a solution of (3R,4R)-4-methyl-1-(8-methylquinolin-5-yl)pyrrolidin-3-amine (40 mg, 0.16 mmol) in N-dimethylformamide (2 mL) were added 2-(1-methylpiperidin-4-yl)acetic acid (38 mg, 0.24 mmol), HATU (91 mg, 0.24 mmol) and DIEA (101 mg, 0.78 mmol) at room temperature. The resulting solution was stirred for 14 h at room temperature. When the reaction was done, the reaction mixture was concentrated under reduced pressure and the residue was purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 5% to 61% gradient in 7 min; detector, UV 254 nm. N-[(3R,4R)-4-methyl-1-(8-methylquinolin-5-yl)pyrrolidin-3-yl]-2-(1-methylpiperidin-4-yl)acetamide was obtained as yellow solid (20 mg, 31%).

Compound 34

HPLC: 97.4% purity, RT=2.79 min. MS: m/z=381.4 [M+H]$^+$. $^1$H NMR (300 MHz, Methanol-d$_4$, ppm) δ 8.84-8.75 (m, 1H), 8.73-8.59 (m, 1H), 7.50-7.39 (m, 2H), 6.96 (d, J=7.8 Hz, 1H), 4.68-4.56 (m, 1H), 3.80-3.68 (m, 1H), 3.51-3.39 (m, 1H), 3.32-3.19 (m, 1H), 3.21-3.10 (m, 1H), 2.90-2.78 (m, 2H), 2.71-2.52 (m, 4H), 2.30-2.12 (m, 5H), 2.09-1.93 (m, 2H), 1.88-1.62 (m, 3H), 1.42-1.17 (m, 2H), 1.06 (d, J=7.0 Hz, 3H).

The following compounds were synthesized in an analogous manner:

Compound 39 (N-[(3R,4R)-4-methyl-1-(8-methylquinolin-5-yl)pyrrolidin-3-yl]-2-(morpholin-4-yl)acetamide)

From (3R,4R)-4-methyl-1-(8-methylquinolin-5-yl)pyrrolidin-3-amine and 2-(morpholin-4-yl)acetic acid, purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 20% to 50% gradient in 8 min; detector, UV 254 nm (20 mg, 24%, yellow solid). HPLC: 99.1% purity, RT=1.29 min. MS: m/z=369.4 [M+H]$^+$. $^1$H NMR (300 MHz, Methanol-d$_4$, ppm) δ 8.85-8.76 (m, 1H), 8.69-8.59 (m, 1H), 7.52-7.41 (m, 2H), 7.00 (d, J=7.8 Hz, 1H), 4.66-4.54 (m, 1H), 3.81-3.64 (m, 5H), 3.50-3.37 (m, 1H), 3.31-3.11 (m, 3H), 3.12-2.99 (m, 2H), 2.78-2.57 (m, 4H), 2.62-2.45 (m, 4H), 1.08 (d, J=7.0 Hz, 3H).

Compound 40 (2-(1,4-dimethylpiperidin-4-yl)-N-[(3R,4R)-4-methyl-1-(8-methylquinolin-5-yl)pyrrolidin-3-yl]acetamide)

From (3R,4R)-4-methyl-1-(8-methylquinolin-5-yl)pyrrolidin-3-amine and 2-(1,4-dimethylpiperidin-4-yl)acetic acid, purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 30% to 60% gradient in 8 min; detector, UV 254 nm (10 mg, 15%, light yellow solid). HPLC: 97.3% purity, RT=2.30 min. MS: m/z=395.4 [M+H]$^+$. $^1$H NMR (300 MHz, DMSO-d$_6$, ppm) δ 8.83-8.74 (m, 1H), 8.54-8.44 (m, 1H), 7.83 (d, J=8.3 Hz, 1H), 7.42-7.31 (m, 2H), 6.77 (d, J=7.7 Hz, 1H), 4.49-4.34 (m, 1H), 3.68-3.57 (m, 1H), 3.40-3.31 (m, 2H), 3.23-3.11 (m, 1H), 3.07-2.96 (m, 1H), 2.55-2.49 (m, 4H), 2.45-2.31 (m, 2H), 2.23 (s, 3H), 2.15-1.98 (m, 2H), 1.60-1.47 (m, 2H), 1.39-1.25 (m, 2H), 1.20-1.13 (m, 1H), 0.92-0.88 (m, 6H).

Compound 47 ((2S)-2-hydroxy-3-methyl-N-[(3R,4R)-4-methyl-1-(8-methylquinolin-5-yl)pyrrolidin-3-yl]butanamide)

From (3R,4R)-4-methyl-1-(8-methylquinolin-5-yl)pyrrolidin-3-amine and (2S)-2-hydroxy-3-methylbutanoic acid, purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 35% to 45% gradient in 7 min; detector, UV 254 nm (20 mg, 24%, orange solid). HPLC: 99.6% purity, RT=1.40 min. MS: m/z=342.4 [M+H]$^+$. $^1$H NMR (300 MHz, Methanol-d$_4$, ppm) δ 8.85-8.77 (m, 1H), 8.71-8.61 (m, 2H), 7.53-7.42 (m, 2H), 7.00 (d, J=7.8 Hz, 1H), 4.70-4.58 (m, 1H), 3.94-3.86 (m, 1H), 3.80-3.68 (m, 1H), 3.53-3.40 (m, 1H), 3.32-3.16 (m, 2H), 2.76-2.60 (m, 4H), 2.22-2.05 (m, 1H), 1.10 (d, J=7.0 Hz, 3H), 1.03 (d, J=7.0 Hz, 3H), 0.92 (d, J=6.8 Hz, 3H).

Compound 48 ((2R)-2-hydroxy-3-methyl-N-[(3R,4R)-4-methyl-1-(8-methylquinolin-5-yl)pyrrolidin-3-yl]butanamide)

From (3R,4R)-4-methyl-1-(8-methylquinolin-5-yl)pyrrolidin-3-amine and (2R)-2-hydroxy-3-methylbutanoic acid, purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 35% to 45% gradient in 7 min; detector, UV 254 nm (23 mg, 29%, orange solid). HPLC: 99.7% purity, RT=1.39 min. MS: m/z=342.4 [M+H]$^+$. $^1$H NMR (300 MHz, Methanol-d$_4$, ppm) δ 8.85-8.77 (m, 1H), 8.70-8.60 (m, 1H), 7.52-7.41 (m, 2H), 7.01 (d, J=7.8 Hz, 1H), 4.69-4.56 (m, 1H), 3.94 (d, J=3.6 Hz, 1H), 3.79-3.67 (m, 1H), 3.53-3.41 (m, 1H), 3.31-3.15 (m, 2H), 2.77-2.62 (m, 4H), 2.18-2.00 (m, 1H), 1.10 (d, J=7.0 Hz, 3H), 1.01 (d, J=6.9 Hz, 3H), 0.84 (d, J=6.8 Hz, 3H).

Example 15: Synthesis of compounds 35 and 36 (N-[(3R,4R)-4-methyl-1-(8-methylquinolin-5-yl)pyrrolidin-3-yl]-2-[(3S)-1-methylpiperidin-3-yl]acetamide and N-[(3R,4R)-4-methyl-1-(8-methylquinolin-5-yl)pyrrolidin-3-yl]-2-[(3R)-1-methylpiperidin-3-yl]acetamide)

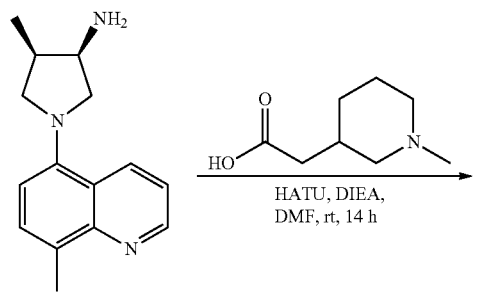

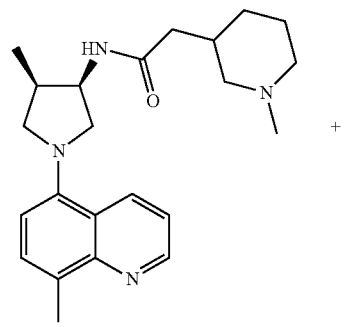

Isomer 1

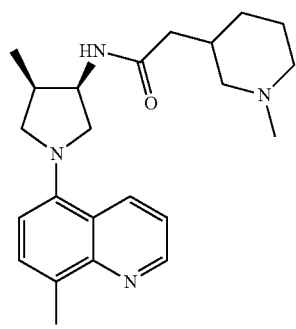

Isomer 2

N-[(3R,4R)-4-methyl-1-(8-methylquinolin-5-yl)pyrrolidin-3-yl]-2-[(3S)-1-methylpiperidin-3-yl]acetamide and N-[(3R,4R)-4-methyl-1-(8-methylquinolin-5-yl)pyrrolidin-3-yl]-2-[(3R)-1-methylpiperidin-3-yl]acetamide To a solution of (3R,4R)-4-methyl-1-(8-methylquinolin-5-yl)pyrrolidin-3-amine (49 mg, 0.20 mmol) in N,N-dimethylformamide (3 mL) was added 2-(1-methylpiperidin-3-yl)acetic acid (46 mg, 0.30 mmol), HATU (120 mg, 0.30 mmol) and DIEA (126 mg, 0.98 mmol) at room temperature. The resulting solution was stirred for 14 h at room temperature. When the reaction was done, the reaction mixture was concentrated under reduced pressure and the residue was first purified by prep-HPLC under the following conditions: column, XBridge Prep C18 OBD Column, 150 mm, 5 um; mobile phase, acetonitrile in water (with 10 mmol/L NH$_4$HCO$_3$ and 0.1% NH$_3$.H$_2$O), 20% to 57% gradient in 7 min; detector, UV 254 nm. Then the two diastereomers were obtained by separation on chiral prep-HPLC under the following conditions: column, CHIRALPAK IG-3, 0.46×10 cm, 3 um; mobile phase, hexane (with 0.1% DEA) in EtOH, 80% isocratic in 30 min; detector, UV 254 nm.

Isomer 1:

(15 mg, 19%, red solid) HPLC: 99.8% purity, RT=1.31 min. MS: m/z=381.2 [M+H]$^+$. $^1$H NMR (300 MHz, Methanol-d$_4$, ppm) δ 8.84-8.75 (m, 1H), 8.72-8.62 (m, 1H), 7.50-7.39 (m, 2H), 6.96 (d, J=7.8 Hz, 1H), 4.68-4.56 (m, 1H), 3.81-3.69 (m, 1H), 3.51-3.39 (m, 1H), 3.30-3.09 (m, 4H), 2.72-2.51 (m, 8H), 2.51-2.37 (m, 1H), 2.31-2.09 (m, 3H), 1.91-1.65 (m, 3H), 1.24-1.10 (m, 1H), 1.07 (d, J=6.9 Hz, 3H).

Isomer 2:

(18 mg, 10%, yellow solid) HPLC: 99.5% purity, RT=1.30 min. MS: m/z=381.2 [M+H]$^+$. $^1$H NMR (300 MHz, Methanol-d$_4$, ppm) δ 8.84-8.75 (m, 1H), 8.73-8.63 (m, 1H), 7.51-7.40 (m, 2H), 6.96 (d, J=7.8 Hz, 1H), 4.69-4.56 (m, 1H), 3.82-3.70 (m, 1H), 3.51-3.35 (m, 2H), 3.38-3.31 (m, 1H), 3.30-3.21 (m, 1H), 3.21-3.10 (m, 1H), 2.83-2.69 (m, 4H), 2.72-2.54 (m, 5H), 2.38-2.21 (m, 3H), 2.00-1.83 (m, 2H), 1.86-1.65 (m, 1H), 1.31-1.13 (m, 1H), 1.07 (d, J=6.9 Hz, 3H).

The following compounds were synthesized in an analogous manner:

Compounds 37 and 38 (N-[(3R,4R)-4-methyl-1-(8-methylquinolin-5-yl)pyrrolidin-3-yl]-2-[(3S)-1-methylpyrrolidin-3-yl]acetamide and N-[(3R,4R)-4-methyl-1-(8-methylquinolin-5-yl)pyrrolidin-3-yl]-2-[(3R)-1-methylpyrrolidin-3-yl]acetamide)

From (3R,4R)-4-methyl-1-(8-methylquinolin-5-yl)pyrrolidin-3-amine and 2-(1-methylpyrrolidin-3-yl)acetic acid, purified by prep-HPLC under the following conditions: column, XBridge Prep C18 OBD Column, 150 mm, 5 um; mobile phase, acetonitrile in water (with 10 mmol/L NH$_4$HCO$_3$ and 0.1% NH$_3$.H$_2$O), 20% to 47% gradient in 8 min; detector, UV 254 nm. The two isomers were obtained by separation on chiral prep-HPLC under the following conditions: column, CHIRALPAK IG-3, 0.46×10 cm, 3 um; mobile phase, MtBE (with 0.1% DEA) in EtOH, 70% isocratic in 30 min; detector, UV 254 nm. Isomer 1: (25 mg, 26%, red solid) HPLC: 97.7% purity, RT=2.14 min. MS: m/z=367.4 [M+H]$^+$. $^1$H NMR (400 MHz, DMSO-d$_6$, ppm) δ 8.89-8.83 (m, 1H), 8.60-8.48 (m, 1H), 7.95 (d, J=8.5 Hz, 1H), 7.48-7.40 (m, 2H), 6.84 (d, J=7.8 Hz, 1H), 4.54-4.43 (m, 1H), 3.74-3.65 (m, 1H), 3.50-3.35 (m, 1H), 3.28-3.18

(m, 1H), 3.13-3.02 (m, 1H), 2.65-2.30 (m, 8H), 2.27-2.05 (m, 6H), 1.94-1.80 (m, 1H), 1.41-1.28 (m, 1H), 0.95 (d, J=6.9 Hz, 3H). Isomer 2: (25 mg, 26%, yellow solid) HPLC: 95.2% purity, RT=2.16 min. MS: m/z=367.4 [M+H]+. $^1$H NMR (400 MHz, DMSO-d$_6$, ppm) δ 8.89-8.83 (m, 1H), 8.60-8.53 (m, 1H), 7.96 (d, J=8.5 Hz, 1H), 7.48-7.40 (m, 2H), 6.84 (d, J=7.8 Hz, 1H), 4.54-4.43 (m, 1H), 3.74-3.65 (m, 1H), 3.44-3.35 (m, 1H), 3.28-3.19 (m, 1H), 3.12-3.04 (m, 1H), 2.62-2.57 (m, 3H), 2.57-2.50 (m, 1H), 2.49-2.37 (m, 4H), 2.20 (d, J=9.5 Hz, 5H), 2.15-2.06 (m, 1H), 1.97-1.83 (m, 1H), 1.44-1.31 (m, 1H), 0.95 (d, J=6.8 Hz, 3H).

Compounds 45 and 46 ((2S)-2-cyclopropyl-2-hydroxy-N-[(3R,4R)-4-methyl-1-(8-methylquinolin-5-yl)pyrrolidin-3-yl]acetamide and (2R)-2-cyclopropyl-2-hydroxy-N-[(3R,4R)-4-methyl-1-(8-methylquinolin-5-yl)pyrrolidin-3-yl]acetamide)

From (3R,4R)-4-methyl-1-(8-methylquinolin-5-yl)pyrrolidin-3-amine and 2-cyclopropyl-2-hydroxyacetamide, purified by prep-HPLC under the following conditions: column, XBridge RP18 OBD Column, 150 mm, 5 um; mobile phase, acetonitrile in water (with 10 mmol/L NH$_4$HCO$_3$ and 0.1% NH$_3$.H$_2$O), 20% to 50% gradient in 7 min; detector, UV 254 nm. The two diastereomers were obtained by separation on chiral prep-HPLC under the following conditions: column, CHIRALPAK IA-3, 0.46×5 cm, 3 um; mobile phase, hexane (with 0.1% DEA) in EtOH, 70% isocratic in 15 min; detector, UV 254 nm. Isomer 1: (25 mg, 22%, red solid) HPLC: 97.6% purity, RT=1.26 min. MS: m/z=340.3 [M+H]+. $^1$H NMR (300 MHz, Methanol-d$_4$, ppm) δ 9.18-9.08 (m, 1H), 8.92-8.83 (m, 1H), 7.82-7.61 (m, 2H), 7.04 (d, J=8.1 Hz, 1H), 4.68-4.56 (m, 1H), 3.93-3.81 (m, 1H), 3.67-3.54 (m, 2H), 3.46-3.31 (m, 2H), 2.77-2.61 (m, 4H), 1.11-1.04 (m, 4H), 0.56-0.29 (m, 4H). Isomer 2: (25 mg, 22%, red solid) HPLC: 98.1% purity, RT=1.26 min. MS: m/z=340.4 [M+H]+. $^1$H NMR (300 MHz, Methanol-d$_4$, ppm) δ 8.87-8.74 (m, 2H), 7.59-7.48 (m, 2H), 7.02 (d, J=7.9 Hz, 1H), 4.70-4.58 (m, 1H), 3.83-3.72 (m, 1H), 3.74-3.65 (m, 1H), 3.57-3.44 (m, 1H), 3.32-3.20 (m, 2H), 2.77-2.62 (m, 4H), 1.26-1.05 (m, 4H), 0.60-0.37 (m, 4H).

Example 16: Synthesis of compound 41 (2-(4-fluoropiperidin-4-yl)-N-[(3R,4R)-4-methyl-1-(8-methylquinolin-5-yl)pyrrolidin-3-yl]acetamide)

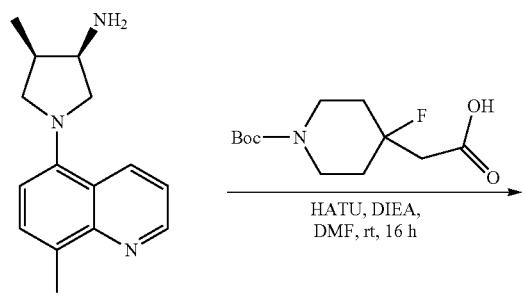

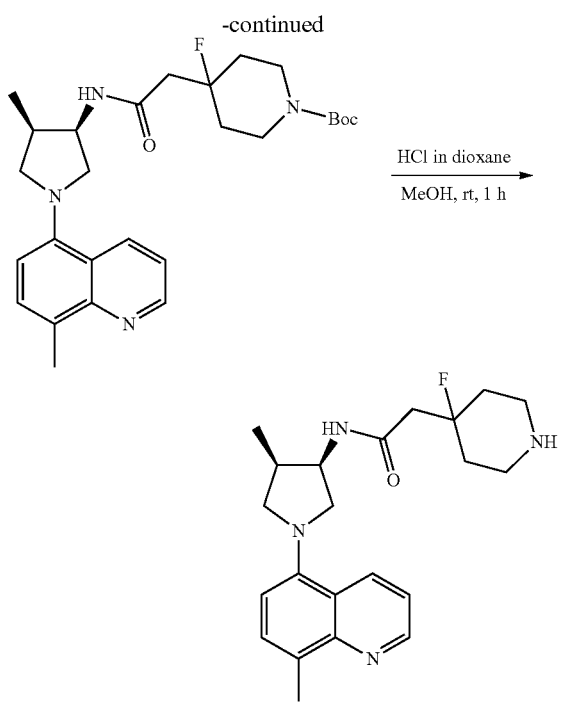

tert-butyl 4-fluoro-4-([[[(3R,4R)-4-methyl-1-(8-methylquinolin-5-yl)pyrrolidin-3-yl]carbamoyl]methyl)piperidine-1-carboxylate To a solution of (3R,4R)-4-methyl-1-(8-methylquinolin-5-yl)pyrrolidin-3-amine (59 mg, 0.24 mmol) in N,N-dimethylformamide (3 mL) was added 2-[1-[(tert-butoxy)carbonyl]-4-fluoropiperidin-4-yl]acetic acid (101 mg, 0.39 mmol), HATU (138 mg, 0.36 mmol) and DIEA (153 mg, 1.18 mmol) at room temperature. The resulting solution was stirred for 16 h at room temperature. When the reaction was done, the reaction mixture was concentrated under reduced pressure and the residue was purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 32% to 35% gradient in 7 min; detector, UV 254 nm. tert-butyl 4-fluoro-4-([[[(3R,4R)-4-methyl-1-(8-methylquinolin-5-yl)pyrrolidin-3-yl]carbamoyl]methyl)piperidine-1-carboxylate was obtained as yellow solid (19 mg, 16%). MS: m/z=485.3 [M+H]+.

2-(4-fluoropiperidin-4-yl)-N-[(3R,4R)-4-methyl-1-(8-methylquinolin-5-yl)pyrrolidin-3-yl]acetamide To a solution of tert-butyl 4-fluoro-4-([[[(3R,4R)-4-methyl-1-(8-methylquinolin-5-yl)pyrrolidin-3-yl]carbamoyl]methyl)piperidine-1-carboxylate (17 mg, 0.04 mmol) in methanol (3 mL) was added hydrogen chloride solution (4 M in dioxane, 1 mL, 4 mmol) at the room temperature. The resulting mixture was stirred for 1 h at room temperature. When the reaction was done, the reaction mixture was concentrated under reduced pressure and the residue was purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 32% to 35% gradient in 7 min; detector, UV 254 nm. 2-(4-fluoropiperidin-4-yl)-N-

[(3R,4R)-4-methyl-1-(8-methylquinolin-5-yl)pyrrolidin-3-yl]acetamide was obtained as light yellow solid (10 mg, 71%).

Compound 41

HPLC: 96.3% purity, RT=0.85 min. MS: m/z=385.2 [M+H]+. $^1$H NMR (300 MHz, Methanol-$d_4$, ppm) δ 8.84-8.76 (m, 1H), 8.74-8.63 (m, 1H), 7.53-7.40 (m, 2H), 7.01-6.92 (m, 1H), 4.69-4.57 (m, 1H), 3.82-3.70 (m, 1H), 3.52-3.39 (m, 1H), 3.36-3.00 (m, 6H), 2.82-2.56 (m, 6H), 2.23-1.85 (m, 4H), 1.08 (d, J=7.0 Hz, 3H).

Example 17: Synthesis of compound 42 (2-(4-fluoro-1-methylpiperidin-4-yl)-N-[(3R,4R)-4-methyl-1-(8-methylquinolin-5-yl)pyrrolidin-3-yl]acetamide)

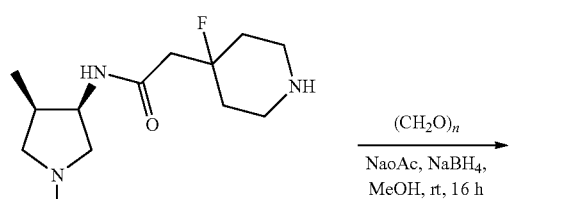

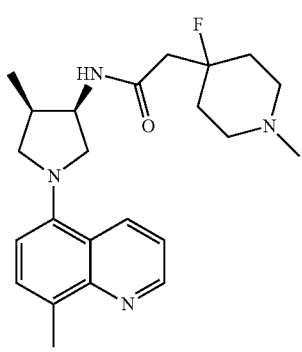

2-(4-fluoro-1-methylpiperidin-4-yl)-N-[(3R,4R)-4-methyl-1-(8-methylquinolin-5-yl)pyrrolidin-3-yl]acetamide To a solution of 2-(4-fluoropiperidin-4-yl)-N-[(3R,4R)-4-methyl-1-(8-methylquinolin-5-yl)pyrrolidin-3-yl]acetamide (176 mg, 0.46 mmol) in MeOH (30 mL) was added (CH$_2$O)$_n$ (423 mg, 4.69 mmol) and NaOAc (790 mg, 9.64 mmol) at room temperature. The resulting mixture was stirred for 2 h at room temperature, and then was added by NaBH$_4$ (275 mg, 7.27 mmol) in portions. The reaction mixture was stirred for additional 16 h at room temperature. When the reaction was done, it was quenched by the addition of water (20 mL). The resulting mixture was extracted with DCM (50 mL×3). The organic phases were combined, washed with brine and dried over Na$_2$SO$_4$. The solvent was removed under reduced pressure and the residue was purified by prep-HPLC under the following conditions: column, XBridge Shield Prep C18 OBD column, 150 mm, 5 um; mobile phase, acetonitrile in water (with 10 mmol/L NH$_4$HCO$_3$ and 0.1% NH$_3$.H$_2$O), 30% to 43% gradient in 7 min; detector, UV 254 nm. 2-(4-fluoro-1-methylpiperidin-4-yl)-N-[(3R,4R)-4-methyl-1-(8-methylquinolin-5-yl)pyrrolidin-3-yl]acetamide was obtained as yellow solid (90 mg, 49%).

Compound 42

HPLC: 96.5% purity, RT=7.86 min. MS: m/z=399.4 [M+H]+. $^1$H NMR (400 MHz, DMSO-$d_6$, ppm) δ 8.89-8.83 (m, 1H), 8.60-8.52 (m, 1H), 8.03 (d, J=8.5 Hz, 1H), 7.48-7.40 (m, 2H), 6.84 (d, J=7.8 Hz, 1H), 4.55-4.43 (m, 1H), 3.75-3.66 (m, 1H), 3.45-3.36 (m, 1H), 3.28-3.19 (m, 1H), 3.14-3.06 (m, 1H), 2.62-2.42 (m, 8H), 2.18-2.03 (m, 5H), 1.91-1.68 (m, 4H), 0.97 (d, J=6.8 Hz, 3H).

Example 18: Synthesis of compounds 43 and 44 (2-[(4S)-3,3-difluoro-1-methylpiperidin-4-yl]-N-[(3R,4R)-4-methyl-1-(8-methylquinolin-5-yl)pyrrolidin-3-yl]acetamide and 2-[(4R)-3,3-difluoro-1-methylpiperidin-4-yl]-N-[(3R,4R)-4-methyl-1-(8-methylquinolin-5-yl)pyrrolidin-3-yl]acetamide)

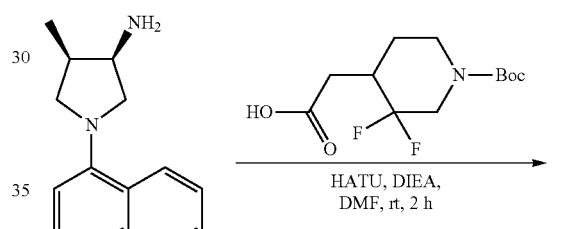

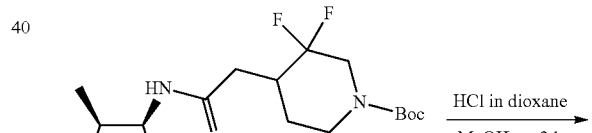

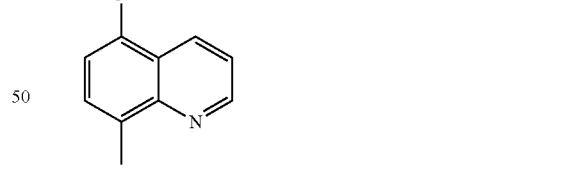

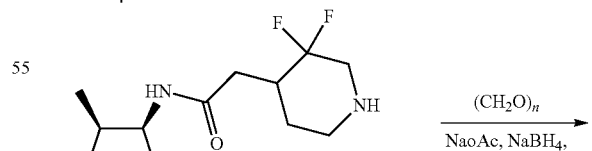

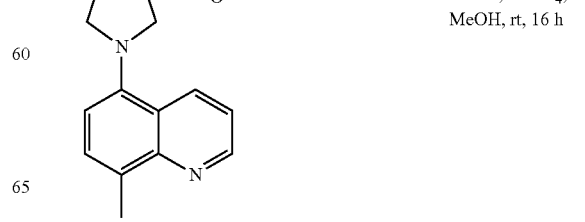

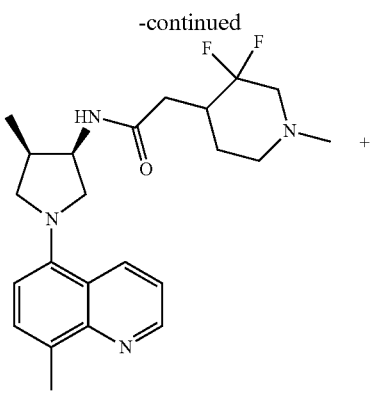

Isomer 1

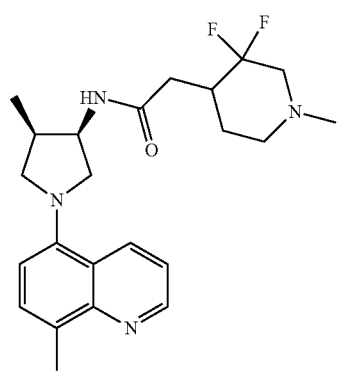

Isomer 2 tert-butyl 3,3-difluoro-4-([[[(3R,4R)-4-methyl-1-(8-methylquinolin-5-yl)pyrrolidin-3-yl]carbamoyl]methyl)piperidine-1-carboxylate To a solution of (3R,4R)-4-methyl-1-(8-methylquinolin-5-yl)pyrrolidin-3-amine (121 mg, 0.50 mmol) in N,N-dimethylformamide (3 mL) was added 2-{1-[(tert-butoxy)carbonyl]-3,3-difluoropiperidin-4-yl}acetic acid (363 mg, 1.30 mmol), HATU (342 mg, 0.90 mmol) and DIEA (380 mg, 2.94 mmol) at room temperature. The resulting solution was stirred for 2 h at room temperature. When the reaction was done, it was quenched by the addition of water (20 mL). The resulting mixture was extracted with DCM (60 mL×3). The organic phases were combined, washed with brine and dried over $Na_2SO_4$. The solvent was removed under reduced pressure to yield tert-butyl 3,3-difluoro-4-([[[(3R,4R)-4-methyl-1-(8-methylquinolin-5-yl)pyrrolidin-3-yl]carbamoyl]methyl)piperidine-1-carboxylate as yellow oil (300 mg, crude). MS: m/z=503.4 [M+H]$^+$.

2-(3,3-difluoropiperidin-4-yl)-N-[(3R,4R)-4-methyl-1-(8-methylquinolin-5-yl)pyrrolidin-3-yl]acetamide To a solution of tert-butyl 3,3-difluoro-4-([[[(3R,4R)-4-methyl-1-(8-methylquinolin-5-yl)pyrrolidin-3-yl]carbamoyl]methyl)piperidine-1-carboxylate (300 mg, crude) in methanol (4 mL), was added hydrogen chloride solution (4 M in dioxane, 4 mL, 16 mmol) at room temperature. The resulting mixture was stirred for 2 h at room temperature. When the reaction was done, the pH value of the reaction mixture was adjusted to 7-8 with sat. $NaHCO_3$ solution. The resulting mixture was extracted with ethyl acetate (50 mL×3). The organic phases were combined, washed with brine and dried over $Na_2SO_4$. The solvent was removed under reduced pressure to yield 2-(3,3-difluoropiperidin-4-yl)-N-[(3R,4R)-4-methyl-1-(8-methylquinolin-5-yl)pyrrolidin-3-yl]acetamide as yellow oil (330 mg, crude). MS: m/z=403.4 [M+H]$^+$.

2-[(4S)-3,3-difluoro-1-methylpiperidin-4-yl]-N-[(3R,4R)-4-methyl-1-(8-methylquinolin-5-yl)pyrrolidin-3-yl]acetamide and 2-[(4R)-3,3-difluoro-1-methylpiperidin-4-yl]-N-[(3R,4R)-4-methyl-1-(8-methylquinolin-5-yl)pyrrolidin-3-yl]acetamide To a solution of 2-(3,3-difluoropiperidin-4-yl)-N-[(3R,4R)-4-methyl-1-(8-methylquinolin-5-yl)pyrrolidin-3-yl]acetamide (330 mg, crude) in methanol (50 mL) was added $(CH_2O)_n$ (684 mg, 7.59 mmol), NaOAC (1.27 g, 15.52 mmol) at room temperature. The resulting mixture was stirred for 2 h at room temperature and then was added by $NaBH_4$ (444 mg, 11.73 mmol) in portions. The reaction mixture was stirred for additional 16 h at room temperature. When the reaction was done, it was quenched by the addition of water (20 mL). The resulting mixture was extracted with DCM (50 mL×3). The organic phases were combined, washed with brine and dried over $Na_2SO_4$. The solvent was removed under reduced pressure and the residue was first purified by prep-HPLC under the following conditions: column, XBridge Prep C18 OBD Column, 150 mm, 5 um; mobile phase, acetonitrile in water (with 10 mmol/L $NH_4HCO_3$ and 0.1% $NH_3.H_2O$), 27% to 46% gradient in 7 min; detector, UV 254 nm. Then the two diastereomers were obtained by separation on chiral prep-HPLC under the following conditions: column, Repaired ADH, 0.46×10 cm, 3 um; mobile phase, hexane (with 0.1% DEA) in EtOH, 70% isocratic in 30 min; detector, UV 254 nm.

Isomer 1:

(15 mg, 7% for 3 steps, off-white solid) HPLC: 97.9% purity, RT=2.77 min. MS: m/z=209.1 [M+H]$^+$. $^1$H NMR (300 MHz, Methanol-d$_4$, ppm) δ 8.83-8.75 (m, 1H), 8.73-8.59 (m, 1H), 7.50-7.39 (m, 2H), 6.96 (d, J=7.8 Hz, 1H), 4.68-4.56 (m, 1H), 3.80-3.68 (m, 1H), 3.56-3.39 (m, 1H), 3.29-2.97 (m, 3H), 2.87-2.54 (m, 6H), 2.40-2.18 (m, 6H), 2.16-2.01 (m, 1H), 1.81-1.69 (m, 1H), 1.61-1.42 (m, 1H), 1.06 (d, J=6.9 Hz, 3H).

Isomer 2:

(15 mg, 7% for 3 steps, off-white solid) HPLC: 98.6% purity, RT=2.70 min. MS: m/z=209.0 [M+H]$^+$. $^1$H NMR (300 MHz, Methanol-d$_4$, ppm) δ 8.84-8.75 (m, 1H), 8.74-8.64 (m, 1H), 7.51-7.40 (m, 2H), 6.97 (d, J=7.8 Hz, 1H), 4.70-4.54 (m, 1H), 3.79-3.67 (m, 1H), 3.52-3.33 (m, 1H), 3.31-2.98 (m, 3H), 2.91-2.81 (m, 1H), 2.77-2.55 (m, 5H), 2.41-2.20 (m, 6H), 2.20-2.06 (m, 1H), 1.91-1.80 (m, 1H), 1.66-1.52 (m, 1H), 1.06 (d, J=6.9 Hz, 3H).

Example 19: Synthesis of compounds 49 and 50 ((3S,4R)-4-fluoro-1-(8-trifluoromethyl-quinolin-5-yl)-pyrrolidin-3-ylamine and (3R,4S)-4-fluoro-1-(8-trifluoromethyl-quinolin-5-yl)-pyrrolidin-3-ylamine)

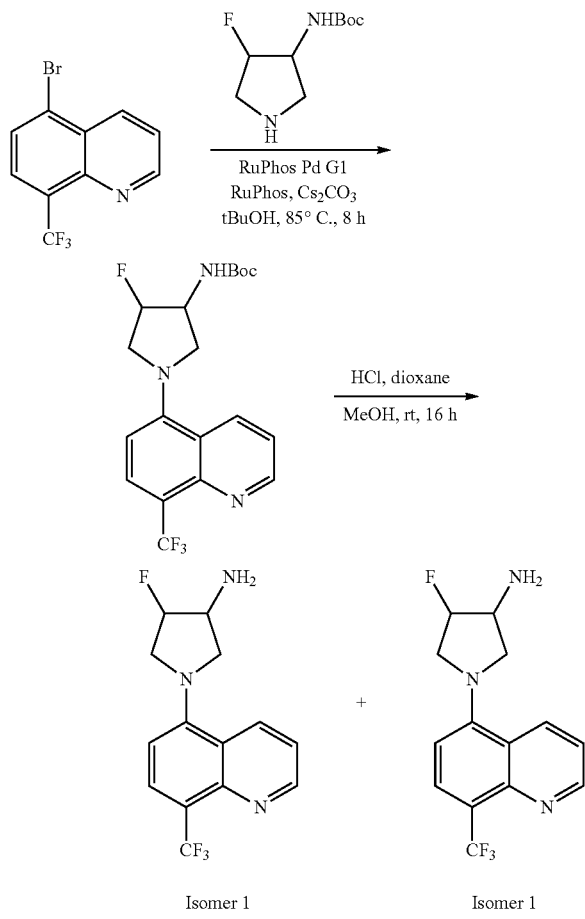

[cis-4-fluoro-1-(8-trifluoromethyl-quinolin-5-yl)-pyrrolidin-3-yl]-carbamic acid tert-butyl ester To a solution of 5-bromo-8-(trifluoromethyl)quinoline (400 mg; 1.45 mmol) in tBuOH (9.0 mL) was added cis-(3-boc-amino)-4-fluoropyrrolidine (355 mg; 1.74 mmol), chloro(2-dicyclohexylphosphino-2',6'-di-i-propoxy-1,1'-biphenyl) [2-(2-aminoethylphenyl)]palladium(ii), methyl-t-butylether adduct (59.2 mg; 0.072 mmol), 2-dicyclohexylphosphino-2',6'-di-i-propoxy-1,1'-biphenyl (33.8 mg; 0.072 mmol) and cesium carbonate (944 mg; 2.90 mmol). The resulting mixture was flushed with nitrogen for 10 min and microwaved at 85° C. for 8 h. The reaction mixture was concentrated under reduced pressure, suspended in DCM (20 mL), sonicated for 30 sec and filtered on celite. The solvent was removed under reduced pressure and the residue was purified by flash chromatography eluting with EtOAc in hexane (10% to 80% gradient) to yield [cis-4-fluoro-1-(8-trifluoromethyl-quinolin-5-yl)-pyrrolidin-3-yl]-carbamic acid tert-butyl ester as a tan glassy solid (507 mg; 88%). MS: m/z=400 [M+H]$^+$.

(3S,4R)-4-fluoro-1-(8-trifluoromethyl-quinolin-5-yl)-pyrrolidin-3-ylamine and (3R,4S)-4-fluoro-1-(8-trifluoromethyl-quinolin-5-yl)-pyrrolidin-3-ylamine To a solution of [cis-4-fluoro-1-(8-trifluoromethyl-quinolin-5-yl)-pyrrolidin-3-yl]-carbamic acid tert-butyl ester (485 mg; 1.21 mmol) in methanol (12 mL) was added hydrogen chloride solution (4 M in dioxane, 9 mL, 36 mmol) at room temperature. The resulting mixture was stirred overnight at room temperature. When the reaction was done, ether (40 mL) was added to the orange solution and the yellow suspension was stirred at room temperature for 1 h. The solids were filtered and dissolved in a 5N solution of sodium hydroxide. The mixture was extracted with ethyl acetate, the combined organic phase was washed with brine (30 mL), dried over anhydrous sodium sulfate, filtered and concentrated under reduced pressure. The two enantiomers were obtained by separation on chiral prep-HPLC under the following conditions: column, Lux Cellulose-2, 250×21.20 mm, 5 um; mobile phase, EtOH with 0.5% DMEA, 30% isocratic in 11 min; detector, UV 254 nm.

Isomer 1:

(86 mg, 23%, tan solid) HPLC: 98.9% purity, RT=1.78 min. MS: m/z=300 [M+H]$^+$. $^1$H NMR (400 MHz, Chloroform-d, ppm) δ 8.86 (d, J=1.7 Hz, 1H), 8.64 (d, J=5.6 Hz, 1H), 8.60 (d, J=1.7 Hz, 1H), 6.49 (d, J=5.7 Hz, 1H), 6.41 (s, 1H), 4.29-4.14 (m, 2H), 4.08 (dt, J=12.2, 7.3 Hz, 1H), 3.91 (q, J=9.2, 8.7 Hz, 1H), 3.40-3.26 (m, 2H), 3.06 (p, J=7.6 Hz, 1H), 2.56 (t, J=6.0 Hz, 2H), 2.52 (q, J=7.1 Hz, 4H), 2.41-2.24 (m, 2H), 0.99 (t, J=7.1 Hz, 6H).

Isomer 2:

(104 mg, 29%, cream solid) HPLC: >99.9% purity, RT=1.75 min. MS: m/z=300 [M+H]$^+$. $^1$H NMR (400 MHz, Chloroform-d, ppm) δ 8.99 (dd, J=4.1, 1.7 Hz, 1H), 8.47 (dd, J=8.7, 1.7 Hz, 1H), 7.90 (dd, J=8.4, 0.8 Hz, 1H), 7.37 (dd, J=8.7, 4.1 Hz, 1H), 6.75 (d, J=8.3 Hz, 1H), 5.05 (dt, J=54.5, 3.4 Hz, 1H), 4.05 (ddd, J=37.9, 12.3, 3.6 Hz, 1H), 3.79-3.54 (m, 4H), 1.52 (s, 2H).

Example 20: Synthesis of compound 51 ((3R,4R)-4-methyl-1-(8-methyl-[1,7]naphthyridin-5-yl)-pyrrolidin-3-ylamine hydrochloride)

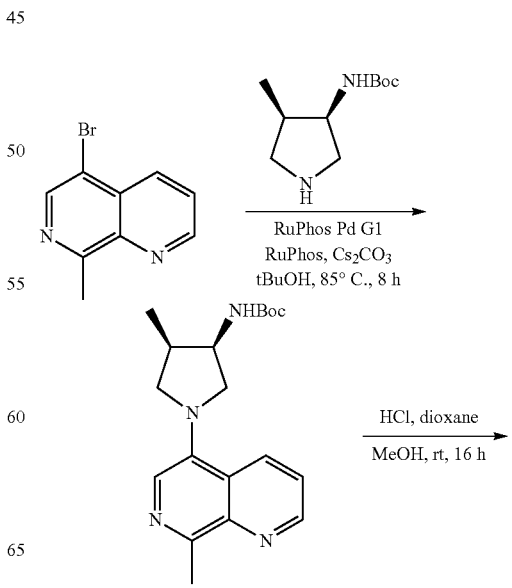

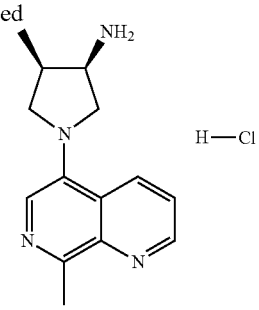

[(3R,4R)-4-methyl-1-(8-methyl-[1,7]naphthyridin-5-yl)-pyrrolidin-3-yl]-carbamic acid tert-butyl ester To a solution of 5-bromo-8-methyl-[1,7]naphthyridine (100 mg; 0.45 mmol)) in tBuOH (1.5 mL) was added (3R,4R)-3-(boc-amino)-4-methylpyrrolidine (104 mg; 0.49 mmol), chloro(2-dicyclohexylphosphino-2',6'-di-i-propoxy-1,1'-biphenyl)[2-(2-aminoethylphenyl)]palladium(ii), methyl-t-butylether adduct (18.3 mg; 0.02 mmol), 2-dicyclohexylphosphino-2',6'-di-i-propoxy-1,1'-biphenyl (10.5 mg; 0.02 mmol), cesium carbonate (292 mg; 0.90 mmol). The resulting mixture was flushed with nitrogen for 10 min and microwaved at 100° C. for 8 h. The reaction mixture was concentrated under reduced pressure, and the residue was purified by flash chromatography eluting with EtOAc in hexane (20% to 80% gradient) to yield [(3R,4R)-4-methyl-1-(8-methyl-[1,7]naphthyridin-5-yl)-pyrrolidin-3-yl]-carbamic acid tert-butyl ester as a light yellow solid (70 mg; 46%). MS: m/z=343 [M+H]+.

(3R,4R)-4-methyl-1-(8-methyl-[1,7]naphthyridin-5-yl)-pyrrolidin-3-ylamine hydrochloride To a solution of [(3R,4R)-4-methyl-1-(8-methyl-[1,7]naphthyridin-5-yl)-pyrrolidin-3-yl]-carbamic acid tert-butyl ester (120 mg, 0.35 mmol) in methanol (3 mL) was added hydrogen chloride solution (4 M in dioxane, 1.3 mL, 5.3 mmol) at room temperature. The resulting mixture was stirred overnight at room temperature. When the reaction was done, the mixture was concentrated to dryness to yield (3R,4R)-4-methyl-1-(8-methyl-[1,7]naphthyridin-5-yl)-pyrrolidin-3-ylamine hydrochloride as a yellow amorphous solid (110 mg; 97%).

Compound 51

HPLC: 98.9% purity, RT=0.93 min. MS: m/z=243 [M+H]+.

Example 21: Synthesis of compound 52 (N-[(3R,4R)-4-methyl-1-(8-methyl-[1,7]naphthyridin-5-yl)-pyrrolidin-3-yl]-2-(1-methyl-piperidin-4-yl)-acetamide)

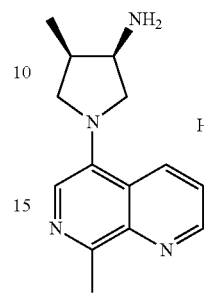 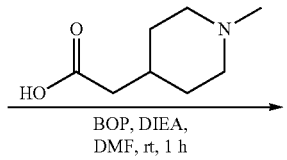

N-[(3R,4R)-4-methyl-1-(8-methyl-[1,7]naphthyridin-5-yl)-pyrrolidin-3-yl]-2-(1-methyl-piperidin-4-yl)-acetamide To a solution of (3R,4R)-4-methyl-1-(8-methyl-[1,7]naphthyridin-5-yl)-pyrrolidin-3-ylamine hydrochloride 30 mg, 0.1 mmol) in N,N-dimethylformamide (1 mL), were added 2-(1-methylpiperidin-4-yl)acetic acid (16.5 mg, 0.105 mmol), DIEA (63 µL, 0.948 mmol) and (benzotriazol-1-yloxy)tris(dimethylamino)phosphonium hexafluorophosphate (51 mg, 0.114 mmol). The resulting solution was stirred for 1 hour at room temperature. When the reaction was done, the solvent was removed under reduced pressure and the residue was purified by prep-HPLC under the following conditions: column, XBridge Prep C18 OBD 10 µm, column, 30×250 mm; mobile phase, acetonitrile in water (with 0.1% NH$_4$OH), 10% to 60% gradient in 15 min; detector, UV 254 nm. N-[(3R,4R)-4-methyl-1-(8-methyl-[1,7]naphthyridin-5-yl)-pyrrolidin-3-yl]-2-(1-methyl-piperidin-4-yl)-acetamide was obtained as white amorphous solid (32 mg, 88%).

Compound 52

HPLC: >99% purity, RT=1.30 min. MS: m/z=382 [M+H]+. $^1$H NMR (400 MHz, DMSO-d6, ppm) δ 8.96 (dd, J=4.1, 1.6 Hz, 1H), 8.60 (dd, J=8.7, 1.6 Hz, 1H), 7.91 (d, J=8.4 Hz, 1H), 7.86 (s, 1H), 7.66 (dd, J=8.7, 4.1 Hz, 1H), 4.48 (dtd, J=9.2, 6.0, 3.4 Hz, 1H), 3.85 (dd, J=9.9, 6.0 Hz, 1H), 3.51 (dd, J=9.1, 7.3 Hz, 1H), 3.36 (d, J=8.9 Hz, 1H), 3.20 (dd, J=9.9, 3.4 Hz, 1H), 2.81 (s, 3H), 2.73-2.61 (m, 2H), 2.49-2.43 (m, 1H), 2.10 (s, 3H), 2.08-1.99 (m, 2H), 1.77 (tdd, J=11.3, 5.8, 2.4 Hz, 2H), 1.65-1.45 (m, 3H), 1.20-1.05 (m, 2H), 0.97 (d, J=6.8 Hz, 3H).

The following compounds were synthesized in an analogous manner:

Compound 53 (2-(1-methyl-azetidin-3-yl)-N-[(3R, 4R)-4-methyl-1-(8-methyl-[1,7]naphthyridin-5-yl)-pyrrolidin-3-yl]-acetamide)

From 8-[(3R,4R)-3-amino-4-methylpyrrolidin-1-yl]quinoxaline-5-carbonitrile and (1-Methyl-azetidin-3-yl)-acetic acid hydrochloride, purified by prep-HPLC under the following conditions: prep-HPLC under the following conditions: column, XBridge Prep C18 OBD 10 μm, column, 30×250 mm; mobile phase, acetonitrile in water (with 0.1% NH$_4$OH), 10% to 60% gradient in 15 min; detector, UV 254 nm (29 mg, 86%, white amorphous solid). HPLC: >99% purity, RT=1.24 min. MS: m/z=354 [M+H]$^+$. $^1$H NMR (400 MHz, DMSO-d6, ppm) δ 8.97 (dd, J=4.1, 1.5 Hz, 1H), 8.61 (dd, J=8.7, 1.7 Hz, 1H), 7.97 (d, J=8.5 Hz, 1H), 7.87 (s, 1H), 7.67 (dd, J=8.7, 4.1 Hz, 1H), 4.46 (dtd, J=9.3, 6.0, 3.4 Hz, 1H), 3.85 (dd, J=9.9, 6.0 Hz, 1H), 3.51 (dd, J=9.1, 7.3 Hz, 1H), 3.38-3.32 (m, 1H), 3.28-3.15 (m, 3H), 2.82 (s, 3H), 2.78-2.68 (m, 2H), 2.61-2.55 (m, 1H), 2.48-2.31 (m, 3H), 2.14 (s, 3H), 0.95 (d, J=6.9 Hz, 3H).

Example 22: Synthesis of Compound 54 (1-pyrido[2,3-b]pyrazin-8-yl-pyrrolidine-3-carboxylic acid (2-diethylamino-ethyl)-amide)

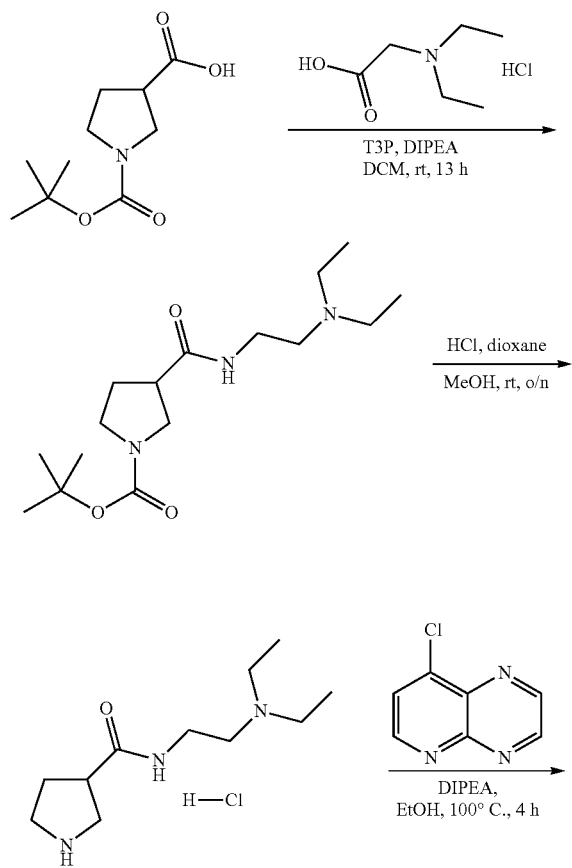

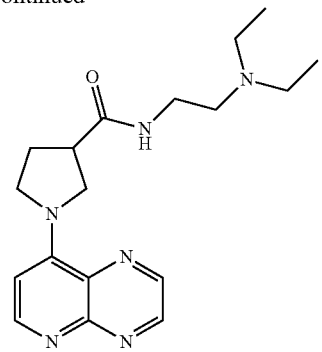

3-(2-diethylamino-ethylcarbamoyl)-pyrrolidine-1-carboxylic acid tert-butyl ester To a solution of 1-boc-pyrrolidine-3-carboxylic acid (1.0 g, 4.65 mmol), in anhydrous dichloromethane (25.0 mL) were added N,N-diethylethylenediamine (653 al, 4.65 mmol), DIEA (4.0 ml, 23.2 mmol) and a 50% solution of propylphosphonic anhydride (8.2 mL, 13.9 mmol) in ethyl acetate. The resulting solution was stirred for 1 h30 hour at room temperature. When the reaction was done, the was diluted with dichloromethane (70 mL), extracted with a saturated solution of sodium bicarbonate (3×50 mL) and washed with brine (50 mL). The organic phase was dried over anhydrous sodium sulfate, filtered, concentrated under reduced pressure and the residue was purified by flash chromatography using a NH2-bonded silica column and eluting with EtOAc in hexane (10% to 60% gradient) to yield 3-(2-diethylamino-ethylcarbamoyl)-pyrrolidine-1-carboxylic acid tert-butyl ester as a colorless oil (1.21 g, 83%). MS: m/z=314 [M+H]$^+$.

pyrrolidine-3-carboxylic acid (2-diethylamino-ethyl)-amide hydrochloride

To a solution of 3-(2-diethylamino-ethylcarbamoyl)-pyrrolidine-1-carboxylic acid tert-butyl ester (1.2 g; 3.73 mmol) in methanol (30 mL), was added hydrogen chloride solution (4 M in dioxane, 28 mL, 112 mmol) at room temperature. The resulting mixture was stirred overnight at room temperature. When the reaction was done, the mixture was concentrated under reduced pressure, the residue was dissolved in isopropanol (20 mL), added acetonitrile (50 mL) and ether (10 mL) and the colorless solution was stirred at room temperature overnight. The white suspension was filtered and the white solid dried under vacuo to yield pyrrolidine-3-carboxylic acid (2-diethylamino-ethyl)-amide hydrochloride as a white solid (581 mg, 62%). MS: m/z=214 [M+H]$^+$.

1-pyrido[2,3-b]pyrazin-8-yl-pyrrolidine-3-carboxylic acid (2-diethylamino-ethyl)-amide A solution of 8-chloro-pyrido[2,3-b]pyrazine (60 mg, 0.362 mmol), pyrrolidine-3-carboxylic acid (2-diethylamino-ethyl)-amide hydrochloride (136 mg, 0.544 mmol) and DIEA (316 al, 1.81 mmol) in anhydrous ethanol (3 mL) was microwaved at 100° C. for 3 h. When the reaction was done, the solvent was removed under reduced pressure and the residue was purified by flash chromatography using a NH2-bonded silica column and eluting with methanol in dichloromethane (0% to 7% gradient) to yield 1-pyrido[2,3-b]pyrazin-8-yl-pyrrolidine-3-carboxylic acid (2-diethyl-amino-ethyl)-amide as yellow solid (108 mg, 85%).

Compound 54

HPLC: 97.3% purity, RT=1.00 min. MS: m/z=343 [M+H]+. 1H NMR (400 MHz, Chloroform-d, ppm) δ 8.86 (d, J=1.7 Hz, 1H), 8.64 (d, J=5.6 Hz, 1H), 8.60 (d, J=1.7 Hz, 1H), 6.49 (d, J=5.7 Hz, 1H), 6.41 (s, 1H), 4.29-4.14 (m, 2H), 4.08 (dt, J=12.2, 7.3 Hz, 1H), 3.91 (q, J=9.2, 8.7 Hz, 1H), 3.40-3.26 (m, 2H), 3.06 (p, J=7.6 Hz, 1H), 2.56 (t, J=6.0 Hz, 2H), 2.52 (q, J=7.1 Hz, 4H), 2.41-2.24 (m, 2H), 0.99 (t, J=7.1 Hz, 6H).

Example 23: Synthesis of compound 55 ([1-(1,2-Dimethyl-1H-pyrrolo[2,3-b]pyridin-4-yl)-pyrrolidin-3-ylmethyl]-(2-piperidin-1-yl-ethyl)-amine)

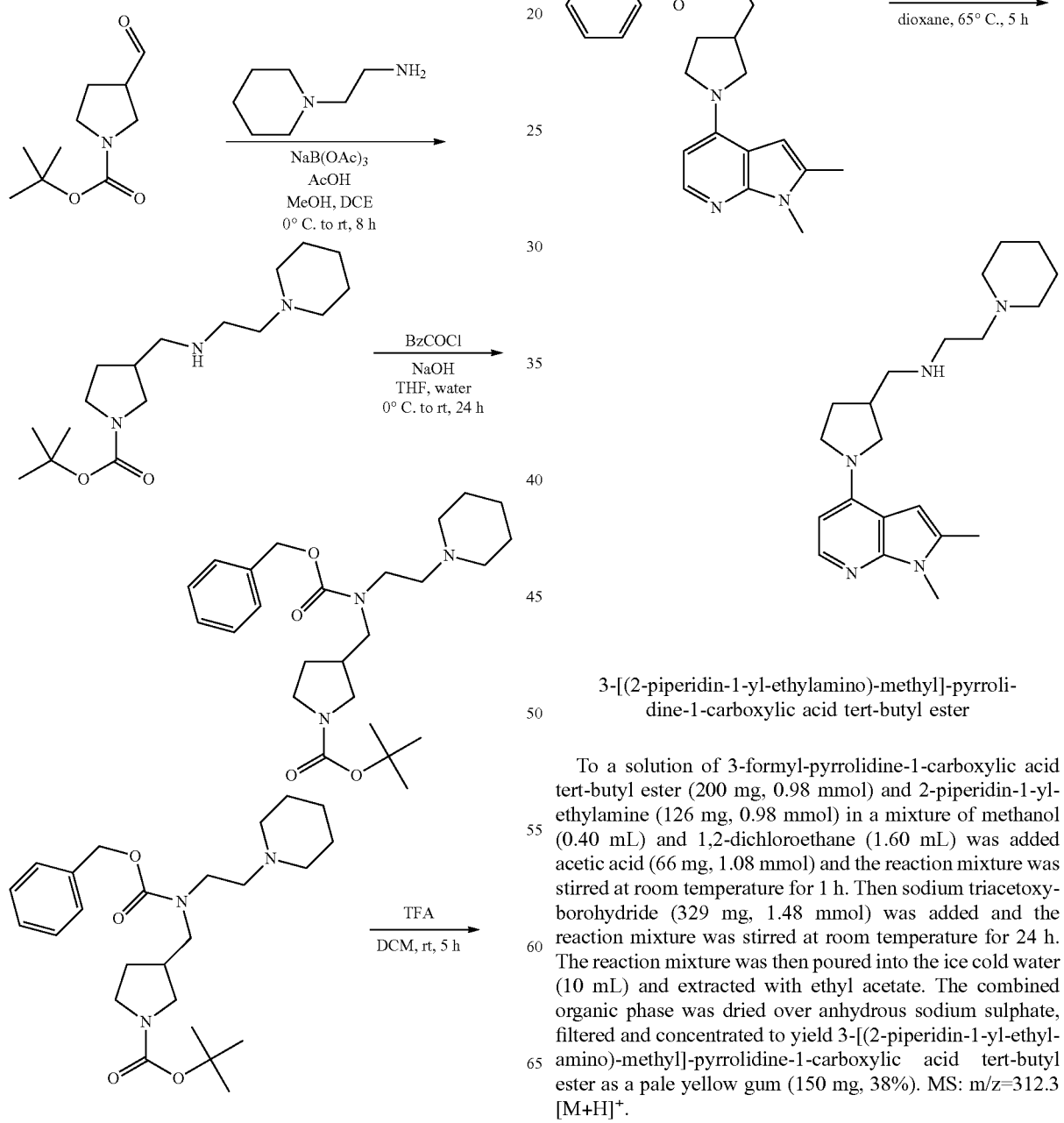

3-[(2-piperidin-1-yl-ethylamino)-methyl]-pyrrolidine-1-carboxylic acid tert-butyl ester To a solution of 3-formyl-pyrrolidine-1-carboxylic acid tert-butyl ester (200 mg, 0.98 mmol) and 2-piperidin-1-yl-ethylamine (126 mg, 0.98 mmol) in a mixture of methanol (0.40 mL) and 1,2-dichloroethane (1.60 mL) was added acetic acid (66 mg, 1.08 mmol) and the reaction mixture was stirred at room temperature for 1 h. Then sodium triacetoxyborohydride (329 mg, 1.48 mmol) was added and the reaction mixture was stirred at room temperature for 24 h. The reaction mixture was then poured into the ice cold water (10 mL) and extracted with ethyl acetate. The combined organic phase was dried over anhydrous sodium sulphate, filtered and concentrated to yield 3-[(2-piperidin-1-yl-ethylamino)-methyl]-pyrrolidine-1-carboxylic acid tert-butyl ester as a pale yellow gum (150 mg, 38%). MS: m/z=312.3 [M+H]+.

3-{[benzyloxycarbonyl-(2-piperidin-1-yl-ethyl)-amino]-methyl}-pyrrolidine-1-carboxylic acid tert-butyl ester To a solution of 3-[(2-piperidin-1-yl-ethylamino)-methyl]-pyrrolidine-1-carboxylic acid tert-butyl ester (150 mg, 0.38 mmol) in THF (1.2 mL) and water (0.3 mL) was added sodium hydroxide (45 mg, 1.13 mmol) and a solution of benzyl chloroformate 50% in toluene (0.12 mL, 0.41 mmol). The reaction mixture was stirred at room temperature for 24 h, poured onto ice cold water (10 mL) and extracted with ethyl acetate. The combined organic phase was dried over anhydrous sodium sulphate, filtered and concentrated to yield 3-{[benzyloxycarbonyl-(2-piperidin-1-yl-ethyl)-amino]-methyl}-pyrrolidine-1-carboxylic acid tert-butyl ester as a pale yellow gum (150 mg, 47%). MS: m/z=446.3 [M+H]$^+$.

(2-piperidin-1-yl-ethyl)-pyrrolidin-3-ylmethyl-carbamic acid benzyl ester trifluoroacetate To a solution of 3-{[benzyloxycarbonyl-(2-piperidin-1-yl-ethyl)-amino]-methyl}-pyrrolidine-1-carboxylic acid tert-butyl ester (150 mg, 0.18 mmol) in dichloromethane (0.75 mL) at 0° C. was added trifluoroacetic acid (0.75 mL) dropwise over a period of 30 min. The reaction mixture was stirred at room temperature for 5 h. The reaction mixture was then concentrated under reduced pressure and azeotroped with toluene to yield (2-piperidin-1-yl-ethyl)-pyrrolidin-3-ylmethyl-carbamic acid benzyl ester trifluoroacetate as a brown gum (80 mg, 57%). MS: m/z=346.3 [M+H]$^+$.

[1-(1,2-dimethyl-1H-pyrrolo[2,3-b]pyridin-4-yl)-pyrrolidin-3-ylmethyl]-(2-piperidin-1-yl-ethyl)-carbamic acid benzyl ester To a solution of 4-bromo-1,2-dimethyl-1H-pyrrolo[2,3-b]pyridine (200 mg, 0.88 mmol) and (2-piperidin-1-yl-ethyl)-pyrrolidin-3-ylmethyl-carbamic acid benzyl ester trifluoroacetate 847 mg, 1.06 mmol) in toluene (2 mL), was added potassium tert-butoxide (307 mg, 2.65 mmol), 2,2'-bis-diphenylphosphanyl-[1,1']binaphthalenyl (56 mg, 0.09 mmol). The reaction mixture was degassed for 30 min before tris(dibenzylideneacetone)dipalladium(0) (42 mg, 0.04 mmol) was added. The reaction mixture was heated at 100° C. in a sealed tube for 24 h, poured over ice cold water (30 mL) and extracted with ethyl acetate. The combined organic phase was dried over anhydrous sodium sulphate, filtered and concentrated to yield [1-(1,2-dimethyl-1H-pyrrolo[2,3-b]pyridin-4-yl)-pyrrolidin-3-ylmethyl]-(2-piperidin-1-yl-ethyl)-carbamic acid benzyl ester as a black gum (220 mg, 15%). MS: m/z=490.2 [M+H]$^+$.

[1-(1,2-dimethyl-1H-pyrrolo[2,3-b]pyridin-4-yl)-pyrrolidin-3-ylmethyl]-(2-piperidin-1-yl-ethyl)-amine To a solution of [1-(1,2-dimethyl-1H-pyrrolo[2,3-b]pyridin-4-yl)-pyrrolidin-3-ylmethyl]-(2-piperidin-1-yl-ethyl)-carbamic acid benzyl ester (200 mg, 0.12 mmol) in dioxane (1 mL) was added a 4M solution of hydrogen chloride in dioxane (0.15 mL, 0.60 mmol). The resulting pink reaction mixture was heated at 65° C. for 5 h and concentrated under reduced pressure. The resulting mixture was dissolved in water, basified with an aqueous solution of sodium bicarbonate and extracted with ethyl acetate. The combined organic phase was dried over anhydrous sodium sulphate, filtered and concentrated to afford the crude product, which was purified by by flash chromatography to yield [1-(1,2-dimethyl-1H-pyrrolo[2,3-b]pyridin-4-yl)-pyrrolidin-3-ylmethyl]-(2-piperidin-1-yl-ethyl)-amine as a brown gum (10 mg, 23%).

Compound 55

HPLC: 97.3% purity, RT=1.00 min. MS: m/z=343 [M+H]$^+$. $^1$H NMR (400 MHz, Chloroform-d, ppm) δ 8.86 (d, J=1.7 Hz, 1H), 8.64 (d, J=5.6 Hz, 1H), 8.60 (d, J=1.7 Hz, 1H), 6.49 (d, J=5.7 Hz, 1H), 6.41 (s, 1H), 4.29-4.14 (m, 2H), 4.08 (dt, J=12.2, 7.3 Hz, 1H), 3.91 (q, J=9.2, 8.7 Hz, 1H), 3.40-3.26 (m, 2H), 3.06 (p, J=7.6 Hz, 1H), 2.56 (t, J=6.0 Hz, 2H), 2.52 (q, J=7.1 Hz, 4H), 2.41-2.24 (m, 2H), 0.99 (t, J=7.1 Hz, 6H).

Example 24: HEK TLR7 Cell Assay

Into 384 CulturePlates (Corning 3707) was placed 5000 c/w of TLR7/NFKb HEK cells in 30 uL DMEM without Phenol red (gibco #31053) and 10% FCS-HI, 2 mM L-Glutamine, 1% Pen/Strept. The cells are incubated for 24 h at 37 degrees Celsius, and 10% carbon dioxide. Dispense 3 uL of controls, standards, and compounds to wells, incubate for 30 min then add 3 uL of R848 (10 uM final concentration) agonist in 20 mM Hepes. Incubate for 5 hours and then allow to stand at room temperature for 15 min. Add 10 uL of Steady-Glo substrate reagent and shake assay plate for 5 min at 1500 rpm. Let the assay plate sit for 30 min at room temperature and then read plate on EnVision.

Example 25: HEK TLR8 Cell Assay

Into 384 CulturePlates (Corning 3707) was placed 5000 c/w of TLR8/NFKb HEK cells in 30 uL DMEM without Phenol red (gibco #31053) and 10% FCS-HI, 2 mM L-Glutamine, 1% Pen/Strept. The cells are incubated for 24 h at 37 degrees Celsius, and 10% carbon dioxide. Dispense 3 uL of controls, standards, and compounds to wells, incubate for 30 min then add 3 uL of R848 (30 uM final concentration) agonist in 20 mM Hepes. Incubate for 5 hours and then allow to stand at room temperature for 15 min. Add 10 uL of Steady-Glo substrate reagent and shake assay plate for 5 min at 1500 rpm. Let the assay plate sit for 30 min at room temperature and then read plate on EnVision.

Results are given in the following table.
A: IC$_{50}$<1 uM
B: IC$_{50}$: 1 uM-10 uM
C: IC$_{50}$>10 uM

TABLE 2

| Example | Compound | TLR7 | TLR8 |
|---|---|---|---|
| 1 | 1 | A | B |
| 2 | 2 | A | A |
| 3 | 3 | A | A |
| 3 | 4 | A | A |
| 3 | 5 | A | A |
| 3 | 6 | A | A |
| 2 | 7 | B | B |
| 2 | 8 | A | A |
| 4 | 9 | A | A |
| 5 | 10 | A | A |
| 6 | 11 | A | A |
| 6 | 12 | A | A |
| 3 | 13 | B | C |
| 3 | 14 | A | B |

TABLE 2-continued

| Example | Compound | TLR7 | TLR8 |
|---|---|---|---|
| 2 | 15 | B | B |
| 2 | 16 | B | B |
| 7 | 17 | B | C |
| 8 | 18 | A | A |
| 9 | 19 | A | A |
| 9 | 20 | A | B |
| 9 | 21 | A | A |
| 9 | 22 | A | A |
| 8 | 23 | B | C |
| 8 | 24 | A | A |
| 10 | 25 | A | A |
| 11 | 26 | A | A |
| 12 | 27 | B | B |
| 12 | 28 | B | B |
| 9 | 29 | B | C |
| 9 | 30 | B | B |
| 8 | 31 | B | C |
| 8 | 32 | C | C |
| 13 | 33 | C | C |
| 14 | 34 | A | A |
| 15 | 35 | B | B |
| 15 | 36 | A | B |
| 15 | 37 | A | B |
| 15 | 38 | A | B |
| 14 | 39 | B | C |
| 14 | 40 | A | B |
| 16 | 41 | A | B |
| 17 | 42 | A | A |
| 18 | 43 | B | C |
| 18 | 44 | B | B |
| 15 | 45 | C | C |
| 15 | 46 | B | C |
| 14 | 47 | B | C |
| 14 | 48 | C | C |
| 19 | 49 | C | C |
| 19 | 50 | C | C |
| 20 | 51 | B | C |
| 21 | 52 | A | C |
| 21 | 53 | B | C |
| 22 | 54 | C | C |
| 23 | 55 | B | C |
| 1 | 56 | A | A |

Example 26. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I,

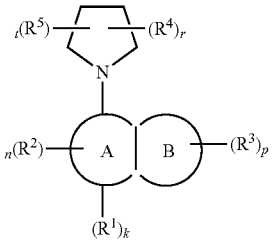

I or a pharmaceutically acceptable salt thereof, wherein,
Ring A is

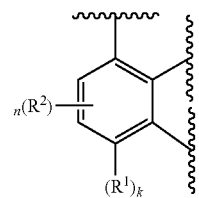

Ring B is heteroaryl having 1-4 heteroatoms independently selected from nitrogen, oxygen, and sulfur; each of which is optionally substituted;
$R^1$ is —$CH_3$, or —$CF_3$;
each $R^2$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;

each R³ is independently —H, —R, halogen, -haloalkyl, —OR, —SR, —CN, —NO₂, —SO₂R, —SOR, —C(O)R, —CO₂R, —C(O)N(R)₂, —NRC(O)R, —NRC(O)N(R)₂, —NRSO₂R, or —N(R)₂;

each R⁴ is independently —R, halogen, -haloalkyl, —OR, —SR, —CN, —NO₂, —SO₂R, —SOR, —C(O)R, —CO₂R, —C(O)N(R)₂, —NRC(O)R, —NRC(O)N(R)₂, —NRC(O)OR, —NRSO₂R, or —N(R)₂;

each R⁵ is independently —R, halogen, -haloalkyl, —OR, —SR, —CN, —NO₂, —SO₂R, —SOR, —C(O)R, —CO₂R, —C(O)N(R)₂, —NRC(O)R, —NRC(O)N(R)₂, —NRSO₂R, or —N(R)₂; . . . "

each R is independently $C_{1-6}$ aliphatic, $C_{3-10}$aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

k is 1 or 2;

n is 0, 1, or 2;

p is 0, 1, or 2;

r is 1, 2, or 3; and t is 1, 2, or 3.

2. The compound of claim 1 or a pharmaceutically acceptable salt thereof, wherein Ring B is pyridyl, pyrimidinyl, pyrazinyl, pyridazinyl, triazinyl, pyrrole, imidazole, isoxazole, oxazole, or thiazole; each of which is optionally substituted.

3. The compound of claim 2 or a pharmaceutically acceptable salt thereof, wherein Ring B is

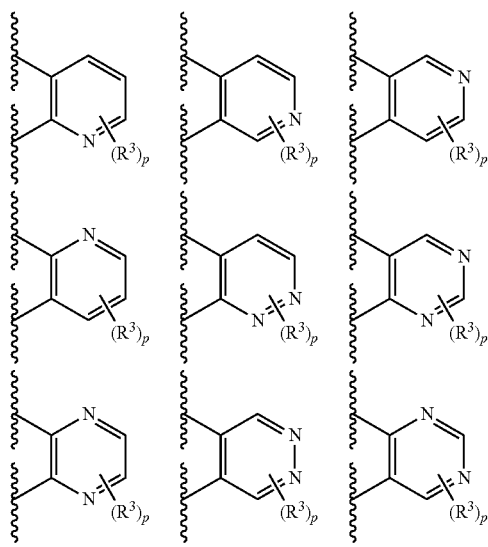

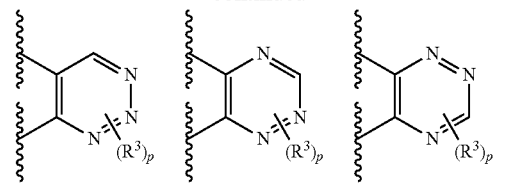

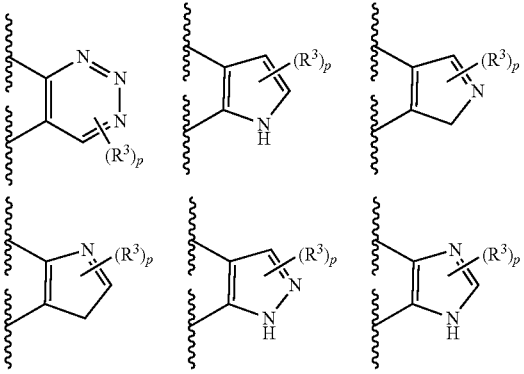

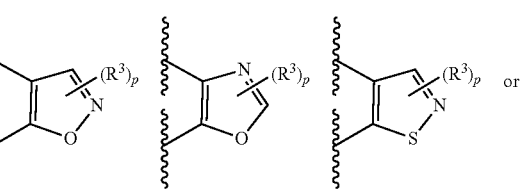

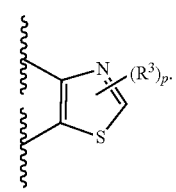

4. The compound of claim 3 or a pharmaceutically acceptable salt thereof, wherein Ring B is

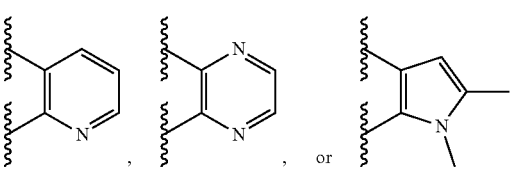

5. The compound of claim 1 or a pharmaceutically acceptable salt thereof, wherein each R⁴ is independently $C_{1-6}$ aliphatic, —OR, —C(O)R, —CO₂R, —C(O)N(R)₂, —NRC(O)R, —NRC(O)OR, —NRC(O)N(R)₂, —NRSO₂R, or —N(R)₂; each of which is optionally substituted.

6. The compound of claim 5 or a pharmaceutically acceptable salt thereof, wherein each R⁴ is independently $C_{1-6}$ aliphatic, —C(O)N(R)₂, —NRC(O)R, or —N(R)₂; each of which is optionally substituted.

7. The compound of claim 1 or a pharmaceutically acceptable salt thereof, wherein each $R^4$ is independently

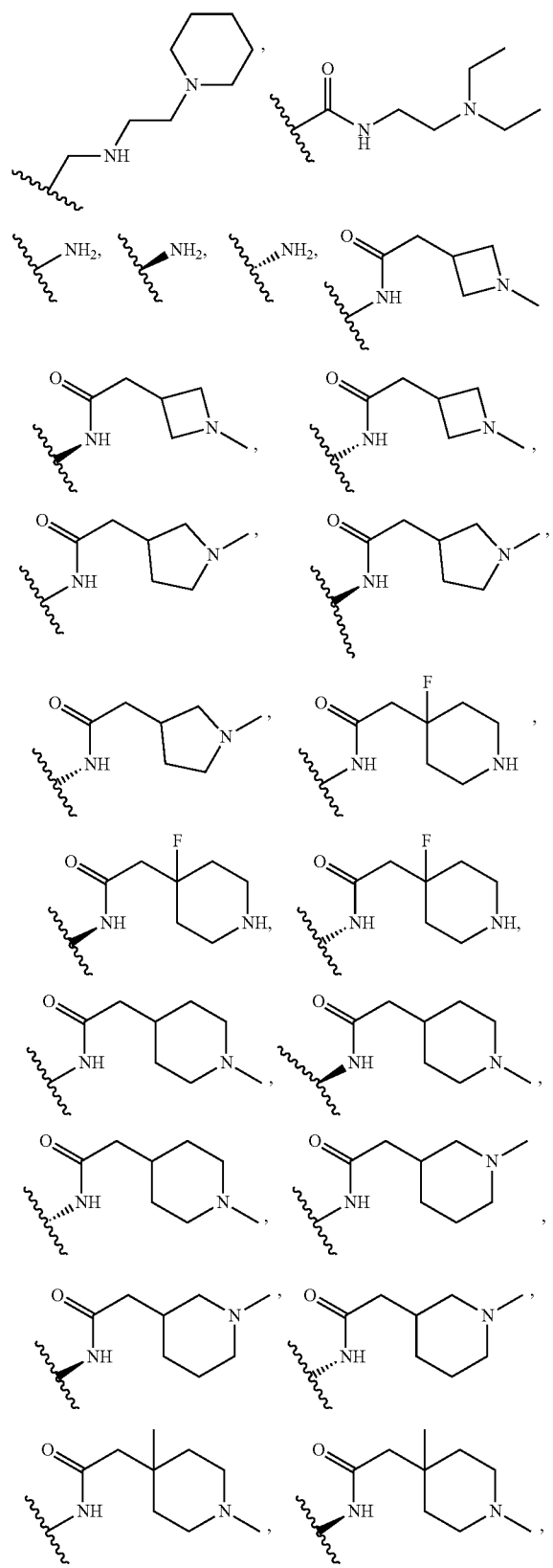

-continued

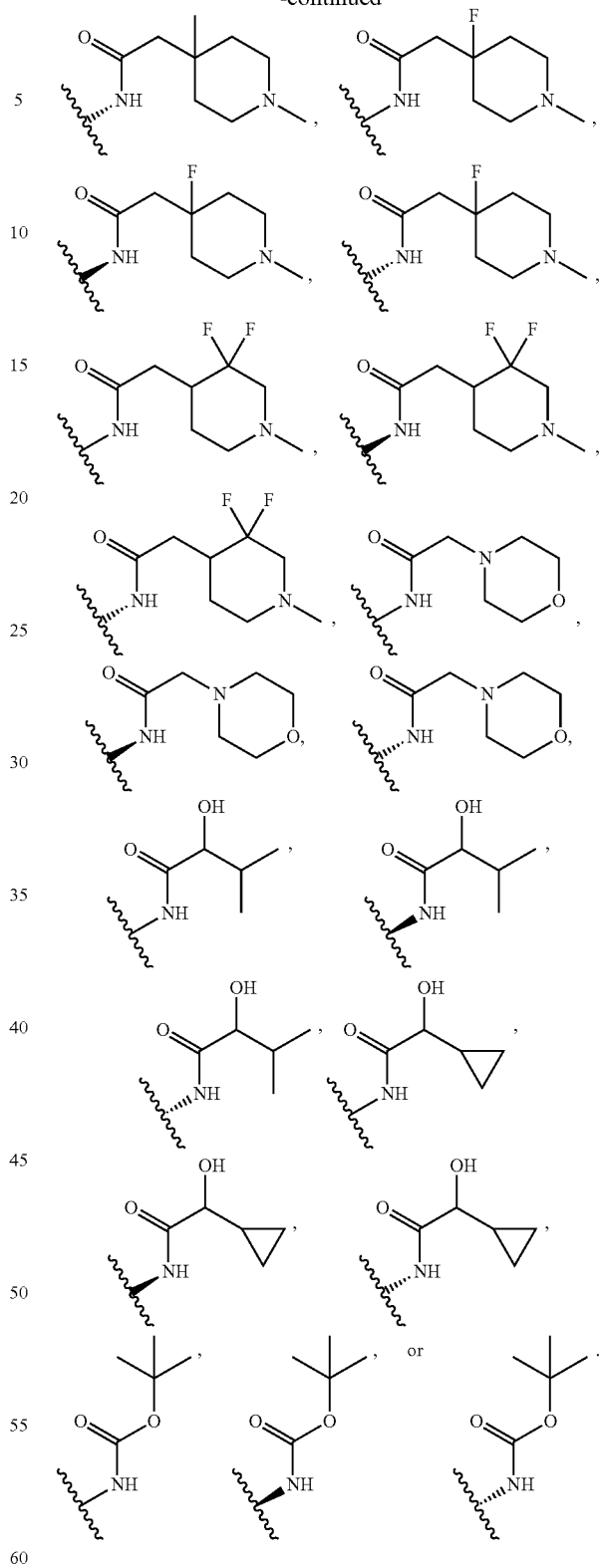

8. The compound of claim 1 or a pharmaceutically acceptable salt thereof, wherein each $R^5$ is independently halogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

9. The compound of claim 8 or a pharmaceutically acceptable salt thereof, wherein each $R^5$ is independently methyl, ethyl, propyl, i-propyl, butyl, s-butyl, t-butyl, straight or branched pentyl, or straight or branched hexyl; each of which is optionally substituted; or each $R^5$ is independently —F, —Cl, —Br, or —I.

10. The compound of claim 1, of formula I-a,

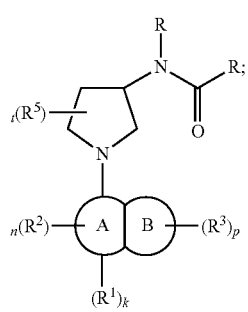

I-a or a pharmaceutically acceptable salt thereof.

11. The compound of claim 1, of formula I-c,

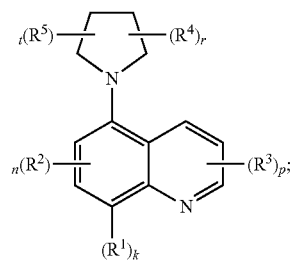

I-c or a pharmaceutically acceptable salt thereof.

12. The compound of claim 1, of formula I-d,

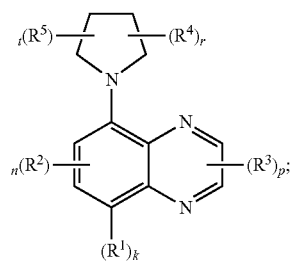

I-d or a pharmaceutically acceptable salt thereof.

13. The compound of claim 1, which is selected from the group consisting of compounds of the following Table and their pharmaceutically acceptable salts:

| Compound Number | Example Number | Chemical Structure |
|---|---|---|
| 17 | 7 | 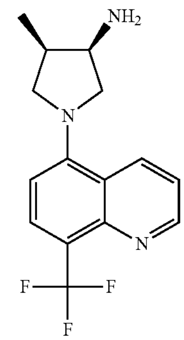 [SMILES: C[C@@H]1CN(c2ccc(C(F)(F)F)c3ncccc23)C[C@@H]1N] |
| 18 | 8 | 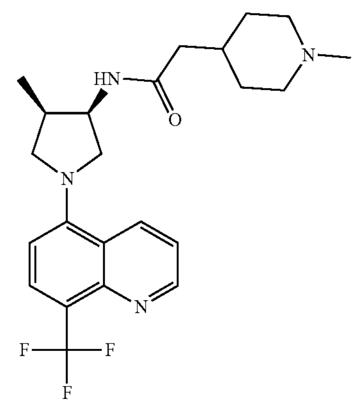 |
| 19 | 9 | 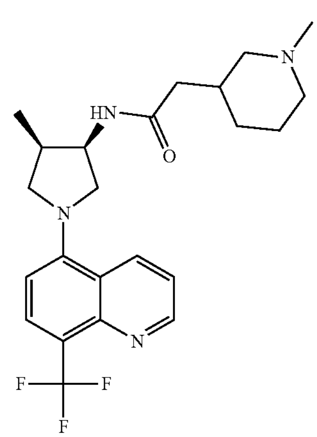 |

Isomer 1

-continued
| Compound Number | Example Number | Chemical Structure |
|---|---|---|
| 20 | 9 | 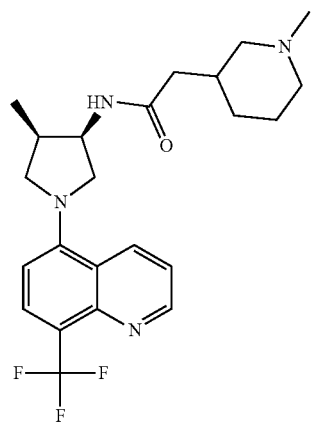<br>Isomer 2 |
| 21 | 9 | 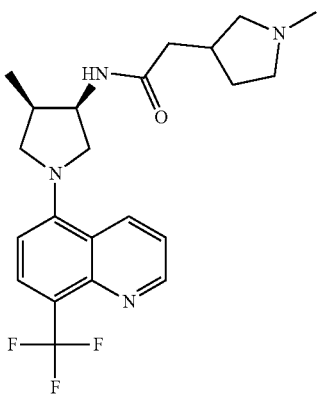<br>Isomer 1 |
| 22 | 9 | 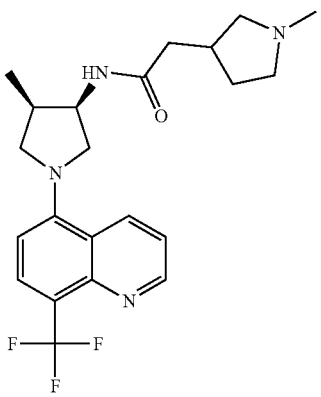<br>Isomer 2 |
-continued
| Compound Number | Example Number | Chemical Structure |
|---|---|---|
| 23 | 8 | 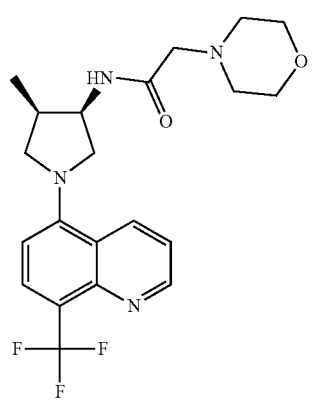 [SMILES: C[C@@H]1CN(c2ccc(C(F)(F)F)c3ncccc23)C[C@@H]1NC(=O)CN1CCOCC1] |
| 24 | 8 | 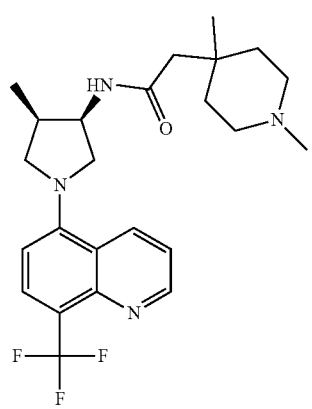 |
| 25 | 10 | 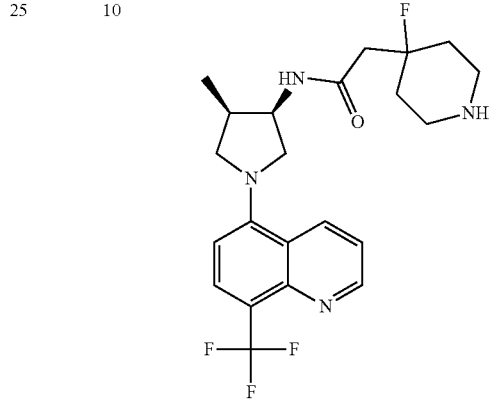 |

| Compound Number | Example Number | Chemical Structure |
|---|---|---|
| 26 | 11 | 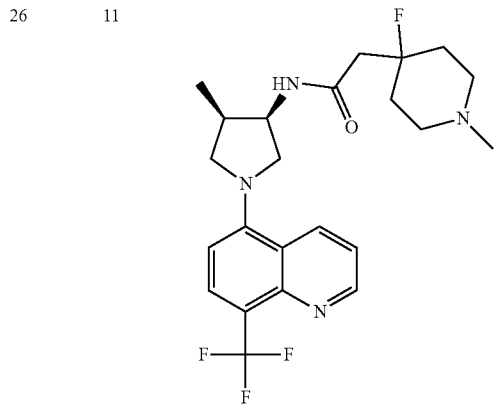 |
| 27 | 12 | 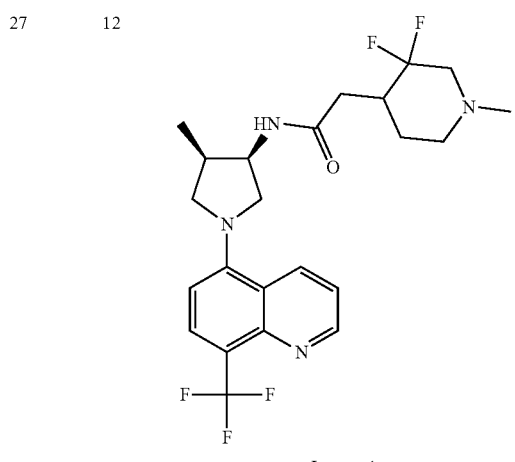
Isomer 1 |
| 28 | 12 | 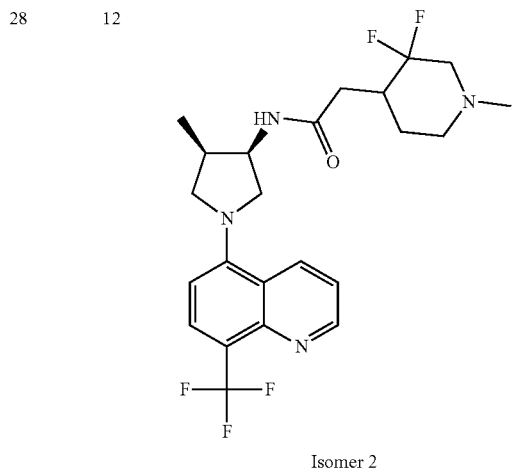
Isomer 2 |
| 29 | 9 | 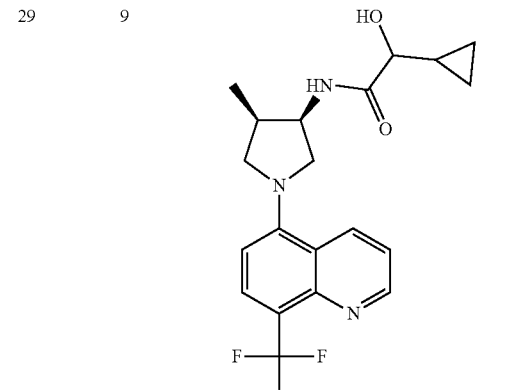
Isomer 1 |
| 30 | 9 | 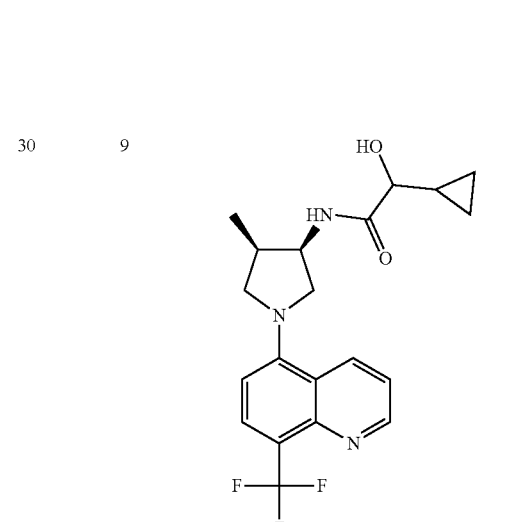
Isomer 2 |
| 31 | 8 | 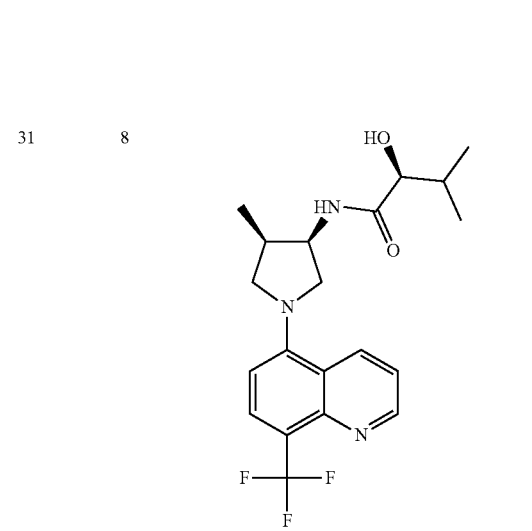 |

-continued
| Compound Number | Example Number | Chemical Structure |
|---|---|---|
| 32 | 8 | 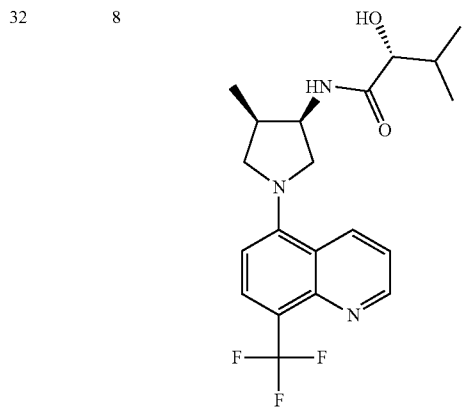 |
| 33 | 13 | 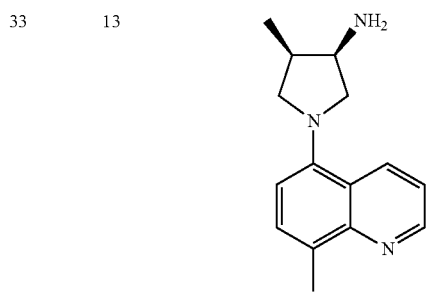 |
| 34 | 14 | 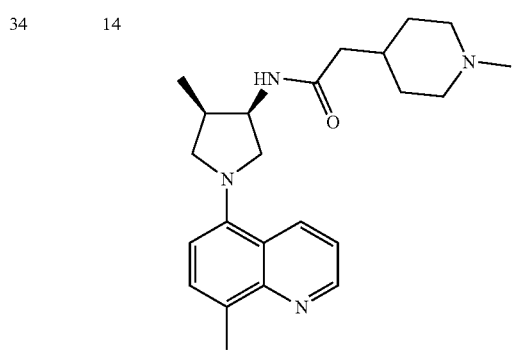 |
| 35 | 15 | 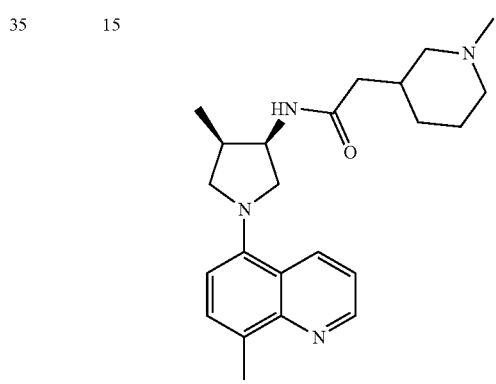<br>Isomer 1 |
-continued
| Compound Number | Example Number | Chemical Structure |
|---|---|---|
| 36 | 15 | 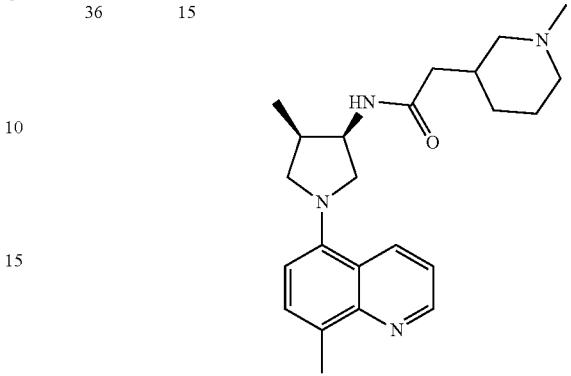<br>Isomer 2 |
| 37 | 15 | 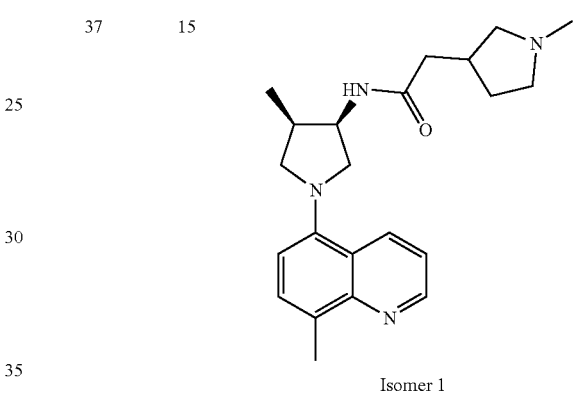<br>Isomer 1 |
| 38 | 15 | 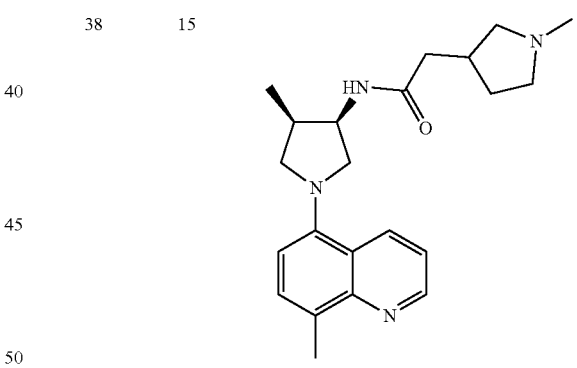<br>Isomer 2 |
| 39 | 14 | 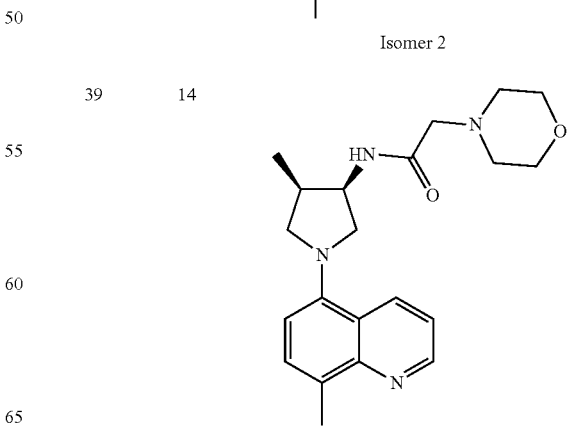 |

-continued
| Compound Number | Example Number | Chemical Structure |
|---|---|---|
| 40 | 14 | 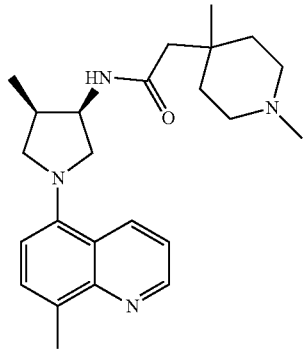 |
| 41 | 16 | 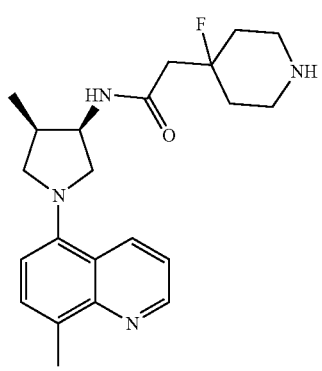 [SMILES: Cc1ccc(N2C[C@@H](C)[C@@H](NC(=O)CC3(F)CCNCC3)C2)c2cccnc12] |
| 42 | 17 | 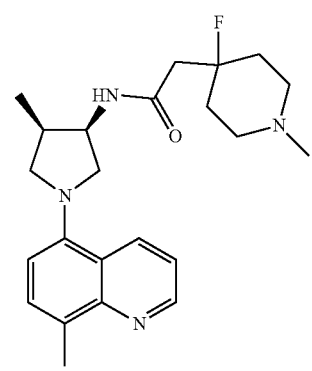 |
| 43 | 18 | 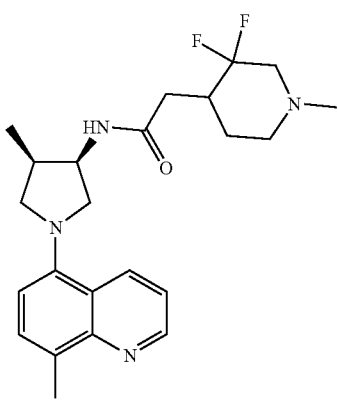\ Isomer 1 |
-continued
| Compound Number | Example Number | Chemical Structure |
|---|---|---|
| 44 | 18 | 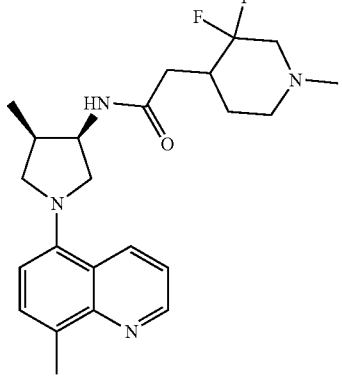\ Isomer 2 |
| 45 | 15 | 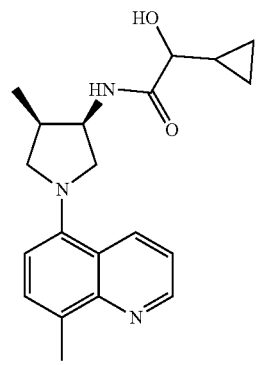\ Isomer 1 |
| 46 | 15 | 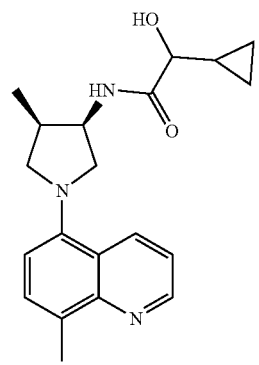\ Isomer 2 |
| 47 | 14 | 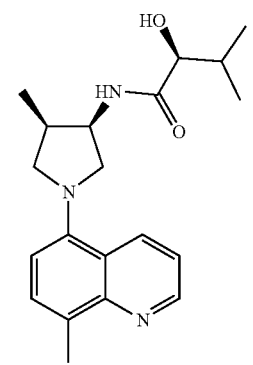 [SMILES: Cc1ccc(N2C[C@@H](C)[C@@H](NC(=O)[C@@H](O)C(C)C)C2)c2cccnc12] |

-continued

| Compound Number | Example Number | Chemical Structure |
|---|---|---|
| 48 | 14 | 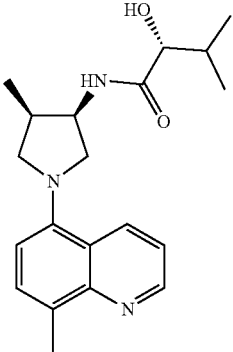 [SMILES: Cc1ccc(N2C[C@@H](C)[C@@H](NC(=O)[C@H](O)C(C)C)C2)c2cccnc12] |
| 49 | 19 | 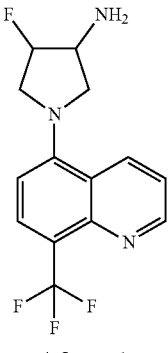<br>cis Isomer 1, and |
| 50 | 19 | 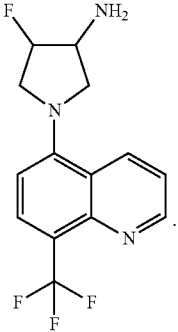<br>cis Isomer 2 |

14. A pharmaceutical composition, comprising:
a compound of claim 1 or a pharmaceutically acceptable salt thereof, and a pharmaceutically acceptable adjuvant, carrier, or vehicle.

15. A method for inhibiting TLR7/8, or a mutant thereof, activity in a patient or in a biological sample, said method comprising:

administering to said patient or contacting said biological sample with a compound of claim 1 or a physiologically acceptable salt thereof.

16. A method for treating a TLR7/8-mediated disorder in a patient in need thereof, comprising:

administering to said patient a compound of claim 1 or a physiologically acceptable salt thereof;
wherein the disorder is selected from the group consisting of Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Crohn's Disease and Ulcerative Colitis), Hyperimmunoglobulinemia D, periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

17. A method for treating cancer in a subject, the method comprising:
administering to said subject a compound of claim 1 or a physiologically acceptable salt thereof.

* * * * *